(12) United States Patent
Usui et al.

(10) Patent No.: US 7,393,636 B2
(45) Date of Patent: Jul. 1, 2008

(54) METHOD FOR FORMING SELF-ASSEMBLY SUBSTANCE USING OLIGONUCLEOTIDE SYNTHESIZED BY GENE AMPLIFICATION REACTION, SELF-ASSEMBLY SUBSTANCE AND METHOD FOR DETECTING GENE

(75) Inventors: Mitsugu Usui, Abiko (JP); Mari Mitsuka, Yokohama (JP); Chikako Hakii, Yokohama (JP)

(73) Assignee: Sanko Junyaku Co., Ltd., Tokyo (JP)

( * ) Notice: Subject to any disclaimer, the term of this patent is extended or adjusted under 35 U.S.C. 154(b) by 380 days.

(21) Appl. No.: 10/495,065

(22) PCT Filed: Oct. 30, 2002

(86) PCT No.: PCT/JP02/11321

§ 371 (c)(1),
(2), (4) Date: May 7, 2004

(87) PCT Pub. No.: WO03/040367

PCT Pub. Date: May 15, 2003

(65) Prior Publication Data

US 2006/0286553 A1 Dec. 21, 2006

(30) Foreign Application Priority Data

May 8, 2002 (JP) .............................. 2002-132402

(51) Int. Cl.
*C12Q 1/68* (2006.01)
*C12P 19/34* (2006.01)
*C07H 21/04* (2006.01)
*C07H 21/02* (2006.01)

(52) U.S. Cl. .................. 435/6; 435/91.2; 536/23.1; 536/24.3; 536/24.33

(58) Field of Classification Search .............. 435/6, 435/91.2; 536/23.1, 24.3, 24.33

See application file for complete search history.

(56) References Cited

U.S. PATENT DOCUMENTS

| 5,591,609 | A  | * | 1/1997 | Auerbach .................. 435/91.2 |
| 6,261,846 | B1 | * | 7/2001 | Usui ............................. 435/6 |
| 6,277,607 | B1 | * | 8/2001 | Tyagi et al. .................... 435/6 |
| 2001/0019835 | A1 | | 9/2001 | Usui .......................... 435/91.1 |

FOREIGN PATENT DOCUMENTS

| EP | 1 002 877 | 5/2000 |
| EP | 1 188 841 | 3/2002 |
| JP | 2000-201687 | 7/2000 |
| WO | 01/75157 | 10/2001 |

OTHER PUBLICATIONS

Honeyman et al. AJVR, 1999, vol. 60(6). p. 734-737.*

* cited by examiner

*Primary Examiner*—Kenneth R. Horlick
*Assistant Examiner*—Joyce Tung
(74) *Attorney, Agent, or Firm*—Wenderoth, Lind & Ponack, L.L.P.

(57) ABSTRACT

There is provided a method for forming a self-assembly substance using oligonucleotides without using special instruments or complicated procedures, an self-assembly substance formed by the method for forming the self-assembly substance, and a method for detecting an amplified target gene at a low cost and in a simple way by making use of the method for forming the self-assembly substance. In the method for forming the self-assembly substance using a self-assembly reaction of oligonucleotides, the oligonucleotides comprise oligonucleotides synthesized by a gene amplification reaction. The oligonucleotides synthesized by the gene amplification reaction are detected by forming a self-assembly substance by the use of the method for forming the self-assembly substance of oligonucleotides, and by detecting the formed self-assembly substance.

12 Claims, 52 Drawing Sheets

Formation of a self-assembly substance

FIG. 7
(a) A pair of gene fragments amplified by a conventional gene amplification method and complementary to each other
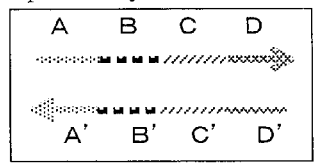
(b) A pair of dimer-forming probes
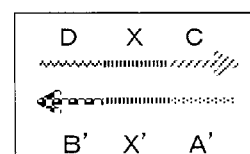
Formation of a dimer-probe
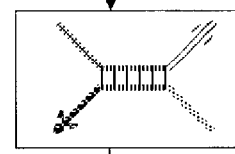
(c) Formation of a self-assembly substance
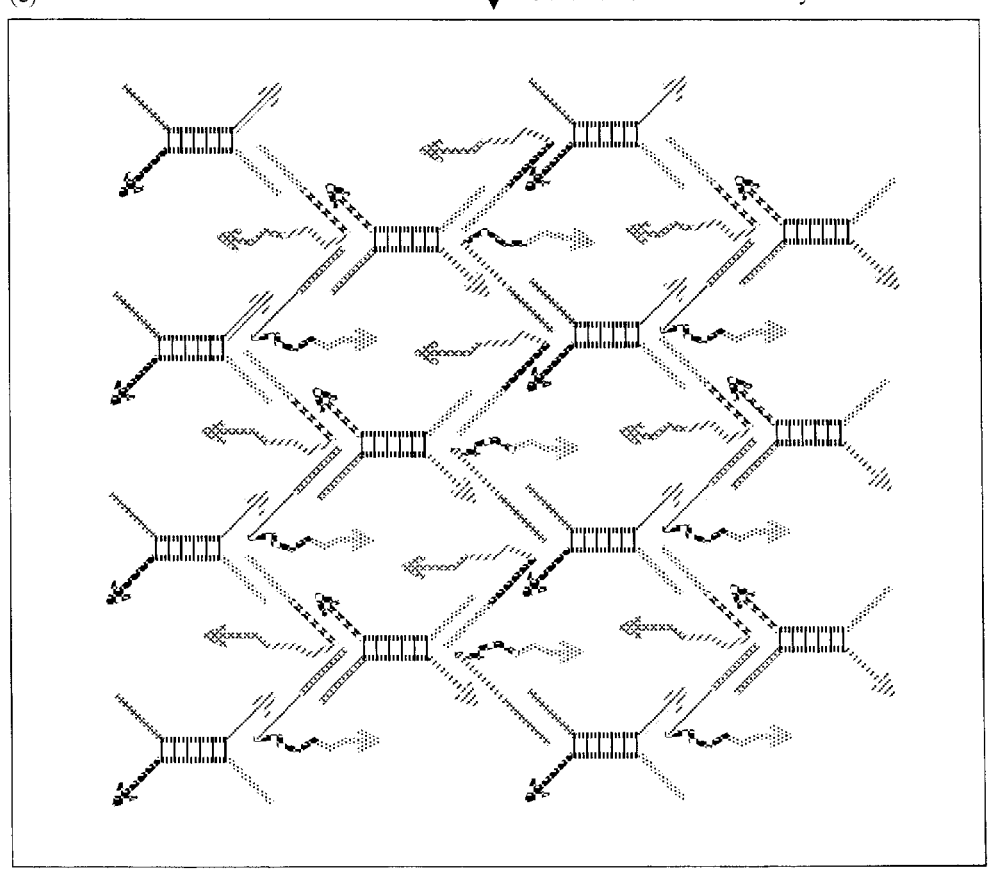

FIG. 8
(a) A pair of gene fragments amplified by a conventional gene amplification method and complementary to each other
(b) A pair of dimer-forming probes
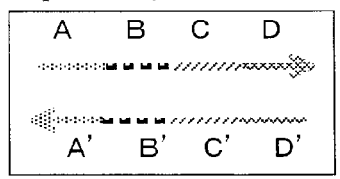
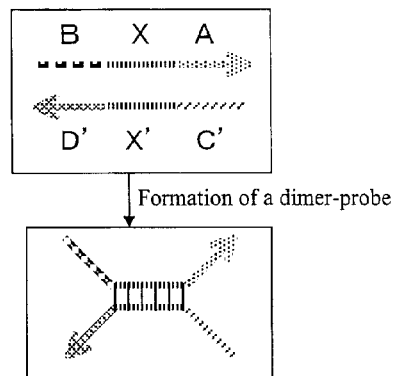
Formation of a dimer-probe
(c) Formation of a self-assembly substance
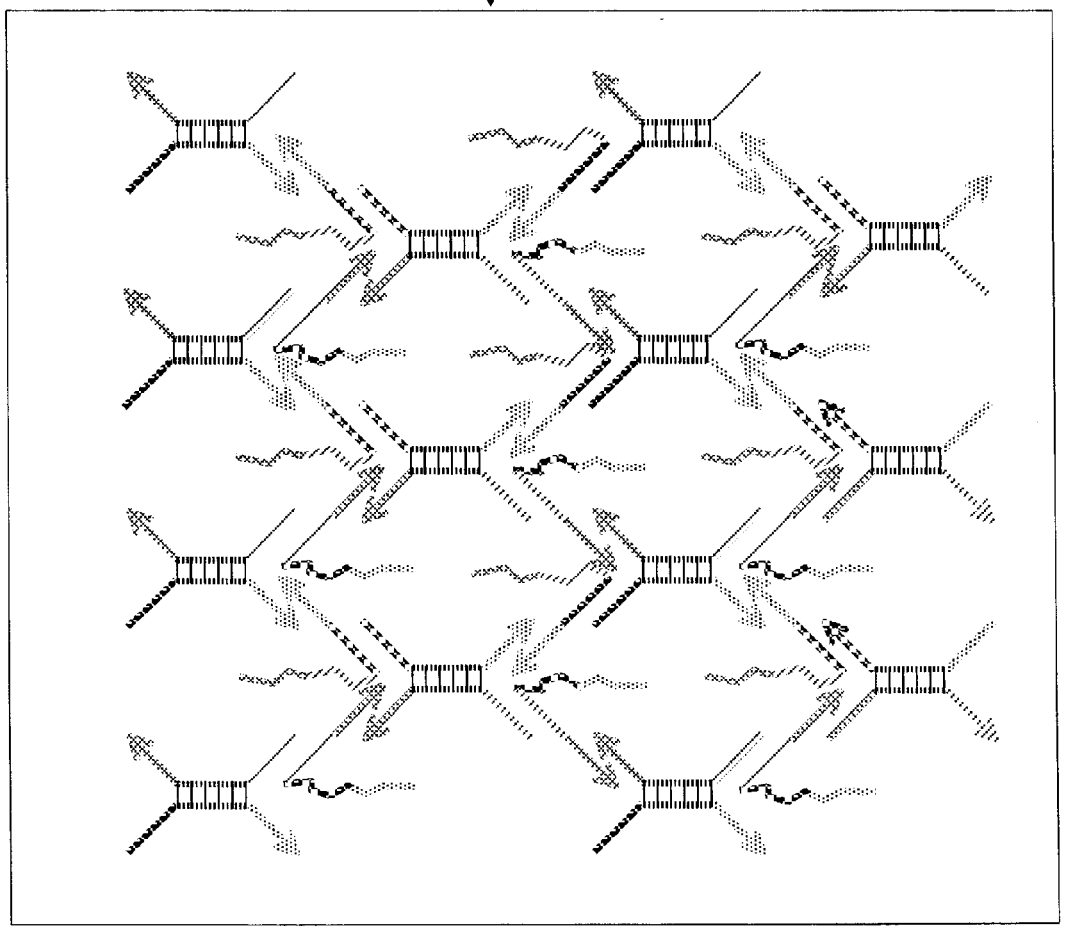

FIG. 9
(a) A pair of gene fragments amplified by a conventional gene amplification method and complementary to each other
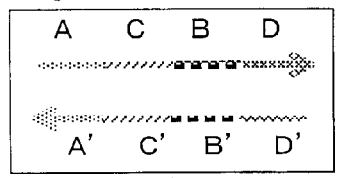
(b) A pair of dimer-forming probes
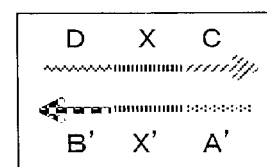
Formation of a dimer-probe
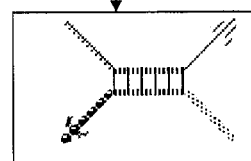
Formation of a self-assembly substance
(c)
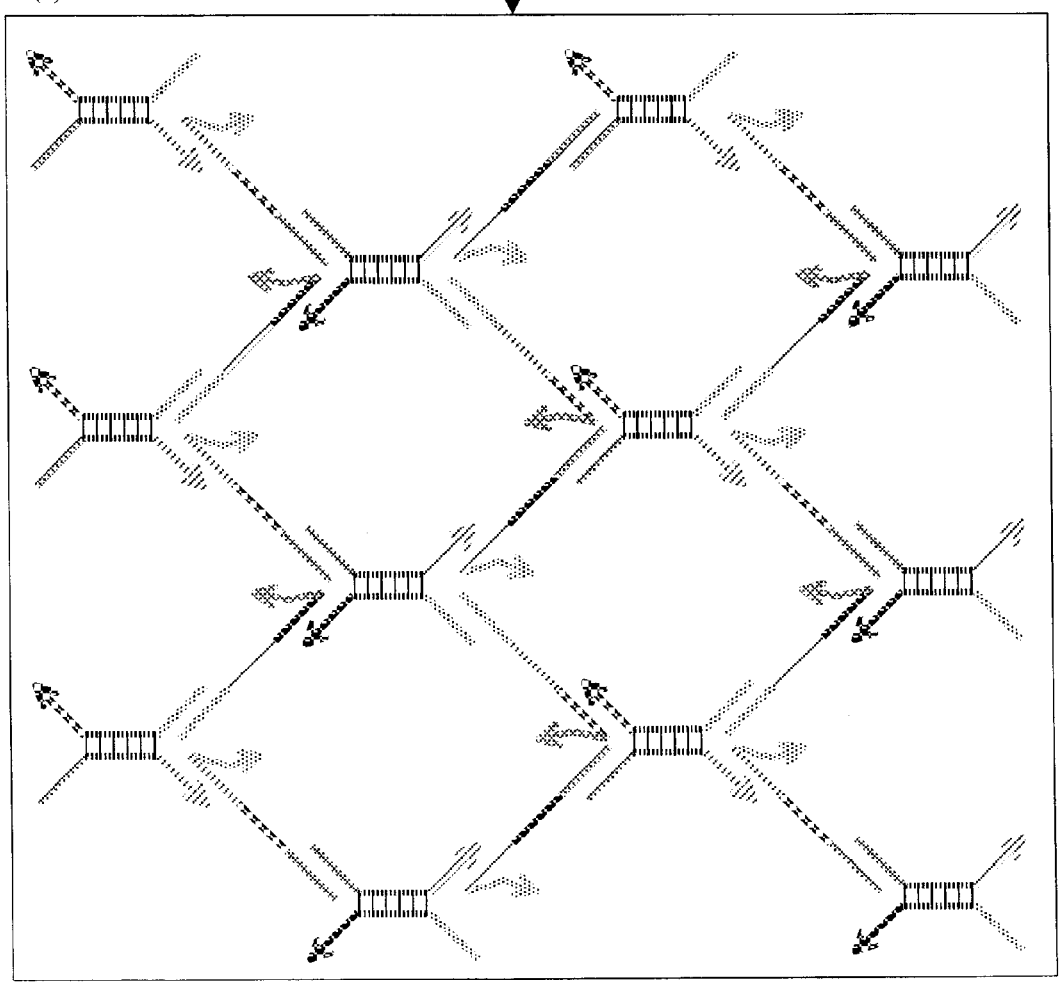

FIG. 10
(a) A pair of gene fragments amplified by a conventional gene amplification method and complementary to each other
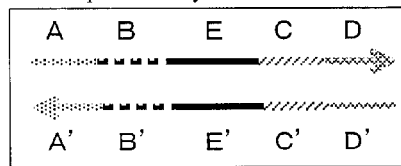
(b) A pair of dimer-forming probes
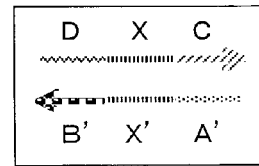
Formation of a dimer-probe
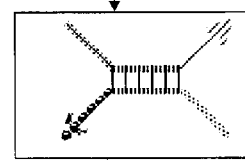
Formation of s self-assembly substance
(c)
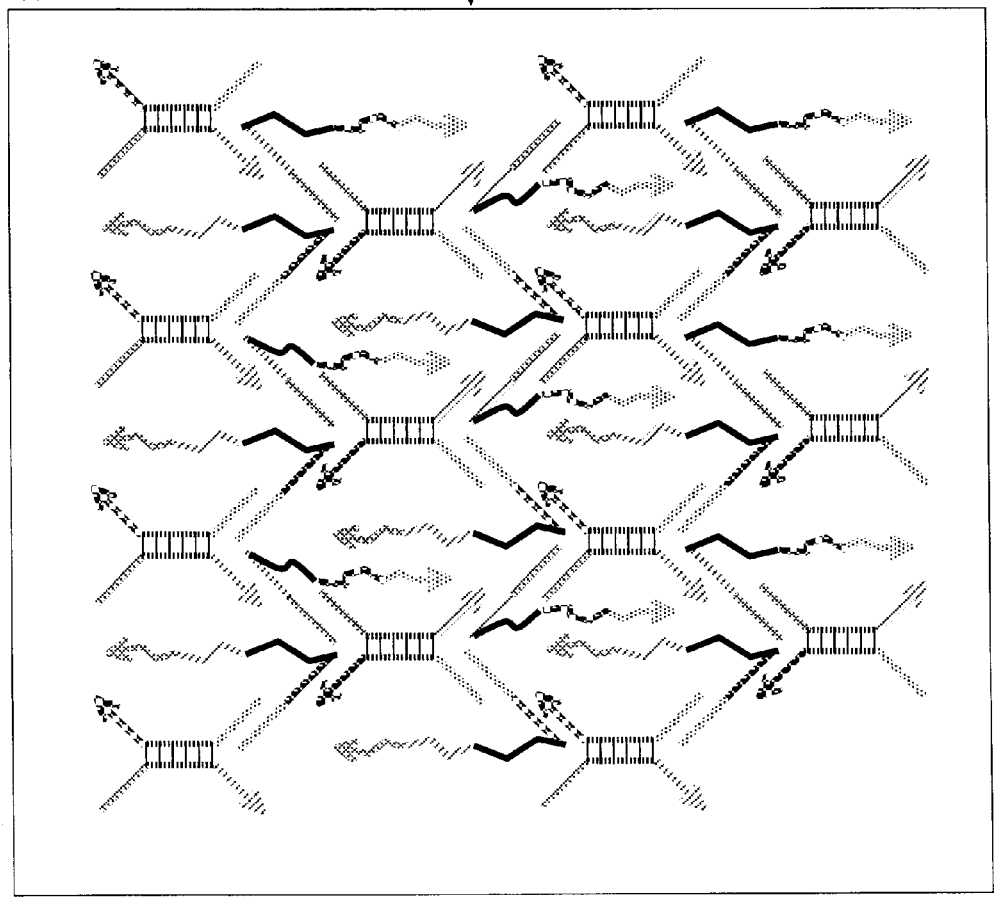

FIG. 11
(a) A pair of gene fragments amplified by a conventional gene amplification method and complementary to each other
(b) A pair of dimer-forming probes
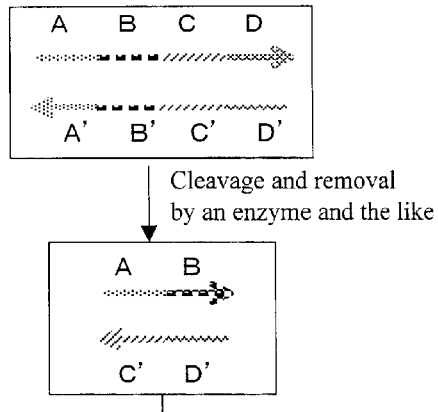
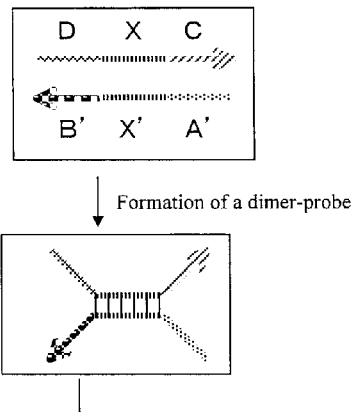
Cleavage and removal by an enzyme and the like
Formation of a dimer-probe
Formation of a self-assembly substance
(c)
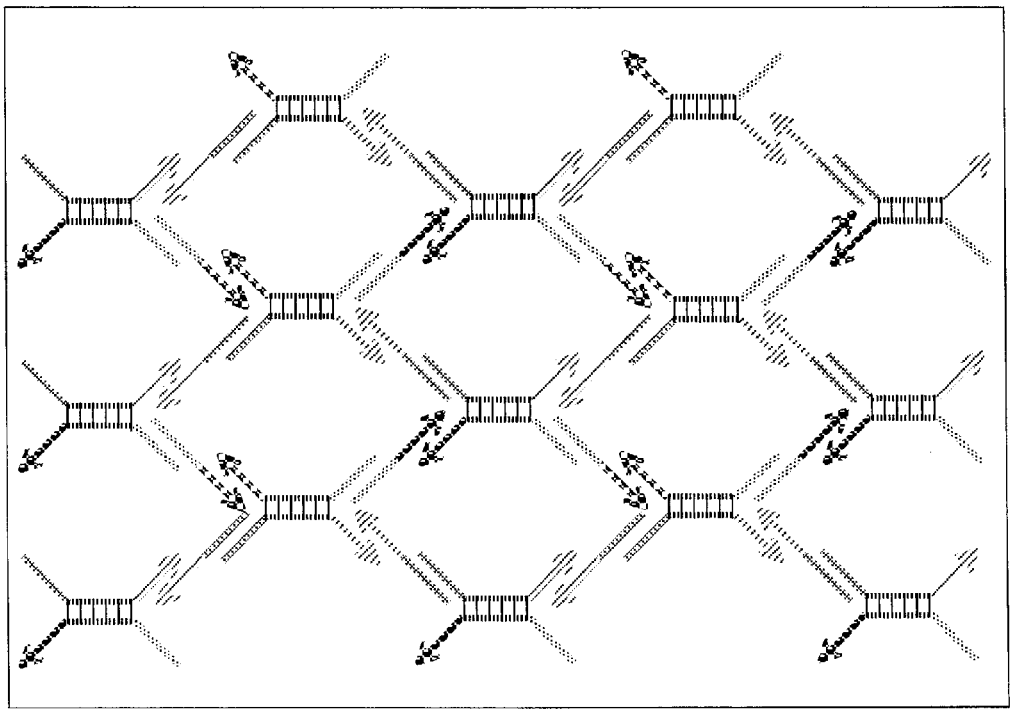

FIG. 12
(a) A pair of gene fragments amplified by a conventional gene amplification method and complementary to each other
(b) A pair of dimer-forming probes
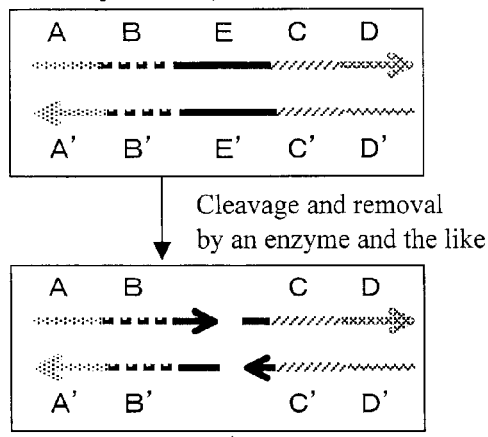
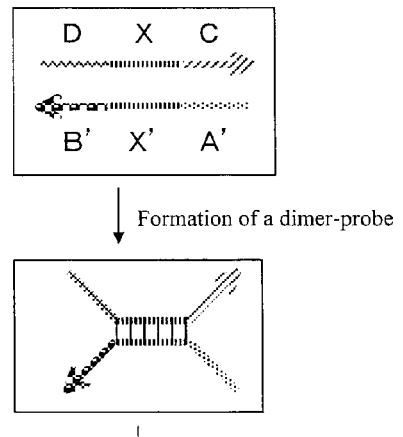
Cleavage and removal by an enzyme and the like
Formation of a dimer-probe
Formation of a self-assembly substance
(c)
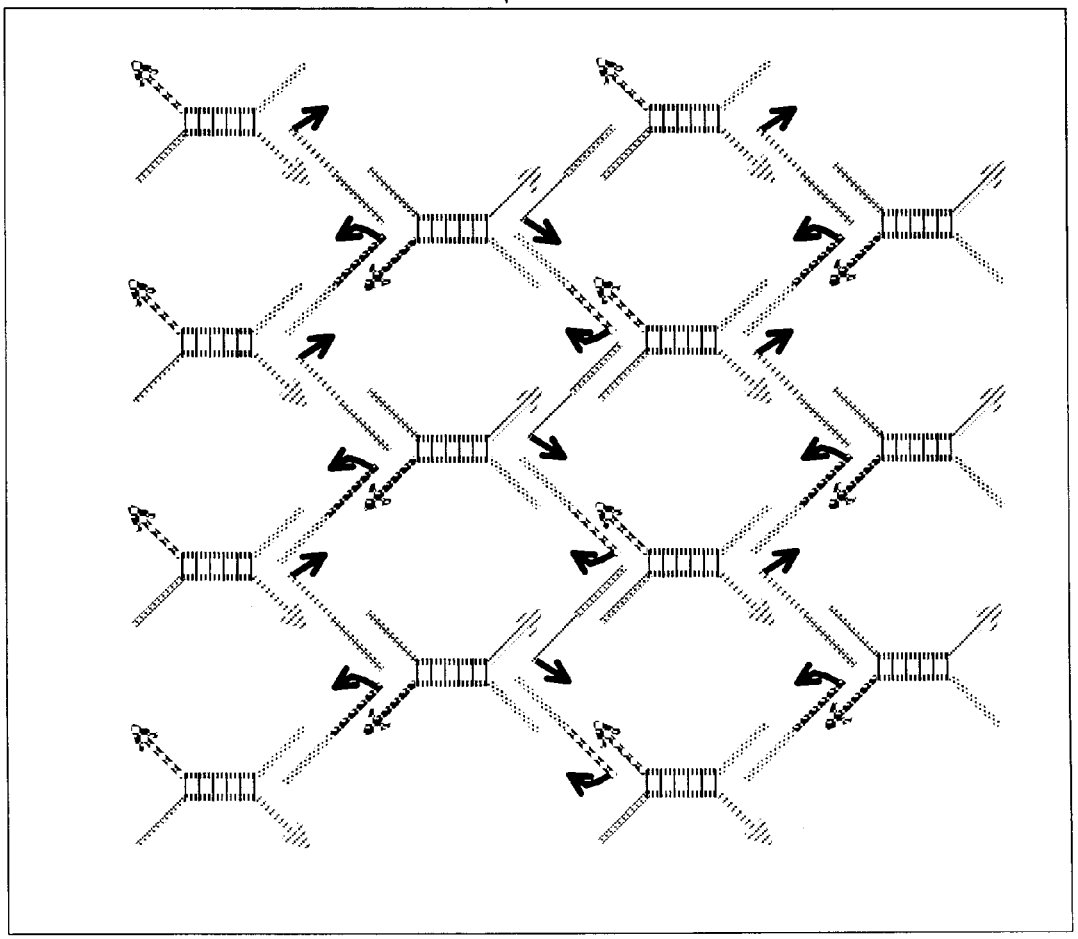

FIG. 13
(a) A pair of gene fragments amplified by a conventional gene amplification method and complementary to each other
(b) A pair of dimer-forming probes
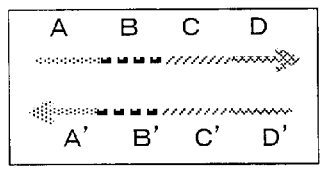
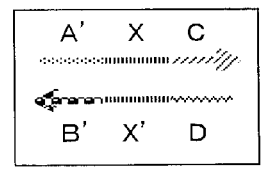
↓ Cleavage and removal by an enzyme and the like
↓ Formation of a dimer-probe
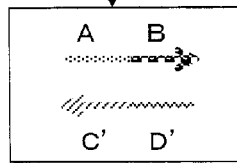
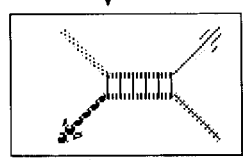
Formation of a self-assembly substance
(c)
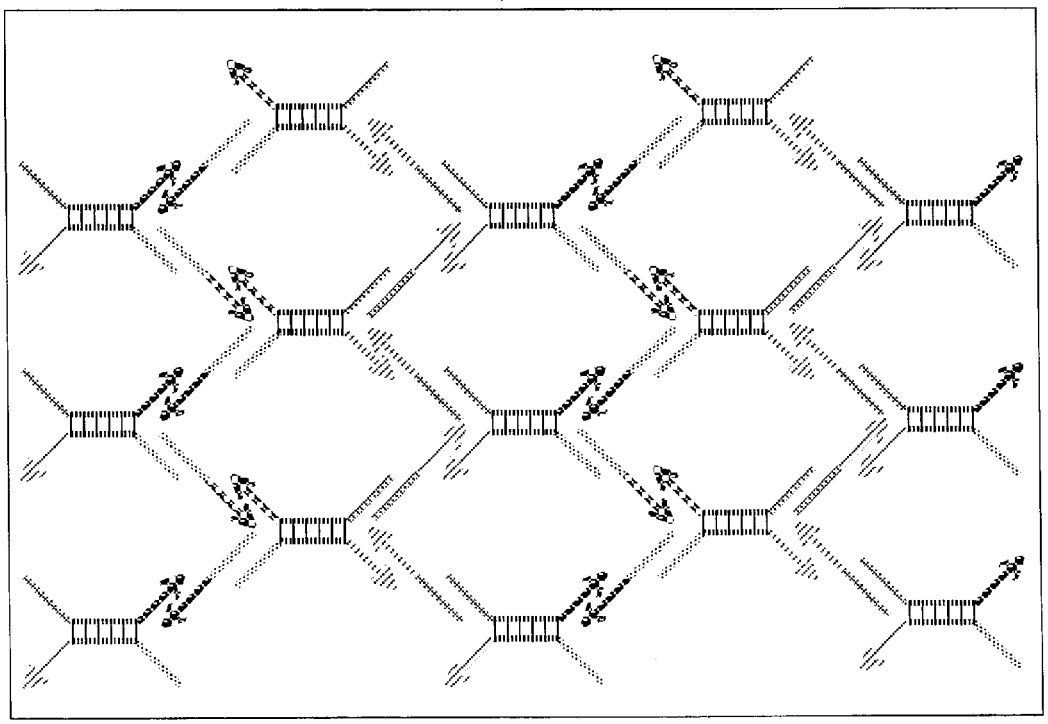

FIG. 14
(a) A single strand gene fragment amplified by a conventional gene amplification method
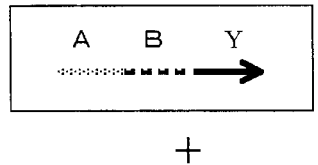
+
(c) A cross-linking prove prepared in advance
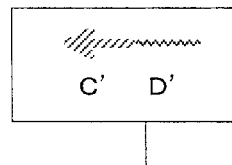
(b) A pair of dimer-forming probes
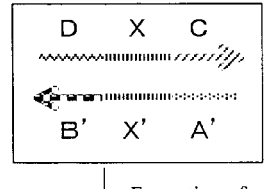
Formation of a dimer-probe
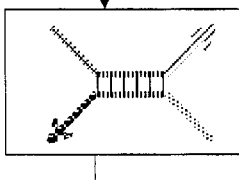
Formation of a self-assembly substance
(d)
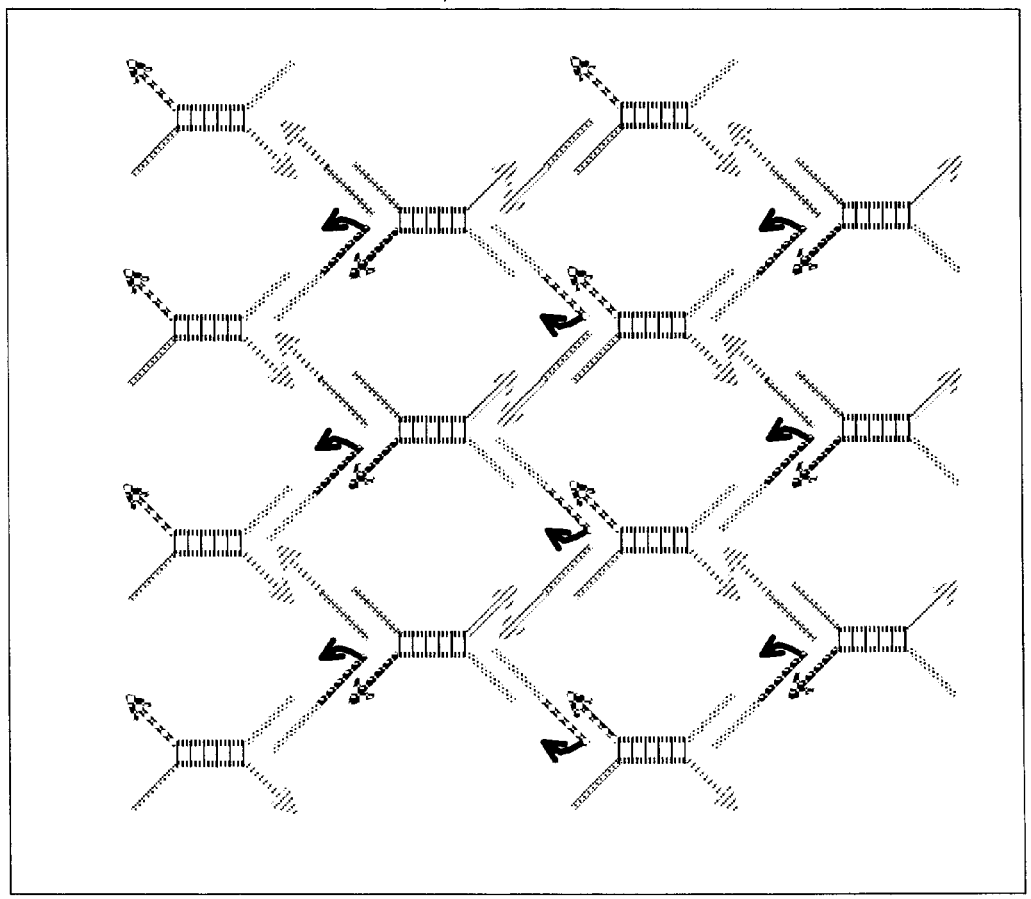

FIG. 16
(b) A pair of gene fragments amplified by gene amplification method using amplifying probes of RNA
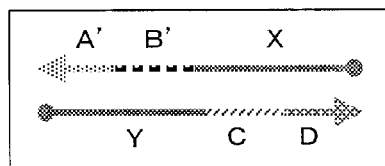
(d) A pair of dimer-forming probes
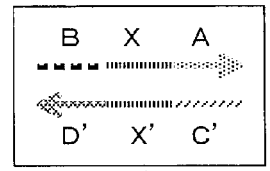
Cleavage by an RNase H
Formation of a dimer-probe
(c) 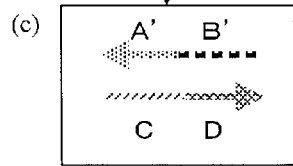
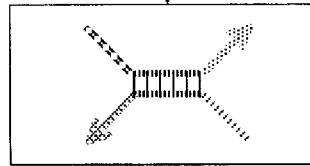
Formation of a self-assembly substance
(e) 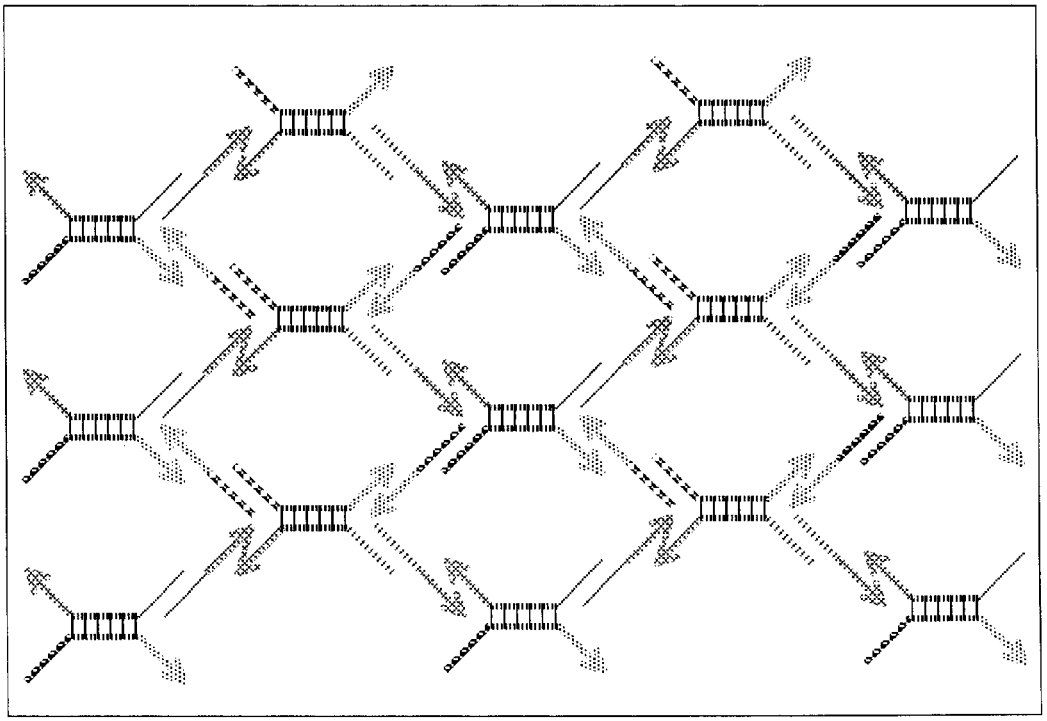

FIG. 17
Methylation of bases
(a)
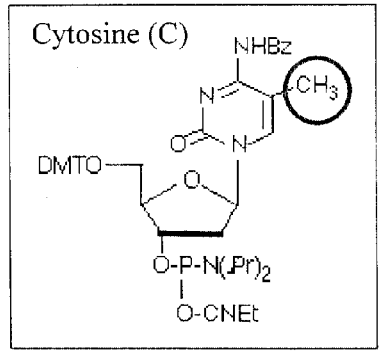
Cytosine (C)
(b)
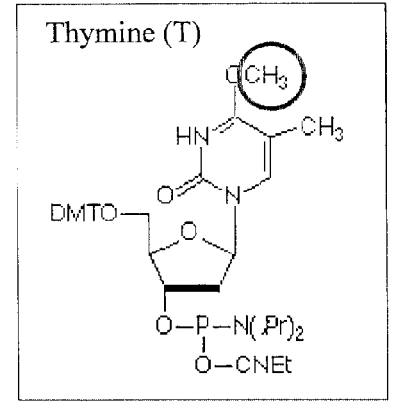
Thymine (T)
(c)
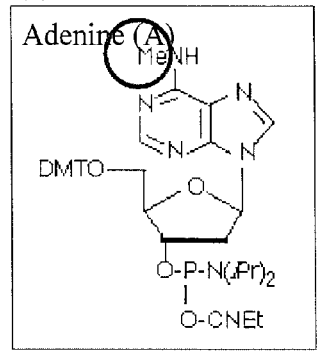
Adenine (A)
(d)
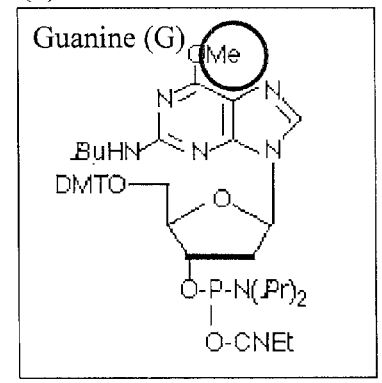
Guanine (G)

FIG. 19
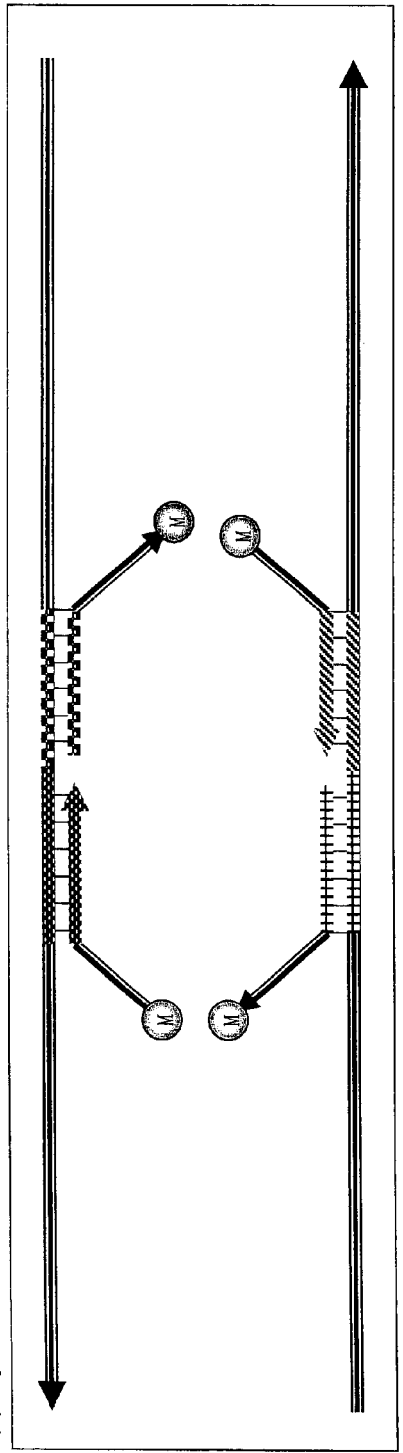
(c) Hybridization of methylated dimer-forming probes with target genes
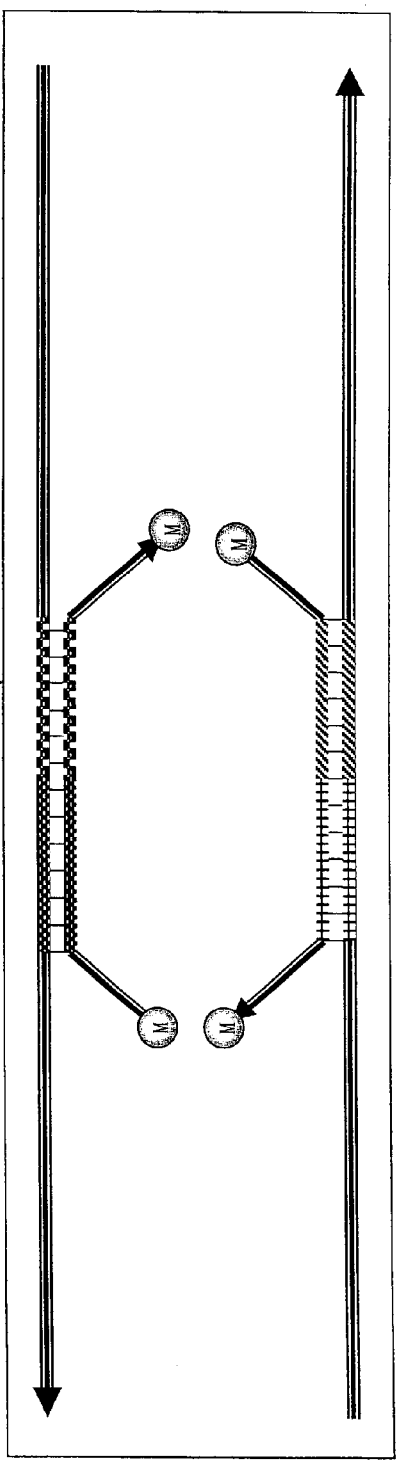
(d) Ligation reaction of methylated dimer-forming probes
Thermostable ligase added, followed by thermal cycling

FIG. 20
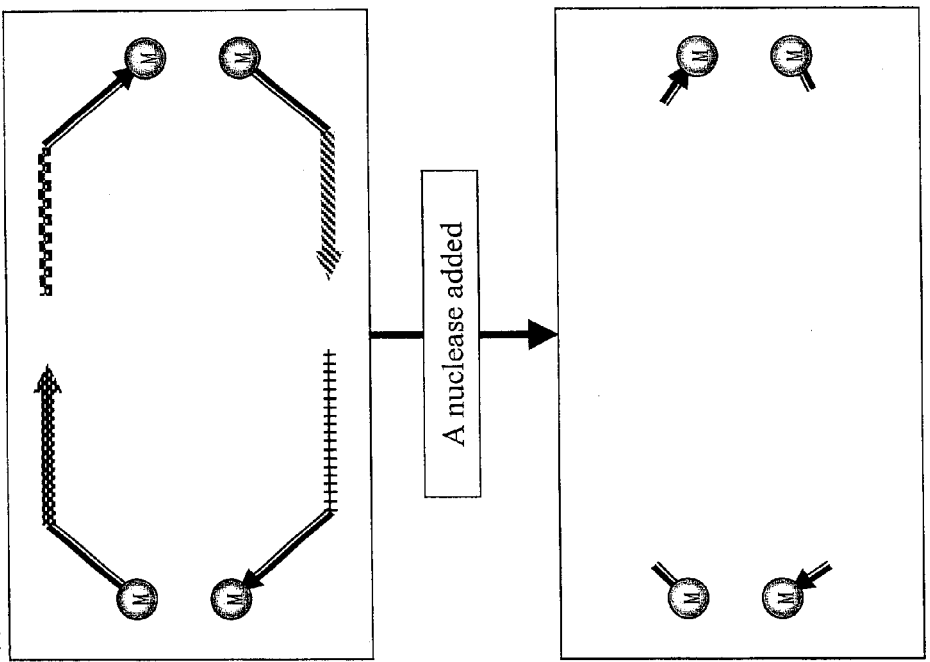
(f) Unreacted dimer-forming probes
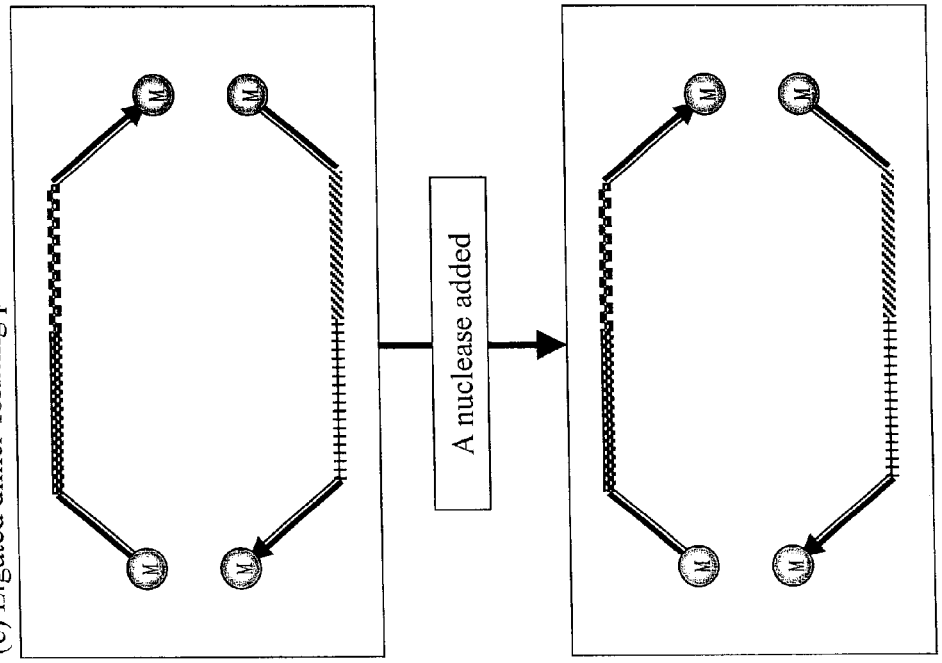
(e) Ligated dimer-forming probes (a) A target gene (b) Methylated amplifying probes

FIG. 24
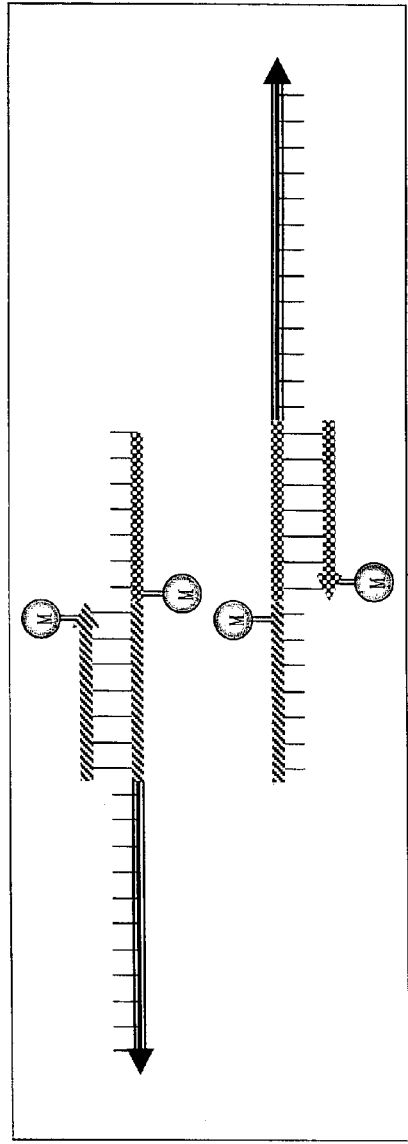
(e) Annealing of methylated amplifying probes with synthesized target genes
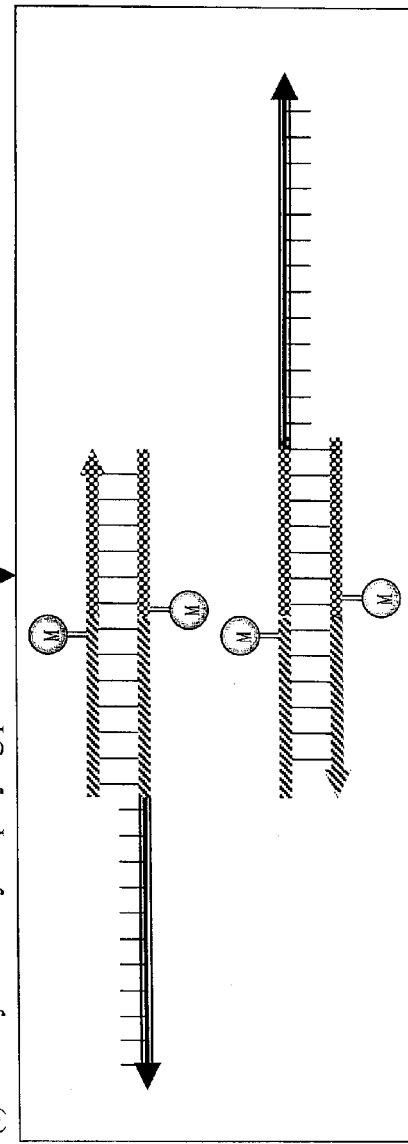
(f) DNA synthesis by amplifying probes
Thermal cycling

FIG. 25
(g) Synthetic probes
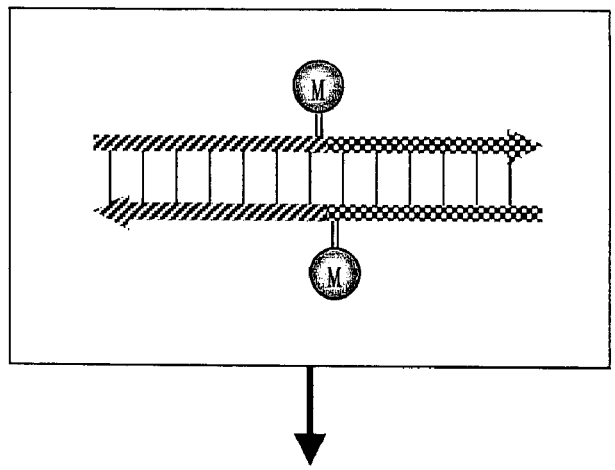
(h) Deletion of 5' regions in complementary chains (template) by a nuclease
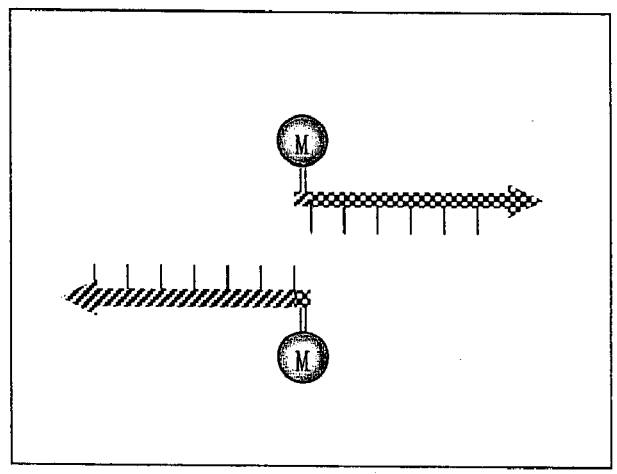

FIG. 26
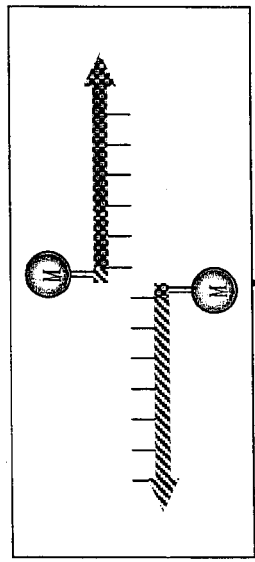
(i) Synthetic probes removed complementary chains (template) by a nuclease
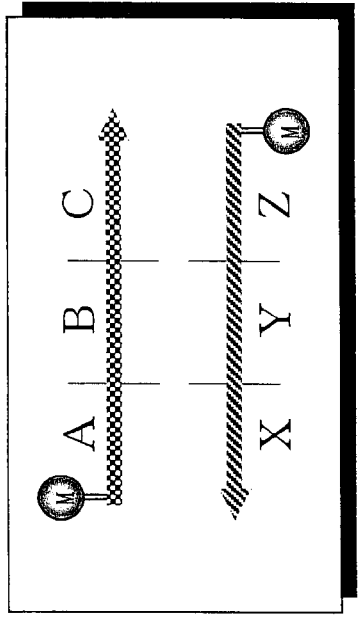
(k) Used as HCPs for formation of a self-assembly substance
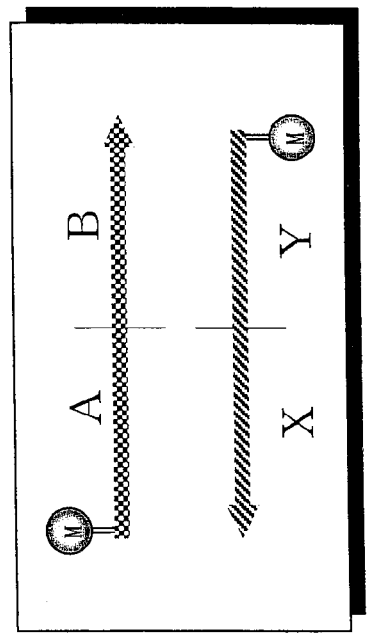
(j) Used as cross-linking probes for formation of a self-assembly substance

FIG. 29
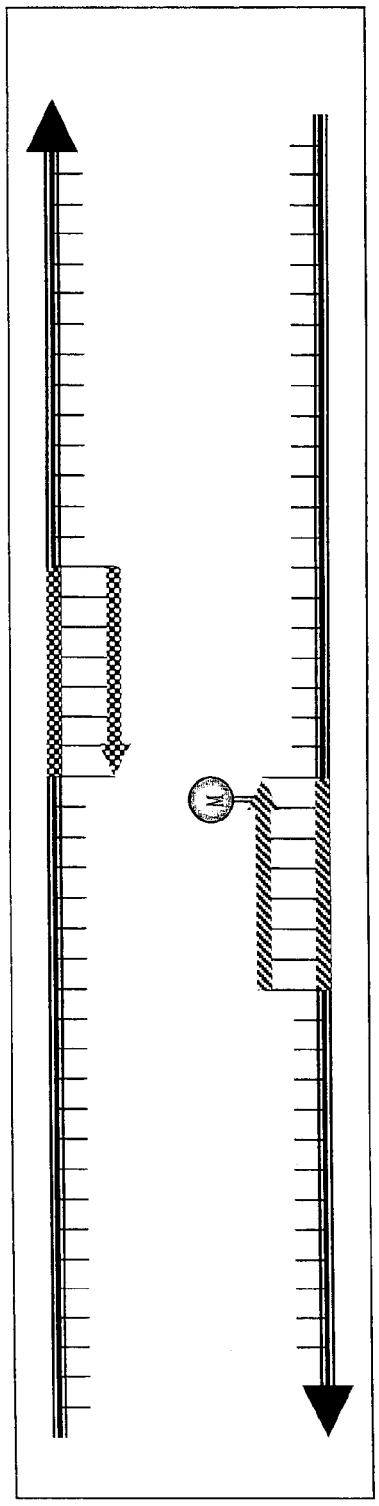
(c) Annealing of amplifying probes with target genes
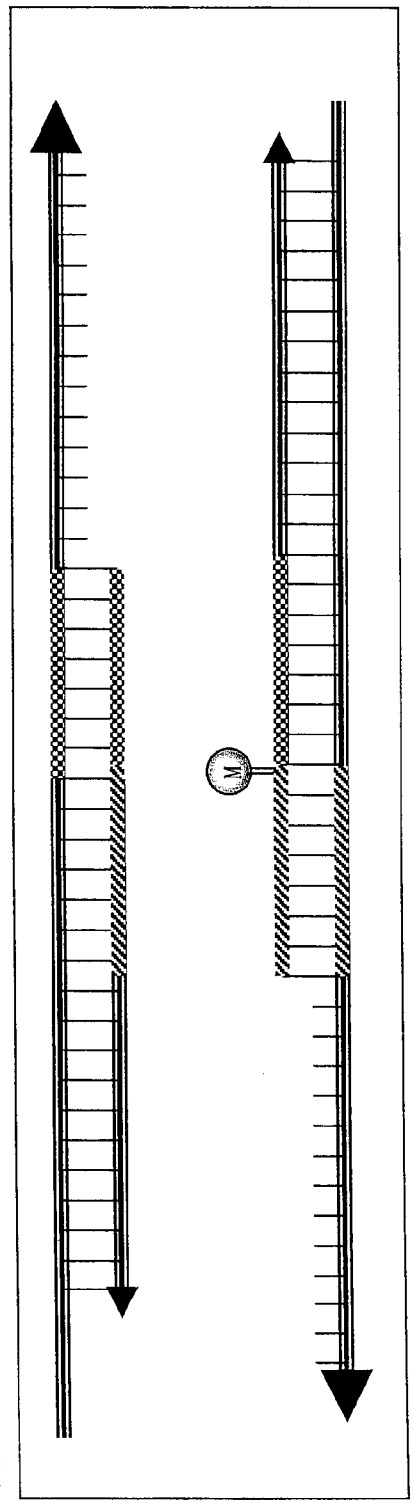
(d) DNA synthesis (e) Annealing of amplifying probes with synthesized target genes
(f) DNA synthesis by amplifying probes
Thermal cycling

FIG. 31
(g) Synthetic probes
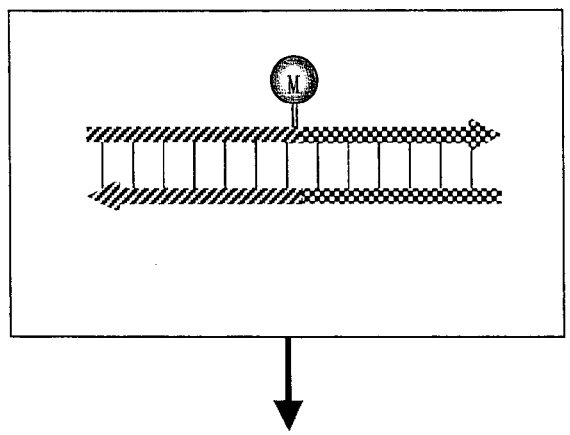
(h) Deletion of 5' regions in complementary chains (template) by a nuclease
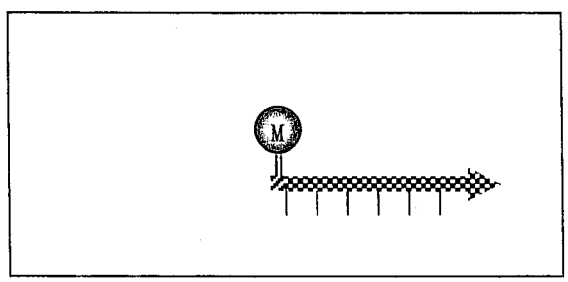

FIG. 32
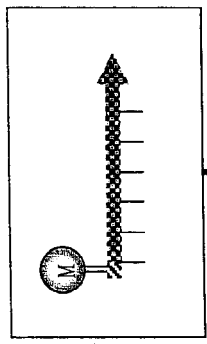
(i) A synthetic probe removed a complementary chain (template) by a nuclease
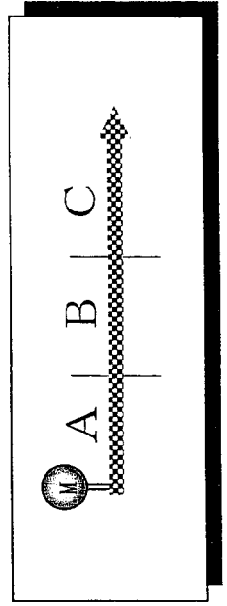
(k) Used as an HCP for formation of a self-assembly substance
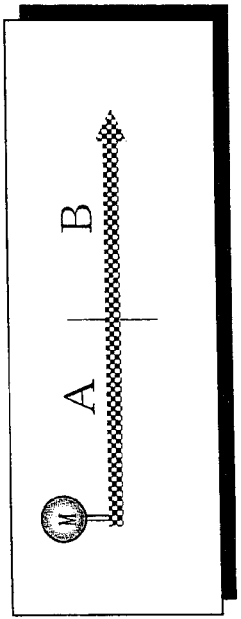
(j) Used as a cross-linking probe for formation of a self-assembly substance

FIG. 33
(l) A degraded synthetic probe
+ An unreacted probe
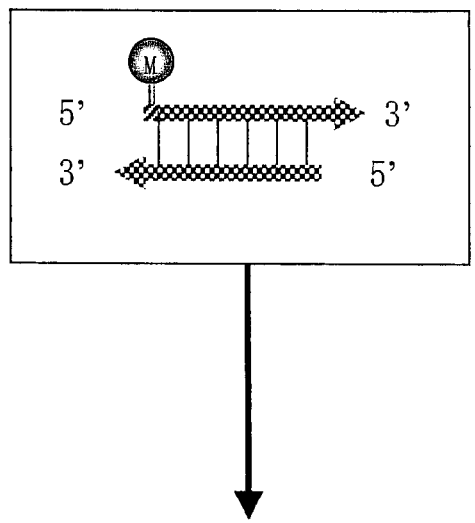
(m) Removal of excess amplifying probes by a nuclease
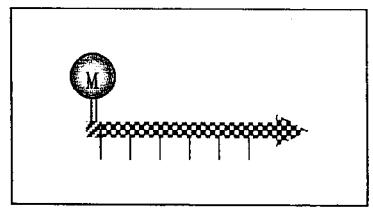

(a) A target gene (b) Methylated chimera type amplifying probes (c) Annealing of methylated chimera type amplifying probes with target genes (d) Split of RNA parts by an RNase H

FIG. 37
(h) Synthetic probes
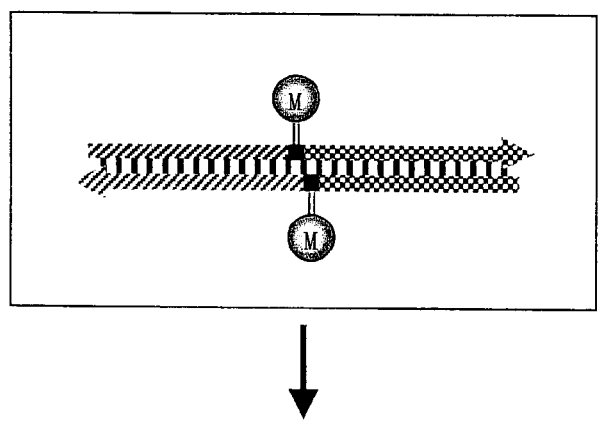
(i) Deletion of 5' regions of complementary chains (template) by a nuclease
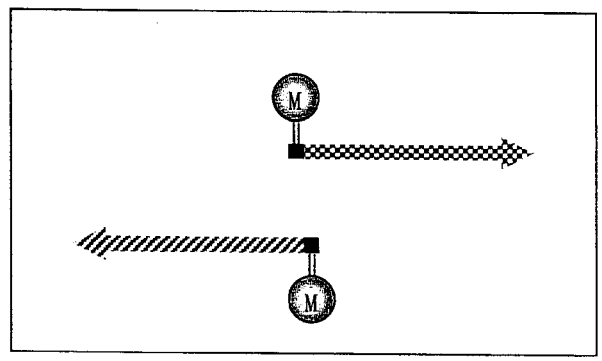

FIG. 38
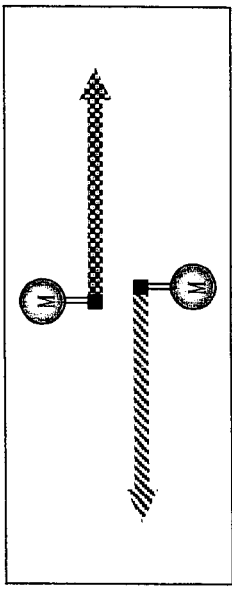
(j) Synthetic probes removed complementary chains (template) by a nuclease
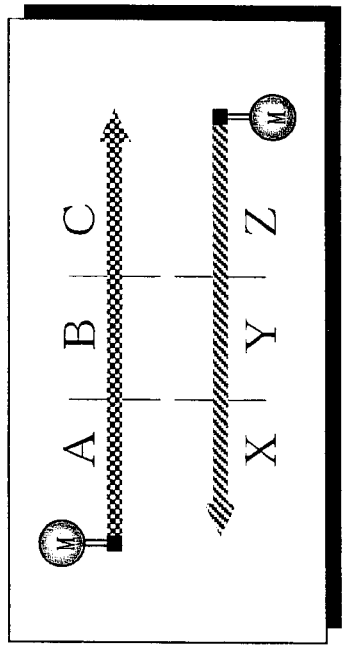
(l) Used as HCPs for formation of a self-assembly substance
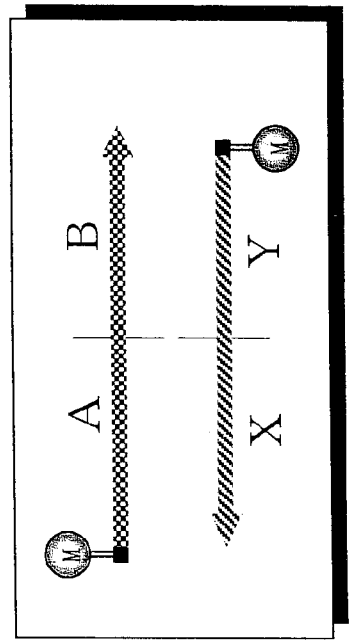
(k) Used as cross-linking probes for formation of a self-assembly substance (e) DNA synthesis with a DNA polymerase having strand displacement activity (f) Synthetic probes (g) Unreacted probes

FIG. 43
(h) Synthetic probes
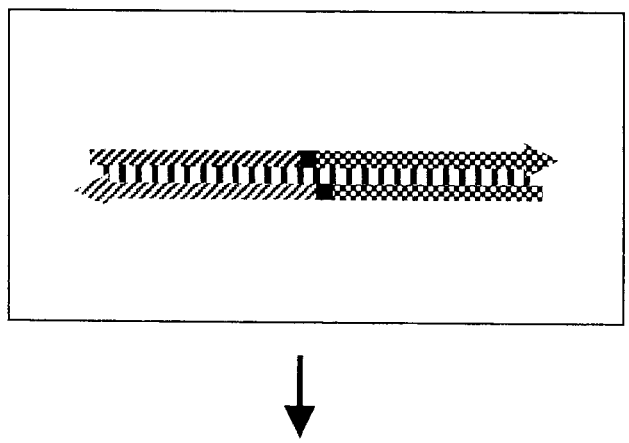
(i) Deletion of DNA from 5' end up to the front of an RNA part in complementary chains (template) by a nuclease
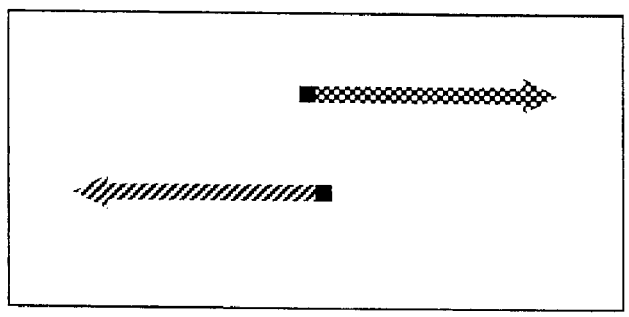

FIG. 44
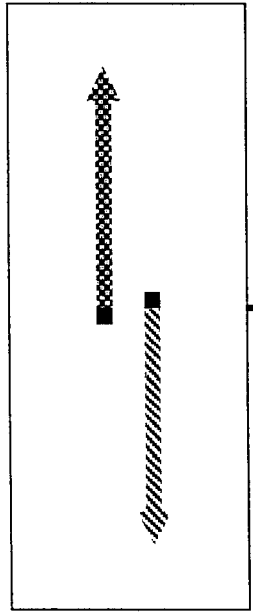
(j) Synthetic probes removed DNA from 5' end up to the front of an RNA part in complementary chains (template) by a nuclease
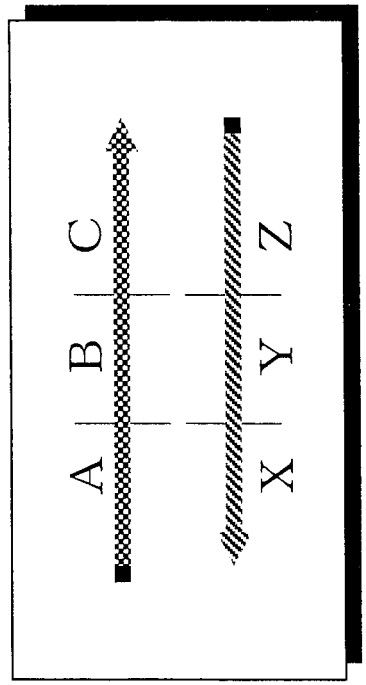
(l) Used as HCPs for formation of a self-assembly substance
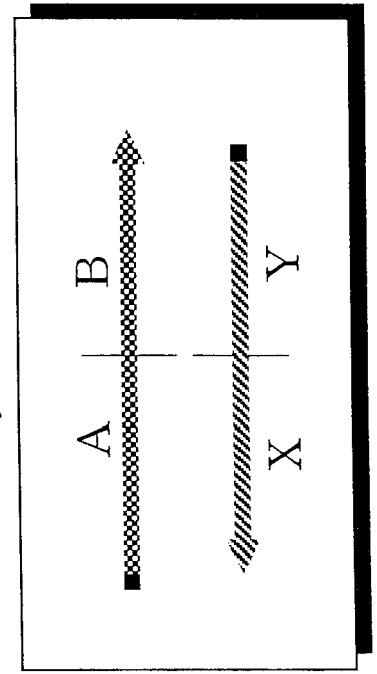
(k) Used as cross-linking probes for formation of a self-assembly substance

FIG. 46

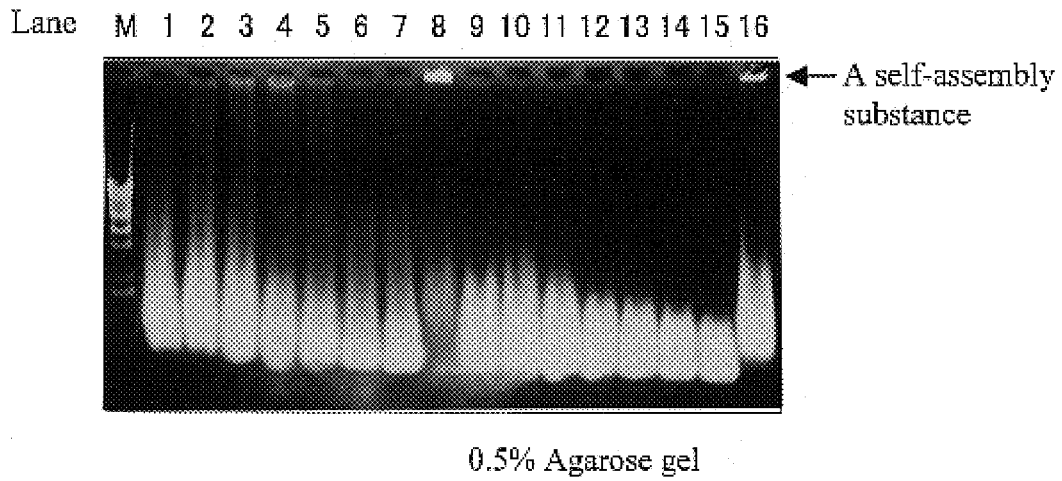

0.5% Agarose gel

Lane M: Molecular size marker
Lane 1: Example 1 ($CaCl_2$ solution, 1.2 M)
Lane 2: Example 2 ($CaCl_2$ solution, 1.0 M)
Lane 3: Example 3 ($CaCl_2$ solution, 0.8 M)
Lane 4: Example 4 ($CaCl_2$ solution, 0.6 M)
Lane 5: Example 5 ($CaCl_2$ solution, 0.4 M)
Lane 6: Example 6 ($CaCl_2$ solution, 0.2 M)
Lane 7: Example 7 ($CaCl_2$ solution, 0.05 M)
Lane 8: Example 15
Lane 9: Example 8 (20 × SSC solution, 1.2 M)
Lane 10: Example 9 (20 × SSC solution, 1.0 M)
Lane 11: Example 10 (20 × SSC solution, 0.8 M)
Lane 12: Example 11 (20 × SSC solution, 0.6 M)
Lane 13: Example 12 (20 × SSC solution, 0.4 M)
Lane 14: Example 13 (20 × SSC solution, 0.2 M)
Lane 15: Example 14 (20 × SSC solution, 0.05 M)
Lane 16: Example 16

FIG. 47
(a) Ligated dimer-forming probes
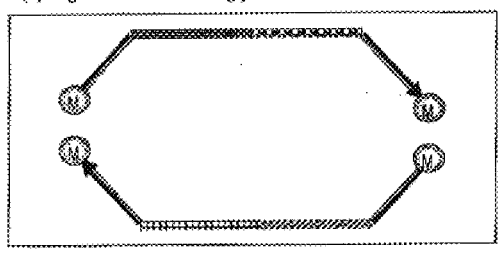
(b) Unreacted dimer-forming probes
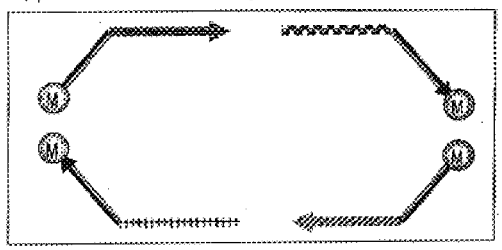
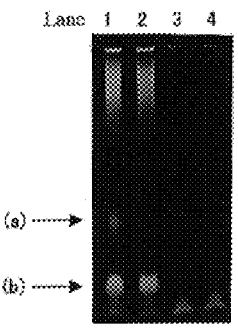
6% PAGE - 7M urea
Lane 1: Example 17, Untreated with an enzyme
Lane 2: Comparative Example 1, Untreated with an enzyme
Lane 3: Example 17, Treated with an enzyme
Lane 4: Comparative Example 1, Treated with an enzyme

FIG. 49
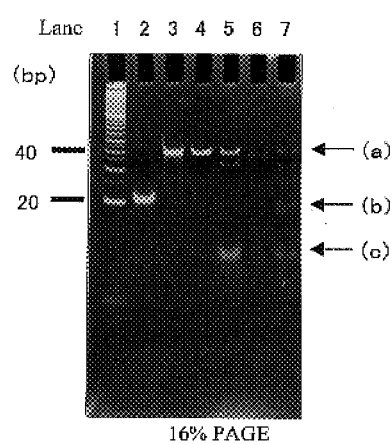
16% PAGE
Lane 1: Molecular size marker
Lane 2: ssDNA of 40 mers
Lane 3: ssDNA of 60 mers
Lane 4: Comparative Example 2,
   Untreated with an enzyme
Lane 5: Example 18,
   Untreated with an enzyme
Lane 6: Comparative Example 2,
   Treated with an enzyme
Lane 7: Example 18,
   Treated with an enzyme
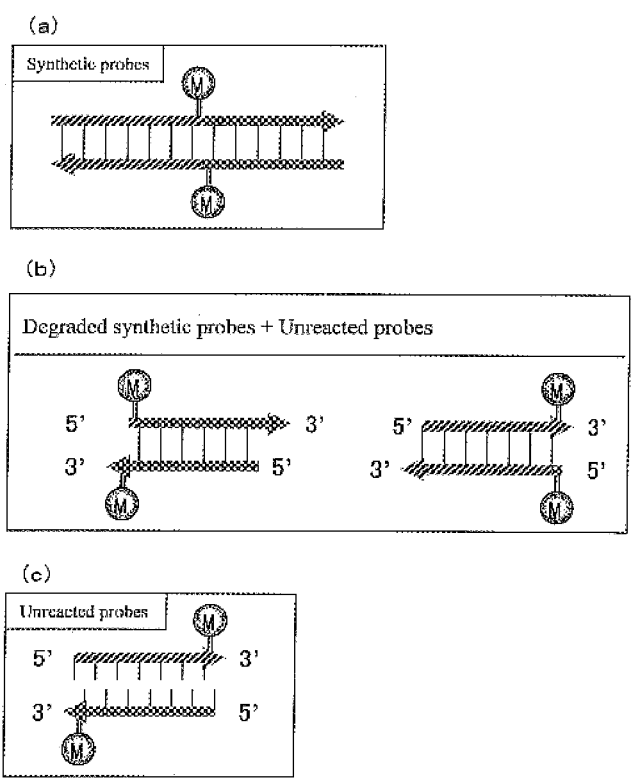

(16% PAGE)

M: DNA Ladder Marker of 10 bp
1: Comparative Example 3
2: Example 19
3: Example 19

SEQUENCE LISTING

```
<160> NUMBER OF SEQ ID NOS: 22

<210> SEQ ID NO 1
<211> LENGTH: 80
<212> TYPE: DNA
<213> ORGANISM: Artificial Sequence
<220> FEATURE:
<223> OTHER INFORMATION: Description of Artificial Sequence: Synthesized
      cross-linking probe-1

<400> SEQUENCE: 1
```

```
ttggatcaac ccgctcaatg cctggagatt tgggcgtgcc cccgcaagac tgctagccga      60
gtagtgttgg gtcgcgaaag                                                  80

<210> SEQ ID NO 2
<211> LENGTH: 80
<212> TYPE: DNA
<213> ORGANISM: Artificial Sequence
<220> FEATURE:
<223> OTHER INFORMATION: Description of Artificial Sequence: Synthesized
      cross-linking probe-2

<400> SEQUENCE: 2
ctttcgcgac ccaacactac tcggctagca gtcttgcggg ggcacgccca aatctccagg      60
cattgagcgg gttgatccaa                                                  80

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthesized
      cross-linking probe-3

<400> SEQUENCE: 3
ttggatcaac ccgctcaatg cctggagatt tgggcgtgcc                            40

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthesized
      cross-linking probe-4

<400> SEQUENCE: 4
ctttcgcgac ccaacactac tcggctagca gtcttgcggg                            40

<210> SEQ ID NO 5
<211> LENGTH: 60
<212> TYPE: DNA
<213> ORGANISM: Artificial Sequence
<220> FEATURE:
<223> OTHER INFORMATION: Description of Artificial Sequence: Synthesized
      dimmer-forming probe-1

<400> SEQUENCE: 5
gtagtgttgg gtcgcgaaag gctcacagtt aagccgtgag cccgcaagac tgctagccga      60

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: Synthesized
      dimmer-forming probe-2

<400> SEQUENCE: 6
cattgagcgg gttgatccaa ctcacggctt aactgtgagc ggcacgccca aatctccagg      60

<210> SEQ ID NO 7
<211> LENGTH: 80
<212> TYPE: DNA
<213> ORGANISM: Artificial Sequence
<220> FEATURE:
<223> OTHER INFORMATION: Description of Artificial Sequence: Synthesized
``` target gene-A

<400> SEQUENCE: 7
aacatgaaaa atgattatgg ctcaggtact gctatccacc ctcaaacagg tgaattatta    60
gcacttgtaa gcacaccttc                                                80

<210> SEQ ID NO 8
<211> LENGTH: 80
<212> TYPE: DNA
<213> ORGANISM: Artificial Sequence
<220> FEATURE:
<223> OTHER INFORMATION: Description of Artificial Sequence: Synthesized
      target gene-B

<400> SEQUENCE: 8
gaaggtgtgc ttacaagtgc taataattca cctgtttgag ggtggatagc agtacctgag    60
ccataatcat ttttcatgtt                                                80

<210> SEQ ID NO 9
<211> LENGTH: 41
<212> TYPE: DNA
<213> ORGANISM: Artificial Sequence
<220> FEATURE:
<221> NAME/KEY: misc_feature
<223> OTHER INFORMATION: methyl group attached at 5'end
<220> FEATURE:
<223> OTHER INFORMATION: Description of Artificial Sequence: Synthesized
      methylated probe-1

<400> SEQUENCE: 9
gtgctgactt aaccggatac gattatggct caggtactgc t                        41

<210> SEQ ID NO 10
<211> LENGTH: 39
<212> TYPE: DNA
<213> ORGANISM: Artificial Sequence
<220> FEATURE:
<221> NAME/KEY: misc_feature
<223> OTHER INFORMATION: phosphoric acid attached at 5'end
<220> FEATURE:
<221> NAME/KEY: misc_feature
<223> OTHER INFORMATION: methyl group attached at 3'end
<220> FEATURE:
<223> OTHER INFORMATION: Description of Artificial Sequence: Synthesized
      methylated probe-2

<400> SEQUENCE: 10
atccaccctc aaacaggtgg attggtactg cgagatagg                           39

<210> SEQ ID NO 11
<211> LENGTH: 40
<212> TYPE: DNA
<213> ORGANISM: Artificial Sequence
<220> FEATURE:
<221> NAME/KEY: misc_feature
<223> OTHER INFORMATION: methyl group attached at 5'end
<220> FEATURE:
<223> OTHER INFORMATION: Description of Artificial Sequence: Synthesized
      methylated probe-3

<400> SEQUENCE: 11
gacgctttct gcgtgtatag cacctgtttg agggtggata                          40

<210> SEQ ID NO 12
<211> LENGTH: 40
<212> TYPE: DNA
<213> ORGANISM: Artificial Sequence
<220> FEATURE:

<221> NAME/KEY: misc_feature
<223> OTHER INFORMATION: phosphoric acid attached at 5'end
<220> FEATURE:
<221> NAME/KEY: misc_feature
<223> OTHER INFORMATION: methyl group attached at 3'end
<220> FEATURE:
<223> OTHER INFORMATION: Description of Artificial Sequence: Synthesized
      methylated probe-4

<400> SEQUENCE: 12
gcagtacctg agccataatc ctagaacgga tcgtacttcg                             40

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Synthesized
      cross-linking probe-5

<400> SEQUENCE: 13
ctatacacgc agaaagcgtc cgaagtacga tccgttctag                             40

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Synthesized
      cross-linking probe-6

<400> SEQUENCE: 14
gtatccggtt aagtcagcac cctatctcgc agtaccattc                             40

<210> SEQ ID NO 15
<211> LENGTH: 20
<212> TYPE: DNA
<213> ORGANISM: Artificial Sequence
<220> FEATURE:
<221> NAME/KEY: misc_feature
<223> OTHER INFORMATION: phosphoric acid attached at 5'end
<220> FEATURE:
<221> NAME/KEY: misc_feature
<223> OTHER INFORMATION: methyl group attached at 3'end
<220> FEATURE:
<223> OTHER INFORMATION: Description of Artificial Sequence: Synthesized
      amplifying probe-1

<400> SEQUENCE: 15
cggaagctcc tatgacaatg                                                   20

<210> SEQ ID NO 16
<211> LENGTH: 20
<212> TYPE: DNA
<213> ORGANISM: Artificial Sequence
<220> FEATURE:
<221> NAME/KEY: misc_feature
<223> OTHER INFORMATION: phosphoric acid attached at 5'end
<220> FEATURE:
<221> NAME/KEY: misc_feature
<223> OTHER INFORMATION: methyl group attached at 3'end
<220> FEATURE:
<223> OTHER INFORMATION: Description of Artificial Sequence Synthesized
      amplifying probe-2

<400> SEQUENCE: 16
gttgatcgtc tcggctagtg                                                   20

<210> SEQ ID NO 17

```
<211> LENGTH: 20
<212> TYPE: DNA
<213> ORGANISM: Artificial Sequence
<220> FEATURE:
<221> NAME/KEY: misc_feature
<223> OTHER INFORMATION: phosphoric acid attached at 5'end
<220> FEATURE:
<223> OTHER INFORMATION: Description of Artificial Sequence: Synthesized
      amplifying probe-3

<400> SEQUENCE: 17
cggaagctcc tatgacaatg                                               20

<210> SEQ ID NO 18
<211> LENGTH: 20
<212> TYPE: DNA
<213> ORGANISM: Artificial Sequence
<220> FEATURE:
<221> NAME/KEY: misc_feature
<223> OTHER INFORMATION: phosphoric acid attached at 5'end
<220> FEATURE:
<223> OTHER INFORMATION: Description of Artificial Sequence: Synthesized
      amplifying probe-4

<400> SEQUENCE: 18
gttgatcgtc tcggctagtg                                               20

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthesized
      dimmer-forming probe-3

<400> SEQUENCE: 19
tatgacaatg gatcctagac cggaagctcc                                    30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthesized
      dimmer-forming probe-4

<400> SEQUENCE: 20
tcggctagtg gtctaggatc gttgatcgtc                                    30

<210> SEQ ID NO 21
<211> LENGTH: 20
<212> TYPE: DNA
<213> ORGANISM: Artificial Sequence
<220> FEATURE:
<221> NAME/KEY: misc_feature
<223> OTHER INFORMATION: phosphoric acid attached at 5'end
<220> FEATURE:
<221> NAME/KEY: misc_RNA
<222> LOCATION: (18)...(20)
<223> OTHER INFORMATION: Combined DNA/RNA
<220> FEATURE:
<223> OTHER INFORMATION: Description of Artificial Sequence: Synthesized
      chimera type amplifying probe-1

<400> SEQUENCE: 21
cggaagctcc tatgacaaug                                               20

<210> SEQ ID NO 22
<211> LENGTH: 20
```

-continued

```
<212> TYPE: DNA
<213> ORGANISM: Artificial Sequence
<220> FEATURE:
<221> NAME/KEY: misc_feature
<223> OTHER INFORMATION: phosphoric acid attached at 5'end
<220> FEATURE:
<221> NAME/KEY: misc_RNA
<222> LOCATION: (18)...(20)
<223> OTHER INFORMATION: Combined DNA/RNA
<220> FEATURE:
<223> OTHER INFORMATION: Description of Artificial Sequence: Synthesized
      chimera type amplifying probe-2

<400> SEQUENCE: 22
gttgatcgtc tcggctagug                                                    20
```

METHOD FOR FORMING SELF-ASSEMBLY SUBSTANCE USING OLIGONUCLEOTIDE SYNTHESIZED BY GENE AMPLIFICATION REACTION, SELF-ASSEMBLY SUBSTANCE AND METHOD FOR DETECTING GENE

This application is a U.S. national stage of International Application No. PCT/JP02/11321 filed Oct. 30, 2002.

TECHNICAL FIELD

The present invention relates to a method for forming a self-assembly substance using oligonucleotides synthesized by a gene amplification reaction, a formed self-assembly substance and a method for detecting a genes with the use thereof.

BACKGROUND ART

In recent years, a variety of gene amplification methods for amplifying a gene aiming at the detection of a trace amount of a target gene have been developed. Of these methods, a Polymerase Chain Reaction method utilizing a thermostable nucleic acid polymerase (U.S. Pat. Nos. 4,683,195, 4,683,202, hereinafter referred to as "PCR"), a Ligase Chain Reaction method utilizing a thermostable nucleic acid ligase (U.S. Pat. No. 5,792,607, hereinafter referred to as "LCR"), a Strand Displacement Amplification method utilizing a nucleic acid polymerase having strand displacement activity (JP 2076096, hereinafter referred to as a "SDA method"), and an Isothermal and Chimeric primer-initiated Amplification of Nucleic acids method (WO 00/56877, hereinafter referred to as an "ICAN method") are gene amplification methods which have been developed taking advantage of characteristics of enzymes synthesizing nucleic acids, respectively.

These gene amplification methods make use of the reaction in which only a specific region of a gene is replicated repetitively, thereby a gene fragment that consists of the specific region is amplified. Accordingly, it is difficult to detect the products amplified by the gene amplification methods in a simple and easy way, because they are linear gene fragments. In the gene detection methods employed in kits for gene diagnosis on the market, a target gene is mainly detected in combination with EIA (enzyme immunoassay) or by previously labeling a gene with a fluorescent substance.

EIA and the measurement in which a gene is labeled with a fluorescent substance, however, need special instruments and reagents, and are complicated in their procedures, requiring more than one hour before judgment. Thus, a simple and inexpensive method for detection of genes amplified by conventional gene amplification methods has been awaited.

On the other hand, the present applicants have already proposed a novel isothermal amplification method of nucleic acid without using an enzyme (a method for forming a self-assembly substance of probes) (U.S. Pat. No. 6,261,846, JP 3267576 and EP 1,002,877A). This method makes use of a pair of probes comprising 3 regions (HoneyComb Probe, hereinafter referred to as an "HCP"), in which a first probe and a second probe are designed such that the 3 regions in each of the probes has base sequences complementary to each other, and when both probes are allowed to react, only one region of the first probe hybridizes to one region of the second probe. This design makes it possible for a plurality of pairs of the probes to hybridize with each other upon reaction and form a self-assembly substance of the probes (Probe alternation link self-assembly reaction, hereinafter referred to as a "PALSAR method").

DISCLOSURE OF THE INVENTION

The present invention has been made in view of the circumstances described above, and the object of the present invention is to provide a method for forming a self-assembly substance using oligonucleotides without using such special instruments and reagents as those required for measurements by EIA, a self-assembly substance formed by the method for forming a self-assembly substance, and a method for detecting an amplified specific gene at a low cost and in a simple way by utilizing the method for forming a self-assembly substance.

In order to solve the above problems, the present inventors have spent much time on research on a variety of methods for forming a self-assembly substance of oligonucleotides. As a result, the present inventors have found to utilize oligonucleotides amplified by a gene amplification reaction as oligonucleotides for the formation of a self-assembly substance. Since the amplified oligonucleotides can readily form a self-assembly substance by a self-assembly reaction, it has been made possible to detect a gene without using any special instruments.

A method for forming a self-assembly substance using oligonucleotides according to the present invention is a method for forming a self-assembly substance of oligonucleotides using a self-assembly reaction of the oligonucleotides, wherein the oligonucleotides comprise oligonucleotides synthesized by a gene amplification reaction.

An example of the method for forming a self-assembly substance described above may comprise the steps of: providing a plurality of pairs of oligonucleotide-probes comprising n (n≧3) base sequence regions (hereinafter sometimes referred to as "HCPs"), each region of a first probe of the pair of probes being complementary to each region of a second probe of the pair of probes; and hybridizing the pairs of oligonucleotide-probes such that the first probes and the second probes cross each other in alternation, wherein the oligonucleotide-probes are self-assembled to form the self-assembly substance.

As at least one of the pairs of the oligonucleotide-probes, there may be used an oligonucleotide which comprises the n (n≧3) regions and is synthesized by the gene amplification reaction.

The above pairs of the oligonucleotide-probes form structures such that the n (n≧3) complementary regions are each necessarily hybridized in a specific manner when one-to-one hybridization of the probes is preformed.

The pairs of the oligonucleotide-probes may comprise m (m≧2) kinds of pairs of probes, the base sequence regions thereof differing in at least one region.

Another example of the method for forming a self-assembly substance described above may comprise the steps of providing n (n≧1) dimer-forming probe-bearing groups formed from a first group to a (2n−1)th group in turn, wherein each group includes a plurality of pairs of dimer-forming probes composed of a pair of an oligonucleotide No. 1 and an oligonucleotide No. 2, each oligonucleotide having 3 regions of a 3' side region, a mid-region and a 5' side region, in which the mid-regions of the oligonucleotides No. 1 and No. 2 have base sequences complementary to each other, and the 3' side regions and 5' side regions thereof have base sequences not complementary to each other, and n (n≧1) cross-linking probe-bearing groups formed from a second group to a 2 nth group in turn, wherein each group includes a plurality of pairs of cross-linking probes composed of a pair of an oligonucleotide No. 1 and an oligonucleotide No. 2, each oligonucleotide having 2 regions of a 3' side region and a 5' side region, in which the 3' side regions and the 5' side regions of the oligonucleotides No. 1 and No. 2 have base sequences not complementary to each other, and the cross-linking probes having base sequences capable of cross-linking dimers formed from the dimer-forming probes; and hybridizing the dimer-forming probes and the cross-linking probes, wherein the oligonucleotides are self-assembled to form the self-assembly substance.

The oligonucleotides synthesized by the gene amplification reaction can be used as at least one of a plurality of pairs of the dimer-forming probes and a plurality of pairs of the cross-linking probes.

In the case of n=1 in the above another example of the method for forming a self-assembly substance, there are two combinations of complementary base sequences between the dimer-forming probes of the first group and the cross-linking probes of the second group. As one example of n=1, base sequences of the above probes to be used are made complementary to each other in the following respective pairs:

the 3' side region of the oligonucleotide No. 1 of the first group and the 3' side region of the oligonucleotide No. 1 of the second group;

the 5' side region of the oligonucleotide No. 2 of the first group and the 5' side region of the oligonucleotide No. 2 of the second group;

the 3' side region of the oligonucleotide No. 2 of the second group and the 3' side region of the oligonucleotide No. 2 of the first group; and the 5' side region of the oligonucleotide No. 1 of the second group and the 5' side region of the oligonucleotide No. 1 of the first group.

As the other example of n=1, base sequences of the above probes to be used are made complementary to each other in the following respective pairs:

the 3' side region of the oligonucleotide No. 1 of the first group and the 3' side region of the oligonucleotide No. 1 of the second group;

the 5' side region of the oligonucleotide No. 2 of the first group and the 5' side region of the oligonucleotide No. 1 of the second group;

the 3' side region of the oligonucleotide No. 2 of the first group and the 3' side region of the oligonucleotide No. 2 of the second group; and the 5' side region of the oligonucleotide No. 1 of the first group and the 5' side region of the oligonucleotide No. 2 of the second group.

In the case of n≧2 in the above another example of the method for forming a self-assembly substance, there are two combinations of complementary base sequences between the dimer-forming probes of 1st, 3rd, . . . and (2n−1)th groups and the cross-linking probes of the 2nd, 4th, . . . and (2n)th groups. As one example of n≧2, base sequences of the above probes to be used are made complementary to each other in the following respective pairs:

the 3' side region of the oligonucleotide No. 1 of the (2n−3)th group and the 3' side region of the oligonucleotide No. 1 of the (2n−2)th group;

the 5' side region of the oligonucleotide No. 2 of the (2n−3)th group and the 5' side region of the oligonucleotide No. 2 of the (2n−2)th group;

the 3' side region of the oligonucleotide No. 2 of the (2n−2)th group and the 3' side region of the oligonucleotide No. 2 of the (2n−1)th group;

the 5' side region of the oligonucleotide No. 1 of the (2n−2)th group and the 5' side region of the oligonucleotide No. 1 of the (2n−1)th group;

the 3' side region of the oligonucleotide No. 1 of the last group for the dimer-forming probes and the 3' side region of the oligonucleotide No. 1 of the last group for the cross-linking probes;

the 5' side region of the oligonucleotide No. 2 of the last group for the dimer-forming probes and the 5' side region of the oligonucleotide No. 2 of the last group for the cross-linking probes;

the 3' side region of the oligonucleotide No. 2 of the last group for the cross-linking probes and the 3' side region of the oligonucleotide No. 2 of the first group; and the 5' side region of the oligonucleotide No. 1 of the last group for the cross-linking probes and the 5' side region of the oligonucleotide No. 1 of the first group.

As the other example of n≧2, base sequences of the above probes to be used are made complementary to each other in the following respective pairs:

the 3' side region of the oligonucleotide No. 1 of the (2n−3)th group and the 3' side region of the oligonucleotide No. 1 of the (2n−2)th group;

the 5' side region of the oligonucleotide No. 2 of the (2n−3)th group and the 5' side region of the oligonucleotide No. 2 of the (2n−2)th group;

the 3' side region of the oligonucleotide No. 2 of the (2n−2)th group and the 3' side region of the oligonucleotide No. 2 of the (2n−1)th group;

the 5' side region of the oligonucleotide No. 1 of the (2n−2)th group and the 5' side region of the oligonucleotide No. 1 of the (2n−1)th group;

the 3' side region of the oligonucleotide No. 1 of the last group for the dimer-forming probes and the 3' side region of the oligonucleotide No. 1 of the last group for the cross-linking probes;

the 5' side region of the oligonucleotide No. 2 of the last group for the dimer-forming probes and the 5' side region of the oligonucleotide No. 1 of the last group for the cross-linking probes;

the 3' side region of the oligonucleotide No. 2 of the last group for the cross-linking probes and the 3' side region of the oligonucleotide No. 2 of the first group; and the 5' side region of the oligonucleotide No. 2 of the last group for the cross-linking probes and the 5' side region of the oligonucleotide No. 1 of the first group.

It is preferable that the hybridizing of the probes comprises the steps of: previously forming dimers from the dimer-forming probes; and thereafter hybridizing the dimers to the cross-linking probes.

The pairs of the dimer-forming probes may comprise m (m≧2) kinds of pairs of dimer-forming probes differing in the mid-regions.

The pairs of the dimer-forming probes may be provided with the same base sequences at the 3' side regions and/or the 5' side regions thereof.

As at least one of the cross-linking probes, there may be used an oligonucleotide which comprises the 2 regions of the cross-linking probes and is synthesized by the gene amplification reaction.

As the oligonucleotides synthesized by the gene amplification reaction, gene fragments complementary to each other may be used, wherein the gene fragments comprise at least 4 regions and include 2 regions complementary to the 5' side region and the 3' side region of the oligonucleotides of the (2n−1)th group, respectively.

The oligonucleotide-probes to be used in the formation of a self-assembly substance such as the HCPs, the dimer-forming probes and the cross-linking probes (hereinafter sometimes generically referred to as probes) may be comprised of at least one base selected from the group consisting of DNA, RNA, PNA and LNA.

At least one G (guanine) or C (cytosine) is arranged at one or more ends of the complementary base sequence regions of the above probes, and when hybridizing the probes, at least one G-C bond is formed at the ends of the complementary base sequence regions, thereby generating a specific interaction by p electrons of bases attributable to stacking of bases, and forming a self-assembly substance of oligonucleotides with higher stability.

As the above oligonucleotides amplified by the gene amplification reaction, those amplified by the gene amplification reaction utilizing a thermostable nucleic acid polymerase may be used firstly.

As the above oligonucleotides amplified by the gene amplification reaction, those amplified by the gene amplification reaction utilizing a thermostable nucleic acid ligase may be used secondly.

As the above oligonucleotides amplified by the gene amplification reaction, those amplified by the gene amplification reaction with a nucleic acid polymerase having strand displacement activity may be used thirdly.

As the above oligonucleotides synthesized by the gene amplification reaction, oligonucleotide fragments comprised of double-stranded DNA and/or RNA may be used.

In addition, as the above oligonucleotides synthesized by the gene amplification reaction, oligonucleotide fragments comprised of single-stranded DNA and/or RNA may be used.

As a probe for amplification used in the gene amplification reaction (hereinafter sometimes referred to as an "amplifying probe"), DNA, RNA or a chimera probe comprised of DNA and RNA may be indicated.

As the amplifying probes used in the gene amplification reaction, it is preferable to use a pair of amplifying probes, at least one of the pair of amplifying probes having a methylated base. The methylated base is located preferably at the 5' end to near the 5' end or at the 3' end to near the 3' end, and more preferably within 5 bases from each end of the amplifying probes. In the present invention, the 5' end and near the 5' end are referred to as a "5' end region", and the 3' end and near the 3' end are referred to as a "3' end region". A pair of amplifying probes may be used, wherein one or both of the pair of probes are methylated. In addition, both of the 5' end region and the 3' end region may be methylated, or either one of the end regions may be methylated. When chimera probes comprised of DNA and RNA are used as the amplifying probes, the end regions of the DNA region and/or RNA region may be methylated, and these probes are also included in the present invention.

As at least one of the oligonucleotides synthesized by the gene amplification reaction, it is preferable to use an oligonucleotide which has region complementary to a sequence of a target gene, the complementary region being previously cleaved and being ligated by a ligation reaction.

The oligonucleotides synthesized by the gene amplification reaction are preferably split by a nuclease.

As the nuclease, it is preferable to use an exonuclease, an RNase H, a restriction enzyme and so on.

A self-assembly substance according to the present invention is formed by the use of the above method for forming a self-assembly substance using oligonucleotides.

A method for detecting a gene according to the present invention comprises the steps of: forming a self-assembly substance by the use of the above method for forming a self-assembly substance using oligonucleotides; and detecting the oligonucleotides synthesized by the gene amplification reaction by detecting the formed self-assembly substance.

Double-stranded DNA and/or RNA may be used as a target gene to be amplified in the gene amplification reaction.

Single-stranded DNA and/or RNA may be used as a target gene to be amplified in the gene amplification reaction.

Single nucleotide polymorphisms may be used as a target gene to be amplified in the gene amplification reaction.

BRIEF DESCRIPTION OF THE DRAWINGS

FIG. 7 is a schematic diagram showing in principle a first embodiment of a first example of the method for forming a self-assembly substance using oligonucleotides according to the present invention, where (a) shows a pair of gene fragments, (b) shows a pair of dimer-forming probes, and (c) shows formation of a self-assembly substance, respectively;

FIG. 8 is a schematic diagram showing in principle a second embodiment of the first example of the method for forming a self-assembly substance using oligonucleotides according to the present invention, where (a) shows a pair of gene fragments, (b) shows a pair of dimer-forming probes, and (c) shows formation of a self-assembly substance, respectively;

FIG. 9 is a schematic diagram showing in principle a third embodiment of the first example of the method for forming a self-assembly substance using oligonucleotides according to the present invention, where (a) shows a pair of gene fragments, (b) shows a pair of dimer-forming probes, and (c) shows formation of a self-assembly substance, respectively;

FIG. 10 is a schematic diagram showing in principle a 4th embodiment of the first example of the method for forming a self-assembly substance using oligonucleotides according to the present invention, where (a) shows a pair of gene fragments, (b) shows a pair of dimer-forming probes, and (c) shows formation of a self-assembly substance, respectively;

FIG. 11 is a schematic diagram showing the first example of the method for forming a self-assembly substance by using a pair of gene fragments cleaved by an enzyme, where (a) shows a pair of gene fragments, (b) shows a pair of dimer-forming probes, and (c) shows formation of a self-assembly substance, respectively;

FIG. 12 is a schematic diagram showing a second example of the method for forming a self-assembly substance by using a pair of gene fragments cleaved by an enzyme, where (a) shows a pair of gene fragments, (b) shows a pair of dimer-forming probes, and (c) shows formation of a self-assembly substance, respectively;

FIG. 13 is a schematic diagram showing a third example of the method for forming a self-assembly substance by using a pair of gene fragments cleaved by an enzyme, where (a) shows a pair of gene fragments, (b) shows a pair of dimer-forming probes, and (c) shows formation of a self-assembly substance, respectively;

FIG. 14 is a schematic diagram showing the method for forming a self-assembly substance using a gene fragment and a cross-linking probe prepared in advance, where (a) shows a single-stranded gene fragment, (b) shows a pair of dimer-forming probes, (c) shows a cross-linking probe prepared in advance, and (d) shows formation of a self-assembly substance, respectively;

FIG. 16 is a schematic diagram showing the example of the method for forming a self-assembly substance using gene fragments amplified by gene amplification with the use of amplifying probes of RNA and the RNase H, where (b) shows a pair of gene fragments amplified with amplifying probes of RNA, (c) shows the pair of gene fragments after treatment with the RNase H, (d) shows a pair of dimer-forming probes, and (e) shows formation of a self-assembly substance, respectively;

FIG. 17 shows methylated bases of the oligonucleotides used in the present invention;

FIG. 19 is a schematic diagram showing in principle the embodiment of the second example of the method for forming a self-assembly substance using oligonucleotides according to the present invention, where (c) shows hybridization of the cleaved dimer-forming probes with the target gene and (d) shows a ligation reaction of the cleaved dimer-forming probes, respectively;

FIG. 20 is a schematic diagram showing in principle the embodiment of the second example of the method for forming a self-assembly substance using oligonucleotides according to the present invention, where (e) shows treatment of the ligated dimer-forming probes with a nuclease and (f) shows treatment of the unreacted dimer-forming probes with a nuclease, respectively;

FIG. 24 is a schematic diagram showing in principle the first embodiment of the third example of the method for forming a self-assembly substance using oligonucleotides according to the present invention, where (e) shows hybridization of the amplifying probes with the synthesized DNA and (f) shows DNA synthesis, respectively;

FIG. 25 is a schematic diagram showing in principle the first embodiment of the third example of the method for forming a self-assembly substance using oligonucleotides according to the present invention, where (g) shows synthetic probes and (h) shows degradation by a nuclease, respectively;

FIG. 26 is a schematic diagram showing in principle the first embodiment of the third example of the method for forming a self-assembly substance using oligonucleotides according to the present invention, where (i) shows the synthetic probes split by the nuclease, (j) shows usage of the synthetic probes as cross-linking probes, and (k) shows usage of the synthetic probes as HCPs, respectively;

FIG. 29 is a schematic diagram showing in principle the second embodiment of the third example of the method for forming a self-assembly substance using oligonucleotides according to the present invention, where (c) shows hybridization of the amplifying probes with the target genes and (d) shows DNA synthesis, respectively;

FIG. 31 is a schematic diagram showing in principle the second embodiment of the third example of the method for forming a self-assembly substance using oligonucleotides according to the present invention, where (g) shows synthetic probes and (h) shows degradation by a nuclease, respectively;

FIG. 32 is a schematic diagram showing in principle the second embodiment of the third example of the method for forming a self-assembly substance using oligonucleotides according to the present invention, where (i) shows the synthetic probe split by the nuclease, (j) shows usage of the synthetic probe as a cross-linking probe, and (k) shows usage of the synthetic probe as HCP, respectively;

FIG. 33 is a schematic diagram showing in principle the second embodiment of the third example of the method for forming a self-assembly substance using oligonucleotides according to the present invention, where (l) shows hybridization of the unreacted probe with the split synthetic probe and (m) shows treatment with a nuclease, respectively;

FIG. 37 is a schematic diagram showing in principle the embodiment of the 4th example of the method for forming a self-assembly substance using oligonucleotides according to the present invention, where (h) shows the synthetic probes and (i) shows degradation by a nuclease, respectively;

FIG. 38 is a schematic diagram showing in principle the embodiment of the 4th example of the method for forming a self-assembly substance using oligonucleotides according to the present invention, where (h) shows the synthetic probes split by the nuclease, (k) shows usage of the synthetic probes as cross-linking probes, and (l) shows the synthetic probes as HCPs, respectively;

FIG. 43 is a schematic diagram showing in principle the embodiment of the 5th example of the method for forming a self-assembly substance using oligonucleotides according to the present invention, where (h) shows the synthetic probes and (i) shows degradation by a nuclease, respectively;

FIG. 44 is a schematic diagram showing in principle the embodiment of the 5th example of the method for forming a self-assembly substance using oligonucleotides according to the present invention, where (j) shows the synthetic probes split by the nuclease, (k) shows usage of the synthetic probes as cross-linking probes, and (l) shows usage of the synthetic probes as HCPs, respectively;

FIG. 46 is a photograph showing the results of Examples 1 to 16;

FIG. 47 is a photograph showing the results of denaturing PAGE of Example 17 and Comparative Example 1;

FIG. 49 is a photograph showing the results of PAGE of Example 18 and Comparative Example 2;

BEST MODE FOR CARRYING OUT THE INVENTION

Several embodiments of the present invention will be described hereinafter with reference to the accompanying drawings. It goes without saying, however, that these embodiments are merely illustrative, and a variety of modifications may be made without, departing from the spirit and scope of the present invention.

The present invention relates to forming a double-stranded self-assembly substance by carrying out a self-assembly reaction using oligonucleotides synthesized by a gene amplification method, under isothermal conditions in the absence of any enzymes.

The number of probes to be used is not particularly limited, but is generally used in the range of from $10^2$ to $10^{15}$. The composition and the concentration of a buffer solution used for reaction are not particularly limited, and conventional buffer solutions used for nucleic acid amplification may be preferably used. The pH may be also suitable in the common range, and preferably in the range of from pH 7.0 to pH 9.0.

The reaction temperature ranges from 40° C. to 90° C., and preferably ranges from 55° C. to 70° C. These conditions are not particularly limited.

The nucleic acids constituting probes are generally composed of DNA or RNA, and nucleic acid analogs are also usable. These analogs of nucleic acids include, for example, Peptide Nucleic Acids (PNA, WO 92/20702), and Locked Nucleic Acid (LNA, Koshkin A A et al. Tetrahedron 1998. 54, 3607-3630. Koshkin A A et al. J. Am. Chem. Soc. 1998. 120, 13252-13253. Wahlestedt C et al. PNAS 2000. 97, 5633-5638.). The probes are composed of the same kind of nucleic acids in general, while a pair of a DNA probe and an RNA probe may also be usable. In other words, the kinds of nucleic acids for use in the probes may be selected from DNA, RNA and analogs of nucleic acids (for example, PNA, LNA and the like). Further, nucleic acids in one probe may not be necessarily composed of one kind of nucleic acid, for example, only DNA. A probe (a chimera probe) composed of different kinds, e.g. DNA and RNA may be used, if necessary, and this kind of probe is also included in the scope of the present invention.

In addition, the length of each region of the probes is at least 5 bases, preferably at least 8 bases, more preferably 10 to 100 bases, and furthermore preferably 10 to 40 bases in terms of the number of bases.

The above gene amplification method is not particularly limited, and double-stranded or single-stranded DNA and/or RNA amplified by a known gene amplification method, for example, the PCR method, the SDA method, the ICAN method, an NASBA method, a TMA method, a 3SR method, the LCR method and the like may be used as oligonucleotides for the self-assembly reaction.

Figure 1:
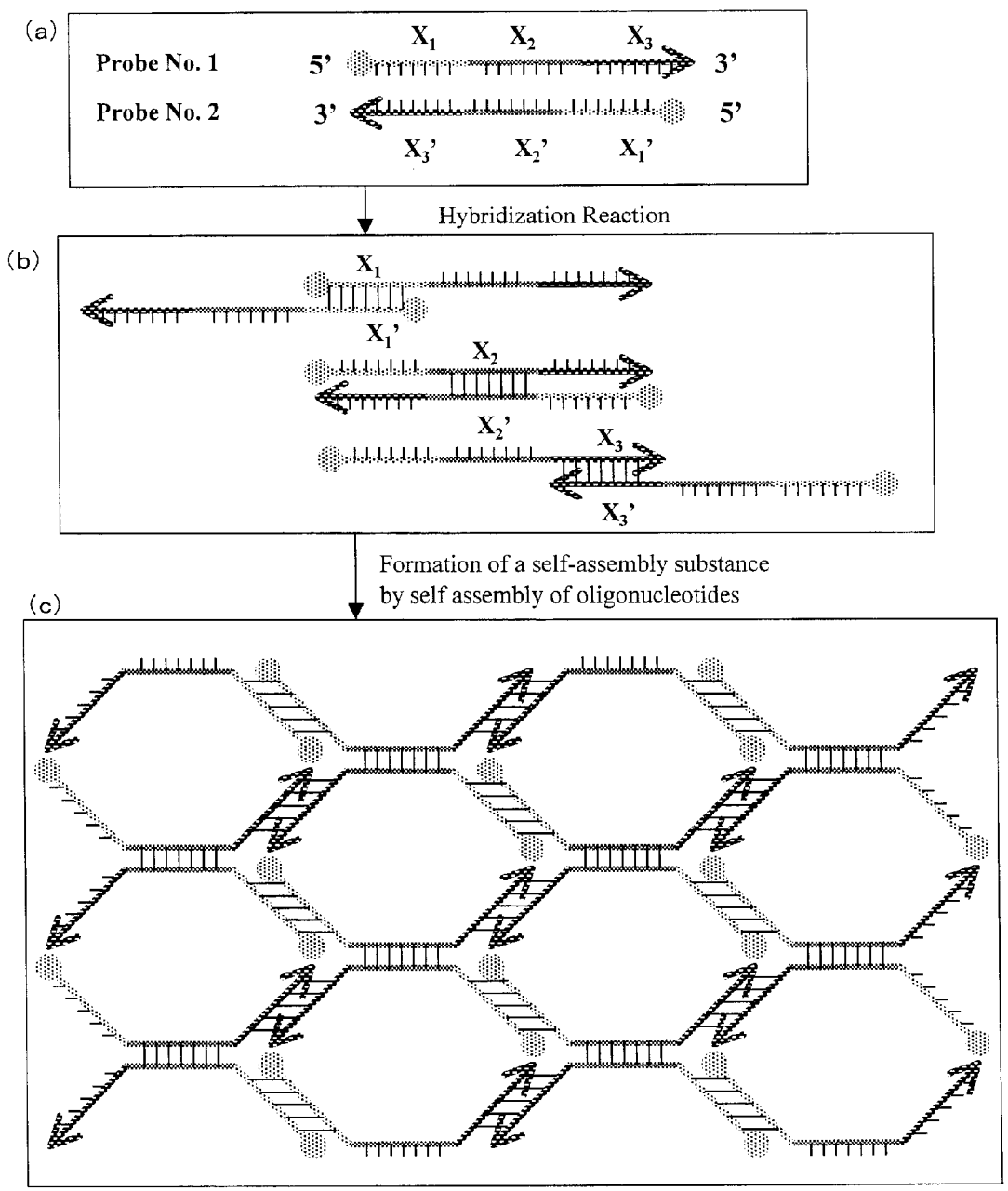
FIG. 1 is a schematic diagram showing an example of the method for forming a self-assembly substance by using a pair of HCPs according to the PALSAR method used in the present invention, where (a) shows a pair of HCPs, (b) shows an example showing how the HCPs are bound, and (c) shows formation of a self-assembly substance, respectively.

FIG. 1 is a schematic diagram showing an example of the method for forming a self-assembly substance according to the PALSAR method, in which a pair of HCPs (No. 1 and No. 2 probes) is used. In FIG. 1, the No. 1 probe comprises an $X_1$ region, an $X_2$ region and an $X_3$ region, and the No. 2 probe comprises an $X_1'$ region, an $X_2'$ region and an $X_3'$ region [FIG. 1(a)]. The No. 1 probe and the No. 2 probe are structured such that when they are hybridized, the $X_1$ region is bound only to the $X_1'$ region, the $X_2$ region is bound only to the $X_2'$ region, and the $X_3$ region is bound only to the $X_3'$ region, so that the pair of the probes are hybridized in alternation in 3 binding patterns [FIG. 1(b)].

A plurality of pairs of the HCPs, which have been hybridized in alternation in the 3 binding patterns, are able to form a double-stranded self-assembly substance by self-assembly of the oligonucleotides according to the principle of the PALSAR method, one example of which is schematically illustrated in FIG. 1(c).

FIG. 1 illustrates an example using HCPs comprising 3 complementary base sequence regions; Further, a self-assembly substance may also be formed in a similar way when HCPs having 4 or more complementary base sequence regions are used.

Figure 2:
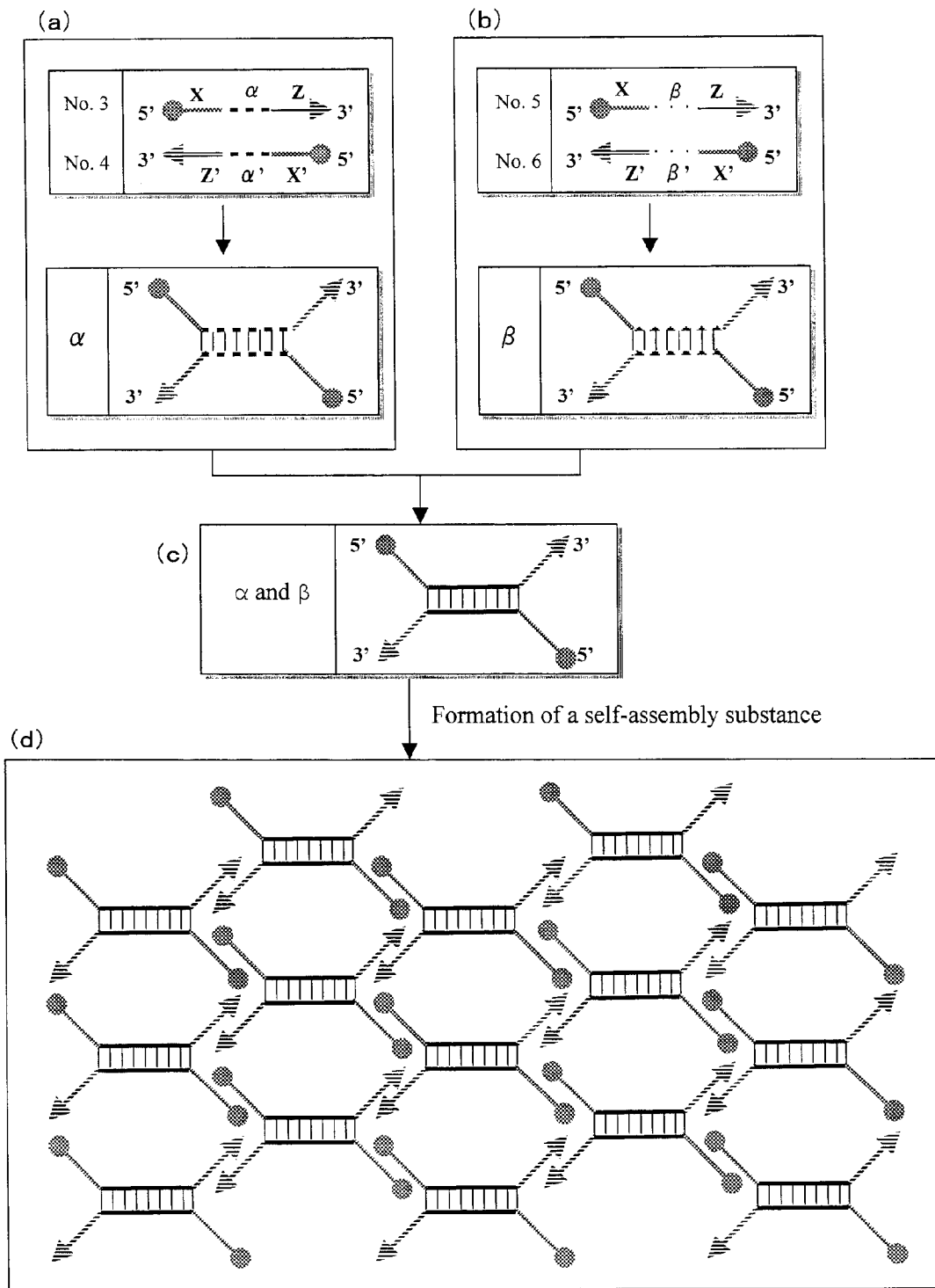
FIG. 2 is a schematic diagram showing another example of the method for forming a self-assembly substance by using a pair of HCPs according to the PALSAR method used in the present invention, where (a) and (b) each shows a pair of HCPs differing from each other in one complementary region thereof, (c) shows a dimer formed from the above HCPs, and (d) shows formation of a self-assembly substance, respectively.

In the method for forming a self-assembly substance by using HCPs above described, 2 or more sets of HCPs having different complementary regions may be used. FIG. 2 shows an example of the method for detecting a self-assembly substance formed from 2 different pairs of HCPs (No. 3 and No. 4 probes; No. 5 and No. 6 probes) comprising 3 complementary regions in each pair. In FIG. 2, the No. 3 probe comprises an X region, an α region and a Z region, and the No. 4 probe comprises an X' region, an α' region and a Z' region [FIG. 2(a)]. And the No. 5 probe comprises the X region, a β region and the Z region, and the No. 6 probe comprises the X' region, a β' region and the Z' region [FIG. 2(b)]. As illustrated in FIG. 2, the 2 sets of HCPs differ in one complementary region. These probes are structured such that when they are hybridized with each other, the X region is bound only to the X' region, the Z region is bound only to the Z' region, the α region is bound only to the α' region, and the β region is bound only to the β' region. 2 sets of HCPs may form dimers by hybridization of the α region with the α' region or the β region with the β' region, respectively. And these dimers [FIG. 2(c)] may form a double-stranded self-assembly substance by self-assembly of the oligonucleotides according to the principle of the PALSAR method [FIG. 2(d)].

Figure 3:
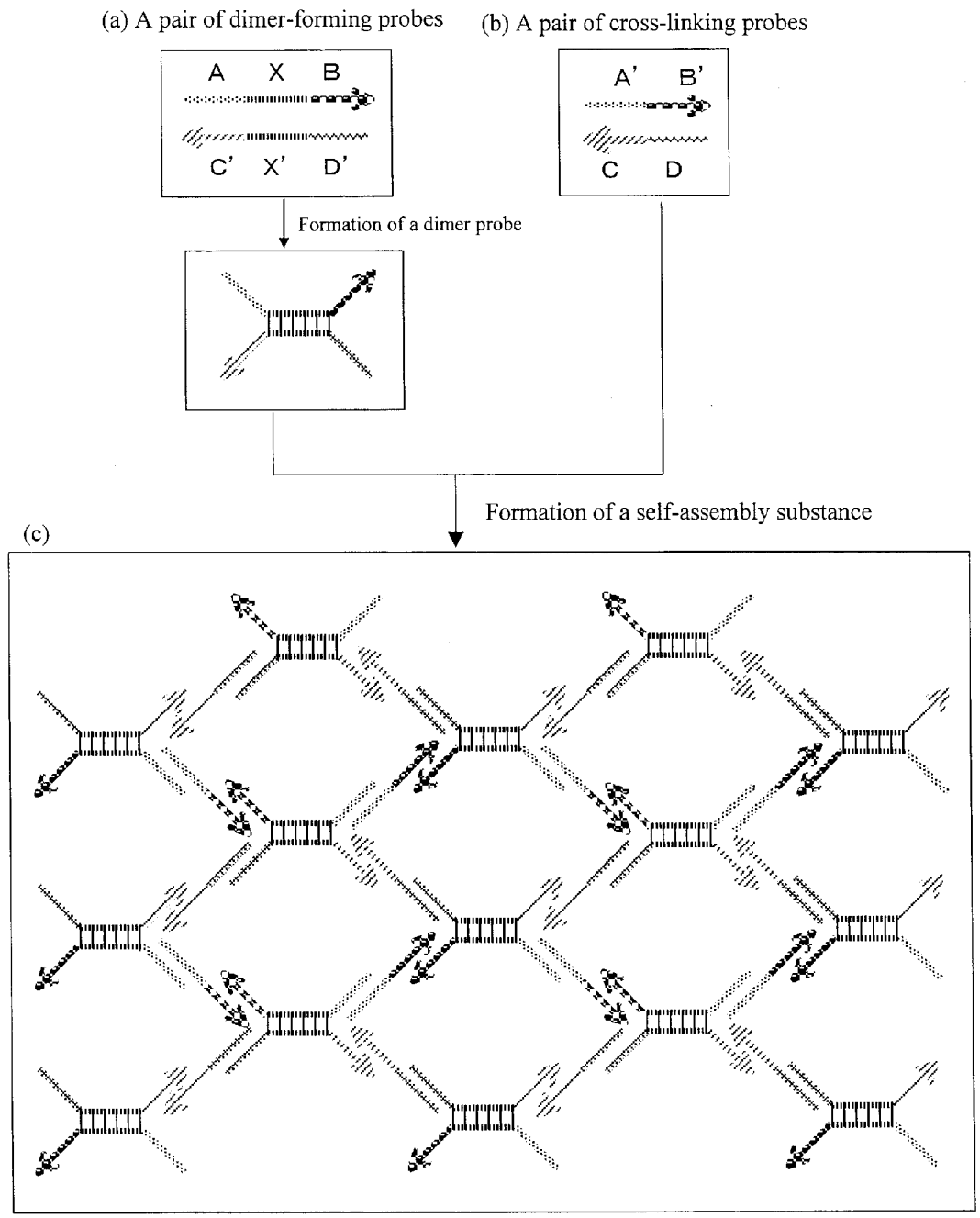
FIG. 3 is a schematic diagram showing an example of the method for forming a self-assembly substance by using dimer-forming probes and cross-linking probes in the case of n=1 according to the PALSAR method used in the present invention, where (a) shows a pair of dimer-forming probes, (b) shows a pair of cross-linking probes, and (c) shows formation of a self-assembly substance, respectively.

FIG. 3 is a schematic diagram showing an example of the method for forming a self-assembly substance according to the PALSAR method, in which dimer-forming probes and cross-linking probes are used. As shown in FIG. 3, a pair of dimer-forming probes of a first group composed of a pair of oligonucleotides, forms a dimer-probe, each oligonucleotides being divided into 3 regions, in which the mid-regions thereof are complementary to each other, and the 3' side regions and the 5' side regions thereof are non-complementary base sequences to each other [FIG. 3(a)]. A pair of the cross-linking probes of a second group is composed of a pair of oligonucleotides, each oligonucleotide being divided into 2 regions, in which the 3' side region and the 5' side region thereof are non-complementary base sequences to each other, while the 3' side regions are complementary base sequences with the 3' side regions of the dimer-forming probes, and the 5' side regions are complementary base sequences with the 5' side regions of the dimer-forming probes, respectively [FIG. 3(b)]. The oligonucleotides are self-assembled to form a double-stranded self-assembly substance by hybridizing the cross-linking probes of the second group to the dimer-probes of the first group so that they crosslink [FIG. 3(c)].

Figure 4:
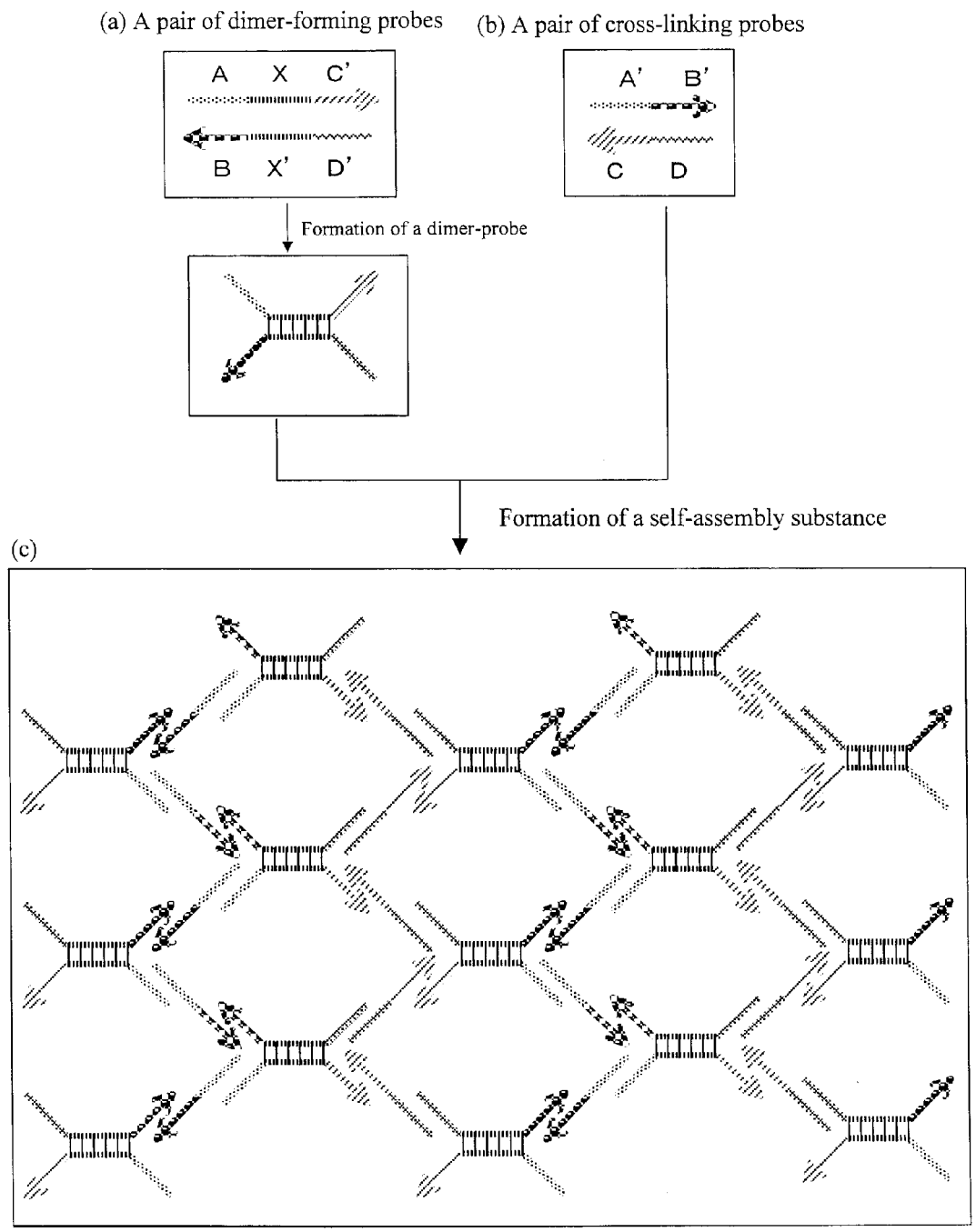
FIG. 4 is a schematic diagram showing another example of the method for forming a self-assembly substance by using dimer-forming probes and cross-linking probes in the case of n=1 according to the PALSAR method used in the present invention, where (a) shows a pair of dimer-forming probes, (b) shows a pair of cross-linking probes, and (c) shows formation of a self-assembly substance, respectively.

FIG. 4 is a schematic diagram showing another example of the method for forming a self-assembly substance according to the PALSAR method, in which dimer-forming probes and cross-linking probes are used. The combination of complementary regions of the 5' side regions and the 3' side regions of the dimer-forming probes and the cross-linking probes is alterable from the combination shown in FIG. 3 to that as shown in FIG. 4.

Figure 5:
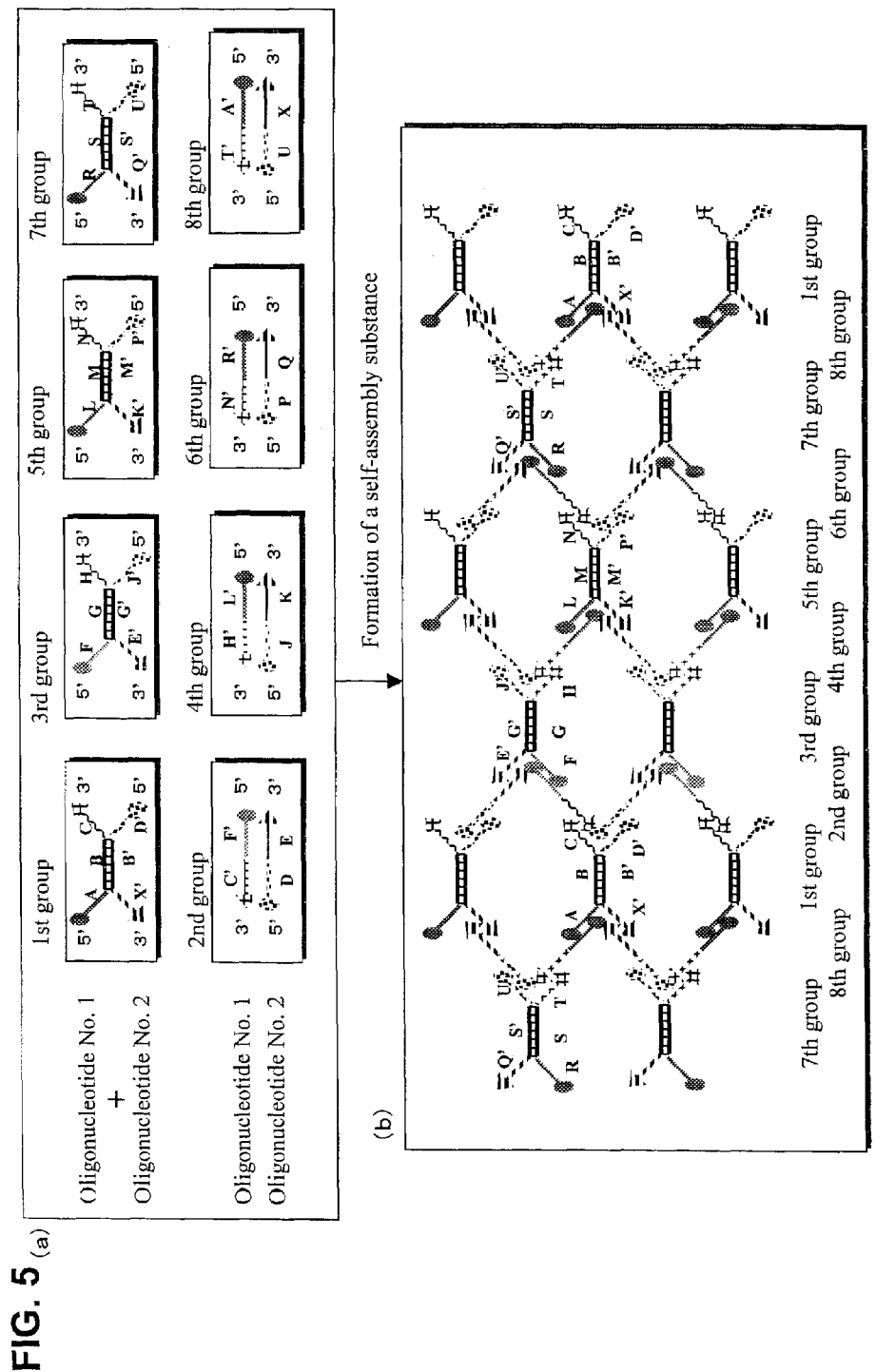
FIG. 5 is a schematic diagram showing an example of the method for forming a self-assembly substance by using dimer-forming probes and cross-linking probes in the case of n≧2 according to the PALSAR method used in the present invention, where (a) shows 4 sets of dimer-probes formed from a pair of dimer-forming probes and 4 sets of a pair of cross-linking probes, and (b) shows formation of a self-assembly substance, respectively.
Figure 6:
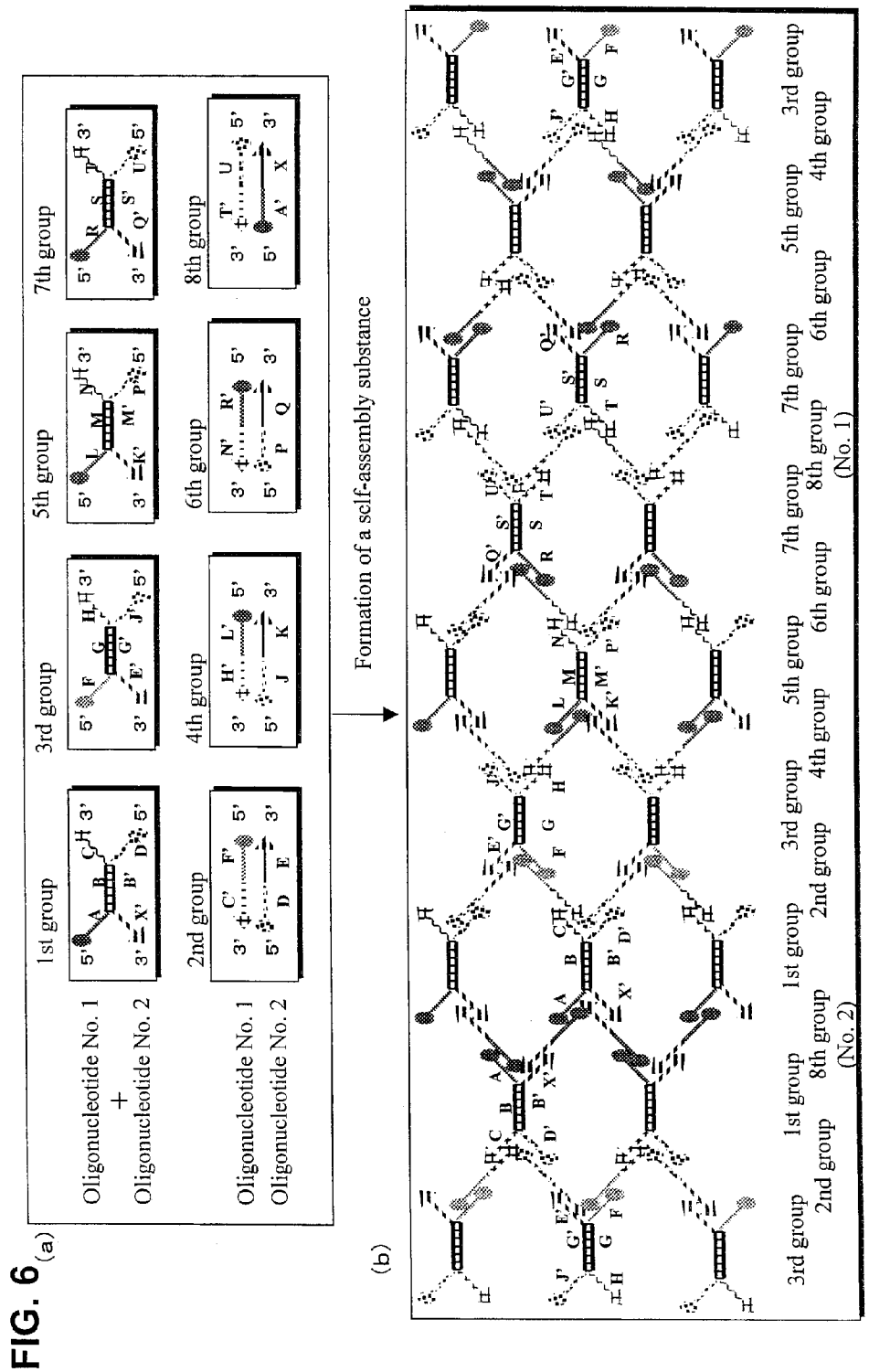
FIG. 6 is a schematic diagram showing another example of the method for forming a self-assembly substance by using dimer-forming probes and cross-linking probes in the case of n≧2 according to the PALSAR method used in the present invention, where (a) shows 4 sets of dimer-probes formed from a pair of dimer-forming probes and 4 sets of a pair of cross-linking probes, and (b) shows formation of a self-assembly substance, respectively.

The method for forming a self-assembly substance by using the dimer-forming probes composed of the first group and the cross-linking probes composed of the second group is explained in FIGS. 3 and 4, while it is also possible to form a self-assembly substance by using dimer-forming probes composed of 1, 3, . . . (2n–1)th groups and cross-linking probes composed of 2, 4, . . . 2nth group, as shown in FIGS. 5 and 6. FIG. 5 is a schematic diagram showing an example of the method for forming a self-assembly substance in the case of n≧2. FIG. 6 is a schematic diagram showing another example of the method for forming a self-assembly substance in the case of n≧2.

In the above method for forming a self-assembly substance by using the dimer-forming probes and the cross-linking probes, the non-complementary base sequences are not limited but base sequences which do not hybridize with each other, and the same base sequences are also included in the non-complementary base sequences.

The above dimer-forming probes may be composed of one kind of dimer-forming probes in each group or may comprise several kinds of dimer-forming probes, the mid-regions thereof being different from each other, which is not particularly limited. Furthermore, it is possible to use 2 or more sets of dimer-forming probes and cross-linking probes at the same time, where these sets are completely free from complementation to each other.

In the method for forming a self-assembly substance by using the dimer-forming probes and the cross-linking probes described above, the time for forming the dimer from the dimer-forming probes is not specially limited, the dimer-forming probes before the dimer formation are allowed to react with the cross-linking probes at the same time, or the dimer-forming probes are allowed to form dimers in advance, and thereafter react with the cross-linking probes. It is more preferable to form a self-assembly substance by previously forming the dimers and then reacting the dimers with the cross-linking probes.

The method for forming a self-assembly substance of oligonucleotides according to the present invention make use of at least one oligonucleotide synthesized by a gene amplification reaction as a probe in the method for forming a self-assembly substance above-described.

A first example of the method for forming a self-assembly substance using oligonucleotides synthesized by a gene amplification method according to the present invention makes use of a gene as a probe in the PALSAR method, wherein the gene is amplified by a conventional gene amplification method, for example, the method making use of a thermostable nucleic acid polymerase, nucleic acid polymerase having strand displacement activity or the like. The following will describe the cases in which amplified genes are used as cross-linking probes:

FIG. 7 is a schematic diagram showing in principle a first embodiment of the first example of the method for forming a self-assembly substance using oligonucleotides described above. As shown in FIG. 7, a self-assembly substance may be formed using a pair of gene fragments complementary to each other which are amplified by a conventional gene amplification method. First, the gene fragments complementary to each other are divided into 4 regions (A to D regions and A' to D' regions), as shown in FIG. 7(a). Next, 2 regions (the A region and the B region, or the C' region and the D' region) on the 5' side of the pair of the oligonucleotides are selected for each oligonucleotide, respectively. Of the selected two regions, one region (the A region or the D' region) each located on the 5' side is used for the 5' side region of the cross-linking probes, while the other region (the B region or the C' region) located on the 3' side is used for the 3' side region of the cross-linking probes, thereby preparing a pair of corresponding dimer-forming probes as shown in FIG. 7(b). Though an extra sequence (the C region and the D region, or the A' region and the B' region, hereinafter also referred to as a "tag") that does not hybridize with any regions of the dimer-forming probes exists in each 3' side region of the gene fragments, the pair of the gene fragments hybridizes to the dimer-probe formed from the pair of the dimer-forming probes so as to cross-link the dimer-probes, and according to the principle of the PALSAR method, the oligonucleotides are self-assembled to form a double-stranded self-assembly substance [FIG. 7(c)].

FIG. 8 is a schematic diagram showing in principle a second embodiment of the first example of the method for forming a self-assembly substance using oligonucleotides described above. As shown in (a) and (b) of FIG. 8, 2 regions (the C region and the D region, or the A' region and the B' region) on the 3' side of each pair of the gene fragments may be used for the 5' side region and the 3' side region of a pair of the cross-linking probes. In this case, an extra sequence (the A region and the B region, or the C' region and the D' region) that does not hybridize with any regions of the dimer-forming probes exists in each 5' side region of the gene fragments. The pair of the gene fragments hybridizes to the dimer-probe formed from the pair of the dimer-forming probes so as to cross-link the dimer-probes, and according to the principle of the PALSAR method, the oligonucleotides are self-assembled to form a double-stranded self-assembly substance [FIG. 8(c)].

FIG. 9 is a schematic diagram showing in principle a third embodiment of the first example of the method for forming a self-assembly substance using oligonucleotides described above. As shown in (a) and (b) of FIG. 9, two unadjacent regions (the A region and the B region, or the D' region and the C' region) of a pair of the gene fragments may be used for the 5' side region and the 3' side region of a pair of the cross-linking probes, respectively. In this case as well, the pair of the gene fragments hybridizes to the dimer-probe formed from the pair of the dimer-forming probes so as to cross-link the dimer-probes, and according to the principle of the PALSAR method, the oligonucleotides are self-assembled to form a double-stranded self-assembly substance, as shown in FIG. 9(c).

In addition, a pair of gene fragments amplified by a conventional gene amplification method may be divided into 5 regions, of which 2 regions may be used as 2 regions to cross-link dimer-probes, respectively.

FIG. 10 is a schematic diagram showing in principle a 4th embodiment of the first example of the method for forming a self-assembly substance using oligonucleotides described above. As shown in FIG. 10(a), gene fragments complementary to each other are divided into 5 regions (A to E regions or A' to E' regions). Further, 2 regions (the A region and the B region, or the C' region and the D' region) on the 5' side of the pair of the oligonucleotides are selected for each oligonucleotide, respectively. Of the selected 2 regions, one region (the A region or the D' region) located on the 5' side is used for the 5' side region of the cross-linking probes, while the other region (the B region or the C' region) located on the 3' side is used for the 3' side region of the cross-linking probes, thereby preparing a pair of corresponding dimer-forming probes, as shown in FIG. 10(b). An extra sequence (the E, C and D regions, or the A', B' and E' regions) which does not hybridize with any regions of the dimer-forming probes exists in each 3' side region of the gene fragments, but the pair of the gene fragments hybridizes to the dimer-probe formed from a pair of the dimer-forming probes so as to cross-link the dimer-probes, and according to the principle of the PALSAR method, the oligonucleotides are self-assembled to form a double-stranded self-assembly substance [FIG. 10(c)].

As described above, a pair of complementary gene fragments may be used as cross-linking probes for the PALSAR method. Of the regions in the gene fragments, any 2 regions may be selected for regions hybridizing to the dimer-probe. It is not particularly defined whether the 2 regions are adjacent to or separated from each other. In addition, they may not necessarily be located at the end of the gene fragments.

In the method for forming a self-assembly substance using oligonucleotides according to the present invention, it is preferable to previously cleave the gene fragments amplified by a conventional gene amplification reaction with an enzyme or the like to cut off a region not complementary to the dimer-forming probes, and thereafter to form a self-assembly substance by using the pair of the gene fragments cleaved as the cross-linking probes according to the principle of the PALSAR method.

A method for forming a self-assembly substance using cleaved gene fragments is shown in FIGS. 11 to 13. FIGS. 11 and 12 show the method for forming a self-assembly substance, in which the pairs of the gene fragments in FIGS. 7 and 10 are cleaved, respectively. FIG. 13 shows the method for forming a self-assembly substance using a pair of cleaved gene fragments, in which the complementary regions between the dimer-forming probes and the cross-linking probes are made to have the combination shown in FIG. 4. It is possible to increase the efficiency in forming a self-assembly substance by cleaving extra regions which do not cross-link to the dimer-probes.

The method for cleaving the gene fragments is not particularly limited and it is preferable to use an enzyme, for example, a restriction enzyme, an RNase H, or the like.

In the method for forming a self-assembly substance using oligonucleotides according to the present invention, the time for forming a dimer from the dimer-forming probes is not specially limited, the dimer-forming probes before dimer formation are allowed to react with gene fragments at the same time, or the dimer-forming probes are allowed to form a dimer-probe in advance, and thereafter react with the gene fragments. It is more preferable to form the dimer-probe in advance and then form a self-assembly substance.

The method for forming a self-assembly substance using oligonucleotides according to the present invention include a method for forming a self-assembly substance in which a dimer-probe similar to the dimer-probe formed from the above dimer-forming probes is hybridized to the cross-linking probes so that they cross-link, thereby forming a self-assembly substance.

It is not necessary for a pair of the gene fragments, used in the method for forming a self-assembly substance using oligonucleotides according to the present invention, to be gene fragments in which both are amplified by a gene amplification reaction. As shown in FIG. 14, for example, in the pair of gene fragments used as the cross-linking probes, one of them may be a gene fragment amplified by a conventional amplification method [FIG. 14(a)] and the other may be a gene fragment prepared in advance [FIG. 14(c)]. A self-assembly substance is formed by hybridizing the pair of gene fragments to their corresponding pair of the dimer-forming probes [FIG. 14(b)] [FIG. 14(d)]. As described above, the gene fragments used are not particularly limited as long as they contain two regions which can hybridize so as to cross-link to the dimer-probes, respectively. As a preferable example, FIG. 14(a) shows a single-stranded gene fragment having A and B regions, each region capable of cross-linking to the dimer-probe, and a Y region incapable of hybridizing to the dimer-probe. The Y region may have any sequence and is not particularly limited. As described above, the gene fragments containing an extra tag may be used as they are, but it is more preferable to cleave the region and thereafter form a self-assembly substance.

Figure 15:
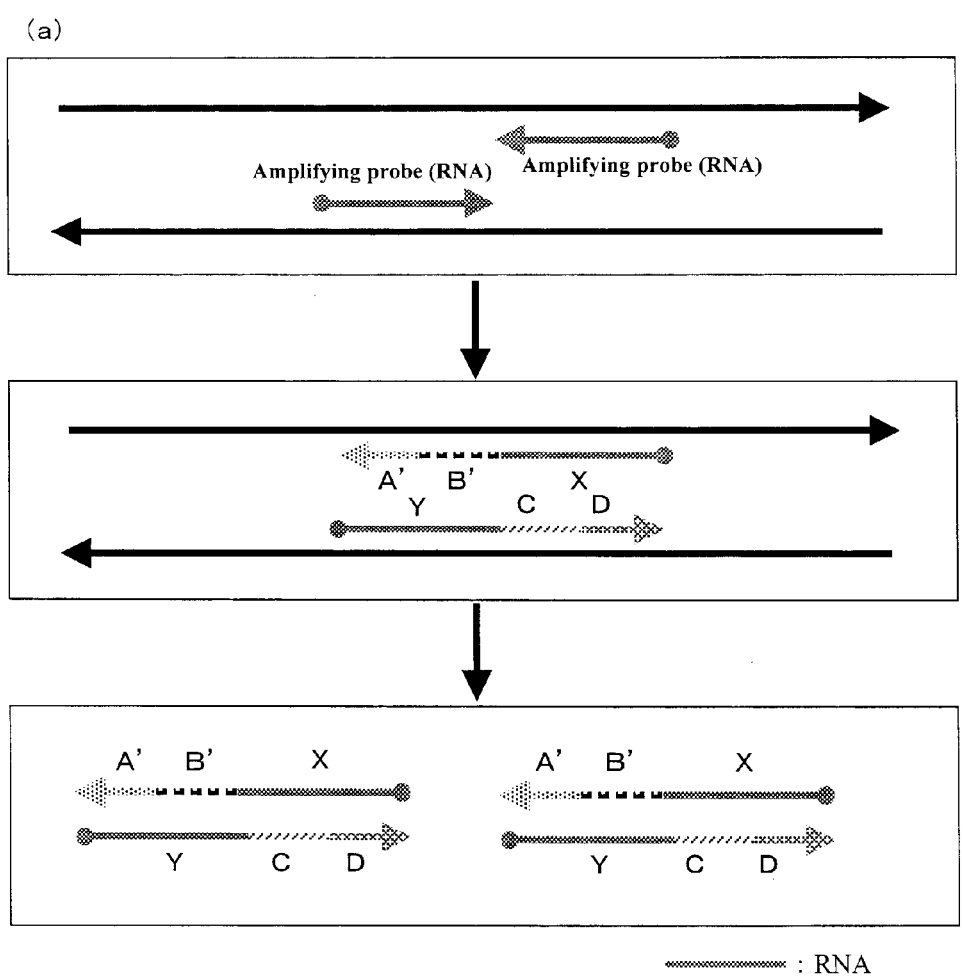
FIG. 15 is a schematic diagram showing an example of the method for forming a self-assembly substance using gene fragments amplified by gene amplification with the use of amplifying probes of RNA and an RNase H, where (a) shows amplification of DNA with the use of amplifying probes of RNA.

The conventional gene amplification methods make gene amplification using a large excess of amplifying probes such as a primer, therefore the solution contains an excess of amplifying probes as well as the amplified gene fragments after amplification. Problems such as a decline in the efficiency in forming a self-assembly substance tend to occur in the presence of this excess amplifying probes. As a method to remove the excess amplifying probes and to enhance the efficiency in forming a self-assembly substance, it is preferable to use an exonuclease (for example, an exonuclease I and an exonuclease VII etc.) or amplifying probes of RNA and an RNase H. In the case where the amplifying probes of RNA and the RNase H are used, gene fragments amplified by a thermostable DNA polymerase or gene fragments amplified by a DNA polymerase having strand displacement activity are preferably used as target genes which serves as probes for a self-assembly substance forming reaction. For the thermostable DNA polymerase, KOD Dash (produced by Toyobo Co., Ltd.) and the like are preferably used. FIGS. 15 and 16 show schematic diagrams of the method for forming a self-assembly substance by using a thermostable DNA polymerase, amplifying probes of RNA and an RNase H.

When DNA is amplified by the use of a pair of amplifying probes of RNA as shown in FIG. 15(a), a pair of gene fragments composed of DNA (A' and B' regions, and C and D regions) and RNA (an X region and a Y region) is amplified [FIGS. 15(a) and 16(b)]. The RNA region part of the gene fragments and the amplifying probes of RNA are hydrolyzed by adding an RNase H to the solution after amplification and reacting them. As shown in FIG. 16(c), the pair of the gene fragments after treatment with the RNase is divided into 2 regions, respectively, and thereby forming a pair of cross-linking probes composed of 2 non-complementary regions to each other. It is preferable to design the amplifying probe of RNA so that any complementary regions may not remain in the pair of the gene fragments after treatment with the RNase H. However, this is not particularly limited, and the case in which some regions complementary to each other remain is also included in the present invention. The above pair of the cross-linking probes hybridizes to the dimer-probe which has been prepared correspondingly to the cross-linking probes so that they cross-link [FIG. 16(d)], and a self-assembly substance is formed [FIG. 16(e)]. According to the method mentioned above, it is possible to increase the efficiency in forming a self-assembly substance by removing the amplifying probes and cleaving an excess sequence which do not cross-link to the dimer-probe.

A second example of the method for forming a self-assembly substance using oligonucleotides synthesized by a gene amplification reaction according to the present invention makes use, as a probe in the above PALSAR method, of an oligonucleotide which is linked by a thermostable nucleic acid ligase and has a methylated base at the end regions (hereinafter also referred to as a "methylated probe"). This method is characterized in that methylated probes having region complementary to a target gene are provided, the regions complementary to the target gene are cleaved in advance, the cleaved probes are linked by ligation with a thermostable ligase enzyme in the presence of the target gene, and after the ligation reaction, unreacted methylated probes which behave as competing substances in the self-assembly reaction are degraded by the use of an exonuclease. The methylated bases of the oligonucleotides used in the gene amplification reaction are shown in FIG. 17. An example of the cases in which the amplified genes are used as dimer-forming probes is described below.

Figure 18:
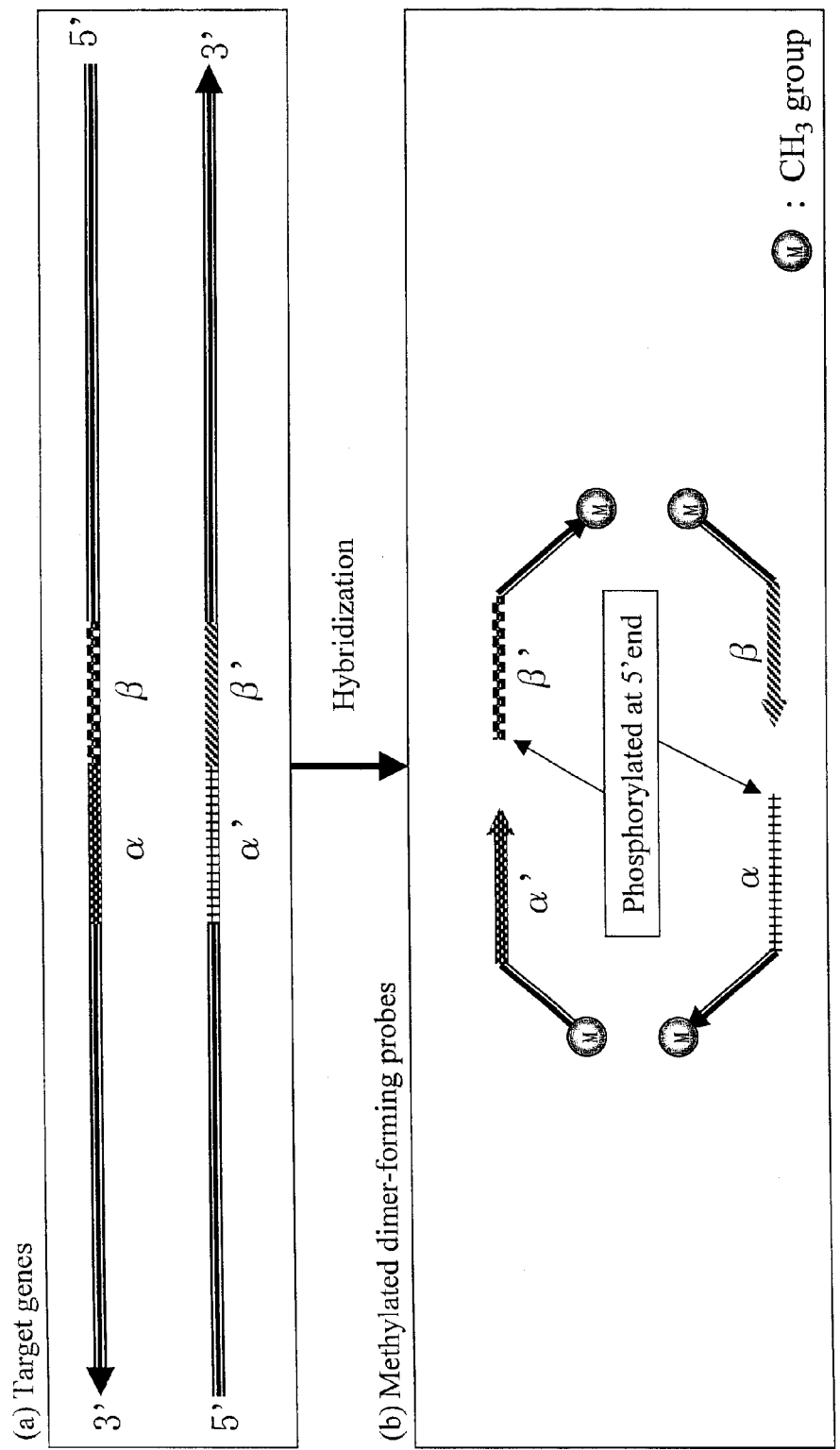
FIG. 18 is a schematic diagram showing in principle an embodiment of the second example of the method for forming a self-assembly substance using oligonucleotides according to the present invention, where (a) shows target genes and (b) shows cleaved and methylated dimer-forming probes, respectively.
Figure 21:
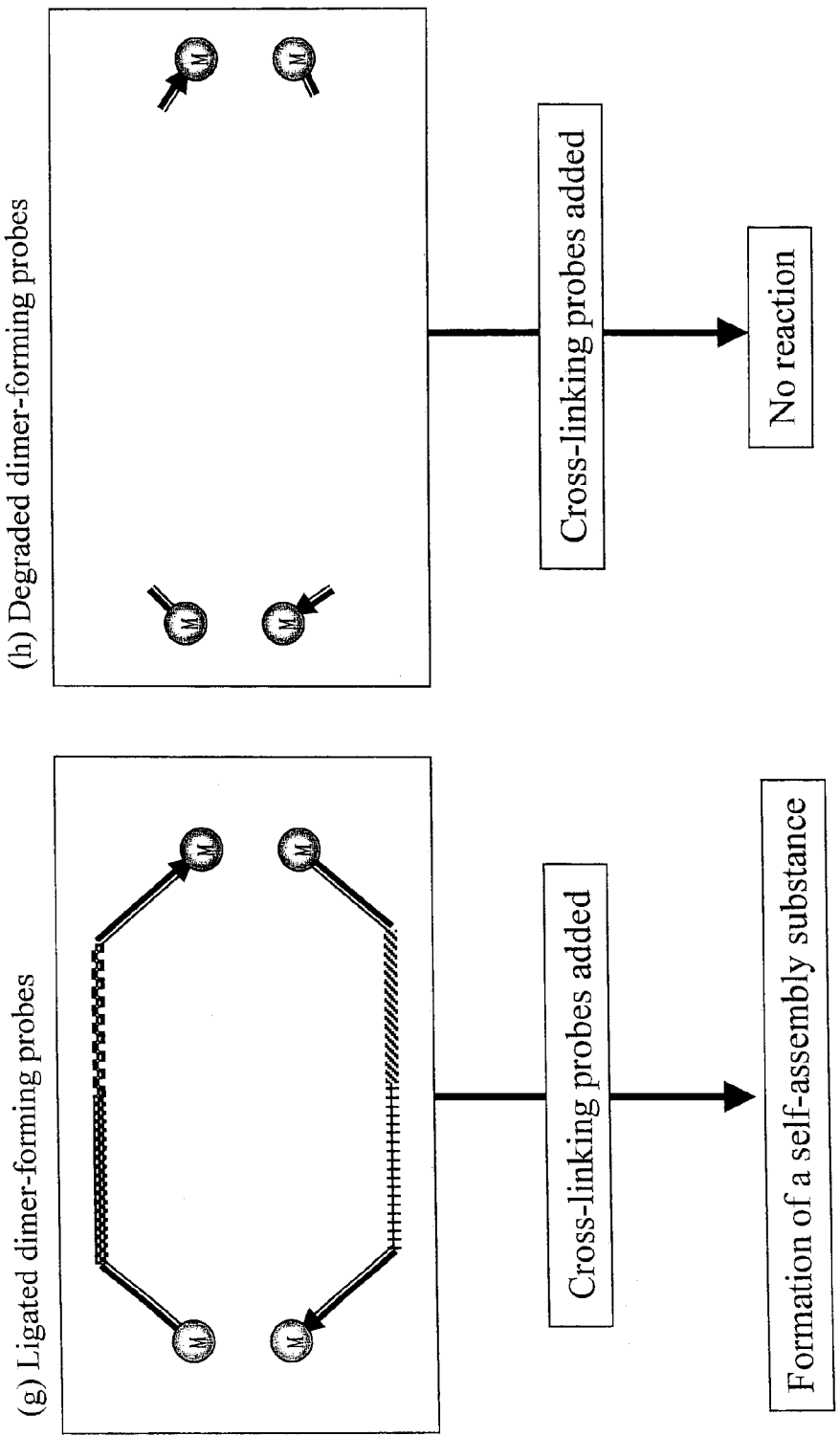
FIG. 21 is a schematic diagram showing in principle the embodiment of the second example of the method for forming a self-assembly substance using oligonucleotides according to the present invention, where (g) shows formation of a self-assembly substance in case of the ligated dimer-forming probes and (h) shows non-formation of a self-assembly substance in case of the split dimer-forming probes, respectively.
Figure 22:
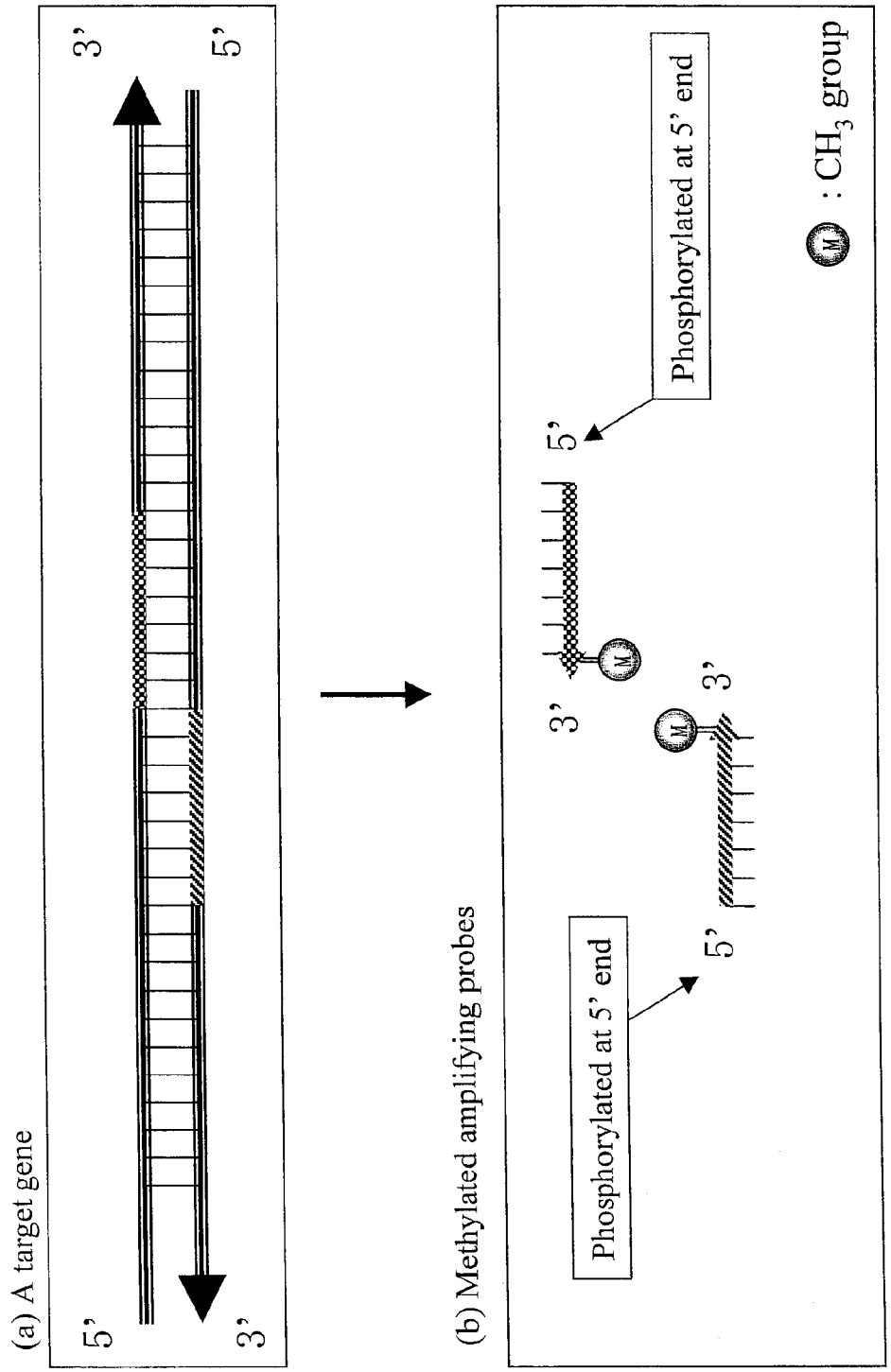
FIG. 22 is a schematic diagram showing in principle a first embodiment of the third example of the method forming a self-assembly substance using oligonucleotides according to the present invention, where (a) shows a target gene and (b) shows methylated amplifying probes, respectively.
Figure 23:
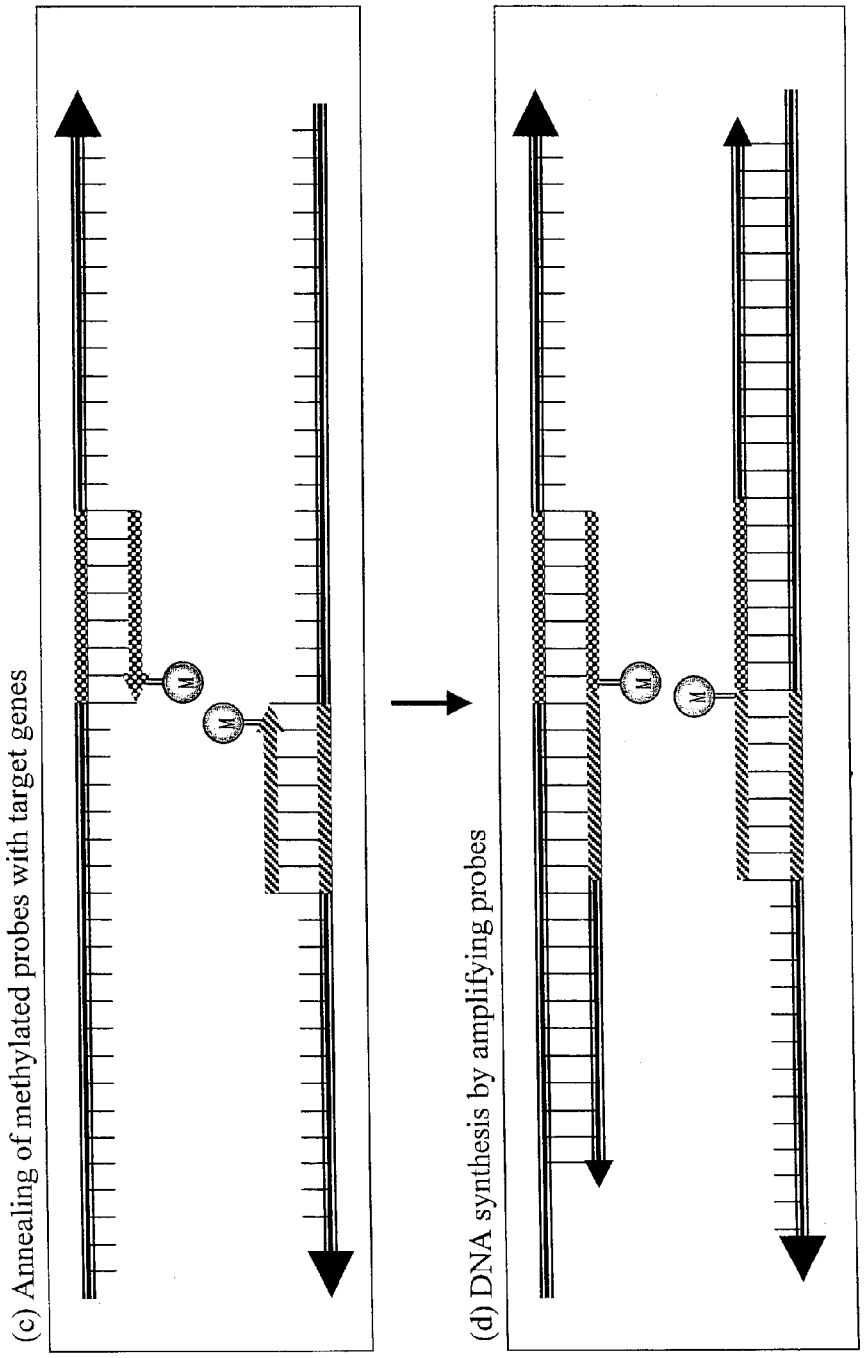
FIG. 23 is a schematic diagram showing in principle the first embodiment of the third example of the method for forming a self-assembly substance using oligonucleotides according to the present invention, where (c) shows hybridization of the methylated amplifying probes with the target genes and (d) shows DNA synthesis, respectively.
Figure 27:
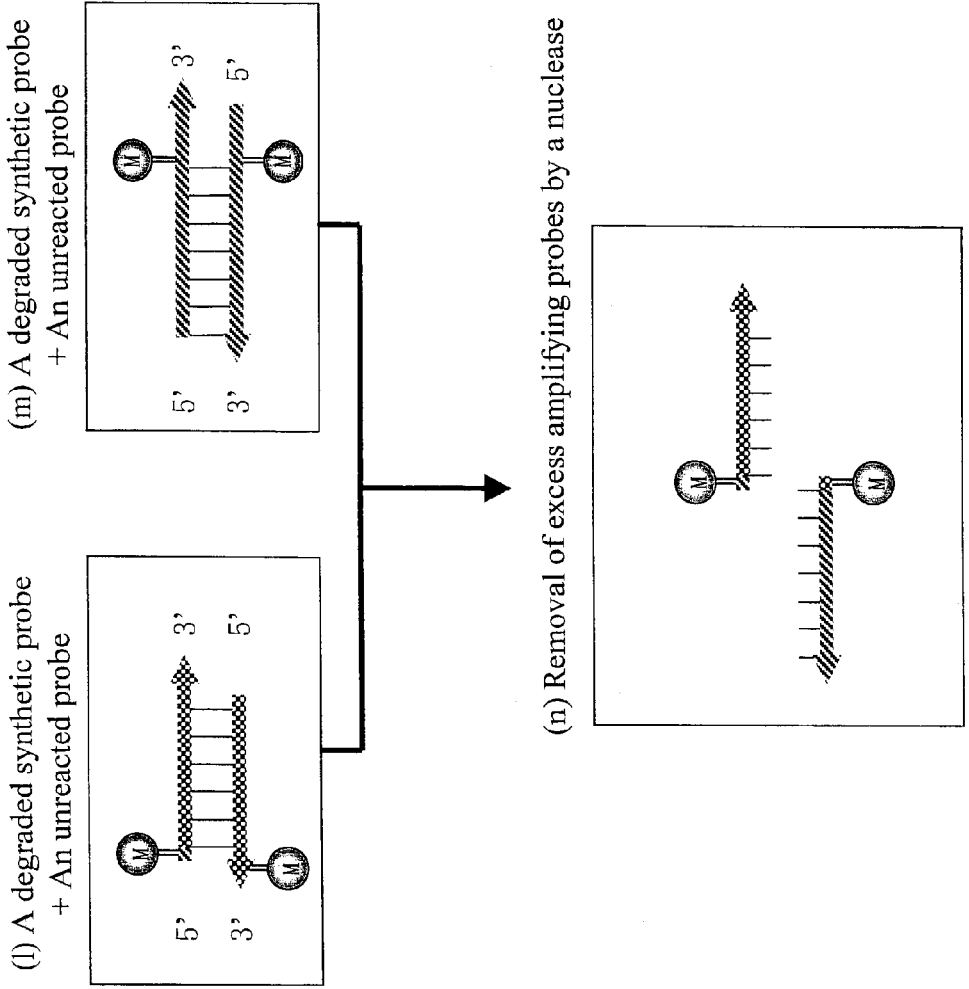
FIG. 27 is a schematic diagram showing in principle the first embodiment of the third example of the method for forming a self-assembly substance using oligonucleotides according to the present invention, where (l) and (m) show hybridization of the split synthetic probe with the unreacted probe and (n) shows treatment with a nuclease, respectively.

FIGS. 18 to 21 are schematic diagrams showing in principle an embodiment of the second example of the method for forming a self-assembly substance using oligonucleotides described above. As shown in FIG. 18, in the method for forming a self-assembly substance by using dimer-forming probes of a first group and cross-linking probes of a second group, the dimer-forming probes are prepared from a target gene [FIG. 18(a)] so that each probe has regions complementary to the target gene in a mid-region thereof (a' and β' regions, or a and β regions) as shown in (a) and (b) of FIG. 18, bases of the 5' end region and the 3' end region thereof are methylated, and further their mid-regions complementary to the target gene are pre-cleaved [FIG. 18(b)]. The cleaved dimer-forming probes are hybridized to the target genes as shown in FIG. 19(c), and then linked together by the action of a thermostable ligase as shown in FIG. 19(d). This sequence of the reactions is repeated using a thermal cycler, thereby multiplying the ligated dimer-forming probes. Thereafter, when a nuclease, for example, an exonuclease such as an exonuclease VII, is added, the dimer-forming probes ligated in the presence of the target gene are not susceptible to degradation because bases of both ends of the ligated dimer-forming probes are methylated as shown in FIG. 20(e), while the dimer-forming probes remaining in cleaved forms in the absence of the target gene [FIG. 20(f)] are degraded completely because both cleaved ends of the dimer-forming probes not ligated are not methylated, and therefore a self-assembly substance can not be formed [FIG. 21(h)]. The ligated dimer-forming probes can form a self-assembly substance by the addition of cross-linking probes prepared separately [FIG. 21(g)]. Thus, the presence of the target gene can be confirmed by confirming formation of a self-assembly substance.

A third example of the method for forming a self-assembly substance using oligonucleotides synthesized by a gene amplification reaction according to the present invention makes use of amplifying probes having a methylated base at the end region and oligonucleotides amplified with a thermostable nucleic acid polymerase as the probes in the above PALSAR method. This method is characterized in that at least one of the amplifying probes has a methylated base at the 3' end region and a phosphorylated base at the 5' end region, and serves as a probe for gene amplification by a thermostable DNA polymerase, and after the gene amplification, the amplifying probes present in excess which behave as competing substances in the self-assembly reaction are degraded by the use of an exonuclease. An example of the cases in which an amplified gene (hereinafter also referred to as a "synthetic probe") is used as a cross-linking probe or an HCP is explained below.

FIGS. 22 to 27 are schematic diagrams showing in principle a first embodiment of the third example of the method for forming a self-assembly substance using oligonucleotides described above. Probes complementary to the solid line parts of the target gene shown in FIG. 22(a) are prepared, each probe having a methylated base at the 3' end region [FIG. 22(b)]. Next, the methylated amplifying probes are annealed to the target genes [FIG. 23(c)], followed by DNA synthesis with a thermostable DNA polymerase [FIG. 23(d)]. This sequence of the reactions is repeated using a thermal cycler [FIG. 24(e)-(f)], thereby multiplying the amplified synthetic probes [FIG. 25(g)]. Upon addition of a nuclease, for example, an exonuclease such as a T7 Gene 6 exonuclease, the amplified synthetic probes are degraded from the 5' end up to the front of the methylated base as shown in FIG. 25(h). The degraded synthetic probes [FIG. 26(i)] can be used as a pair of cross-linking probes [FIG. 26(j)] or one of each pair of two kinds of pairs of HCPs [FIG. 26(k)], and a self-assembly substance can be formed by adding dimer-forming probes or the other HCP prepared separately.

In addition, as shown in FIG. 27(l)-(m), the degraded synthetic probes are further hybridized to the unreacted probes, and then subjected to enzyme treatment, thereby allowing the probes to be degraded more completely from the 5' end up to the very front of the methylated base [FIG. 27(n)].

Figure 28:
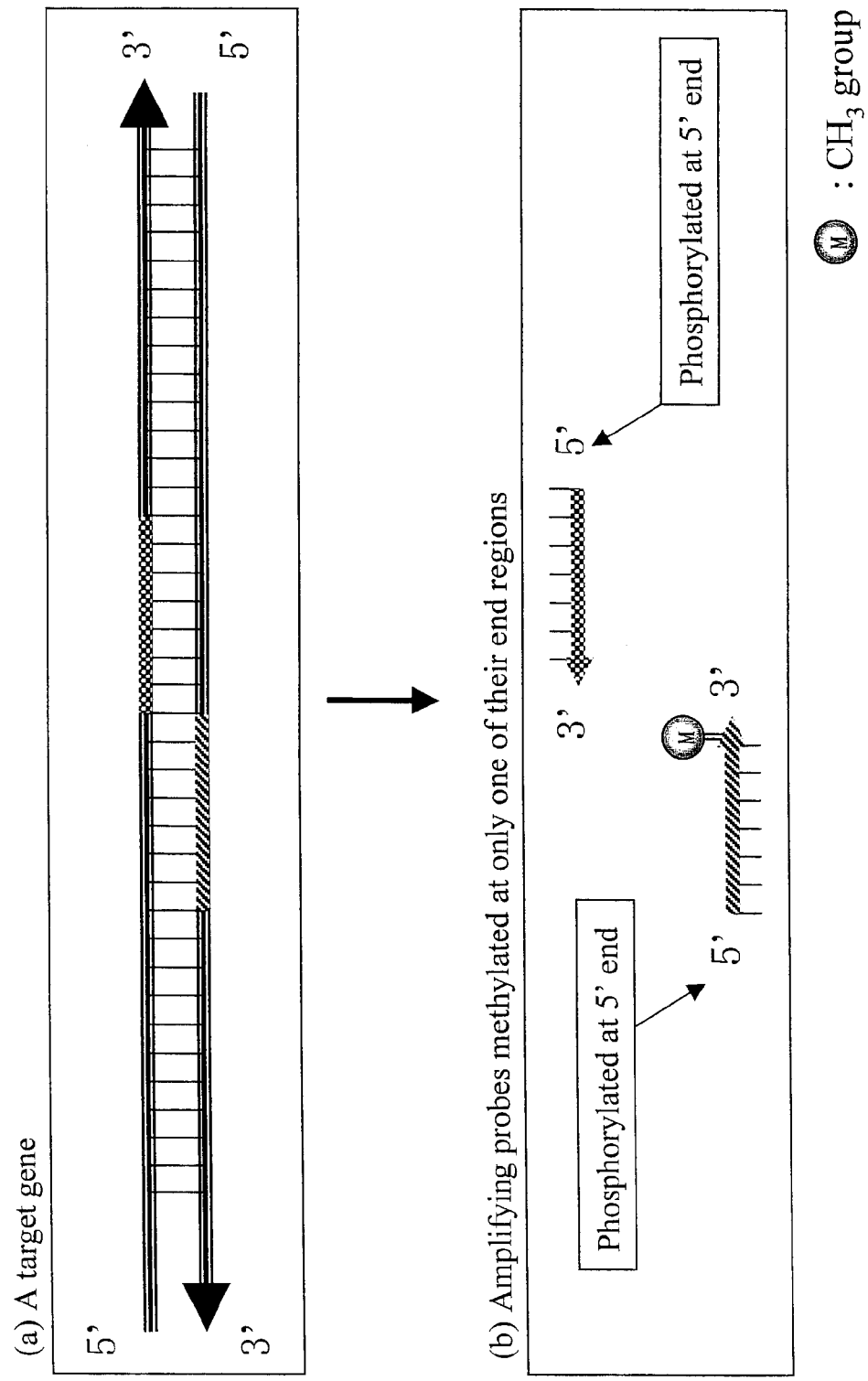
FIG. 28 is a schematic diagram showing in principle a second embodiment of the third example of the method for forming a self-assembly substance using oligonucleotides according to the present invention, where (a) shows a target gene and (b) shows a pair of amplifying probes, wherein only one of them is methylated, respectively.
Figure 30:
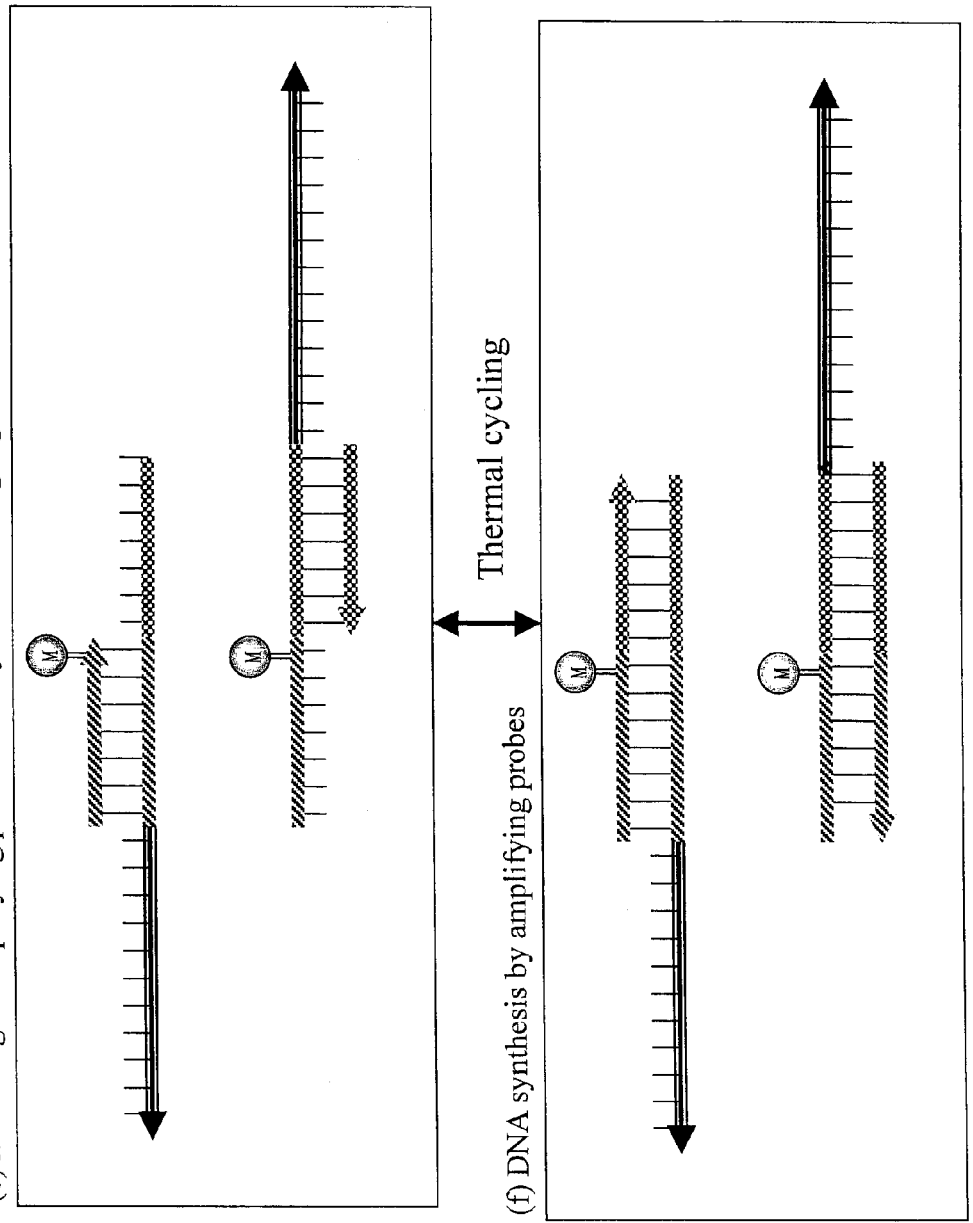
FIG. 30 is a schematic diagram showing in principle the second embodiment of the third example of the method for forming a self-assembly substance using oligonucleotides according to the present invention, where (e) shows hybridization of the amplifying probes with the synthesized DNA and (f) shows DNA synthesis, respectively.
Figure 34:
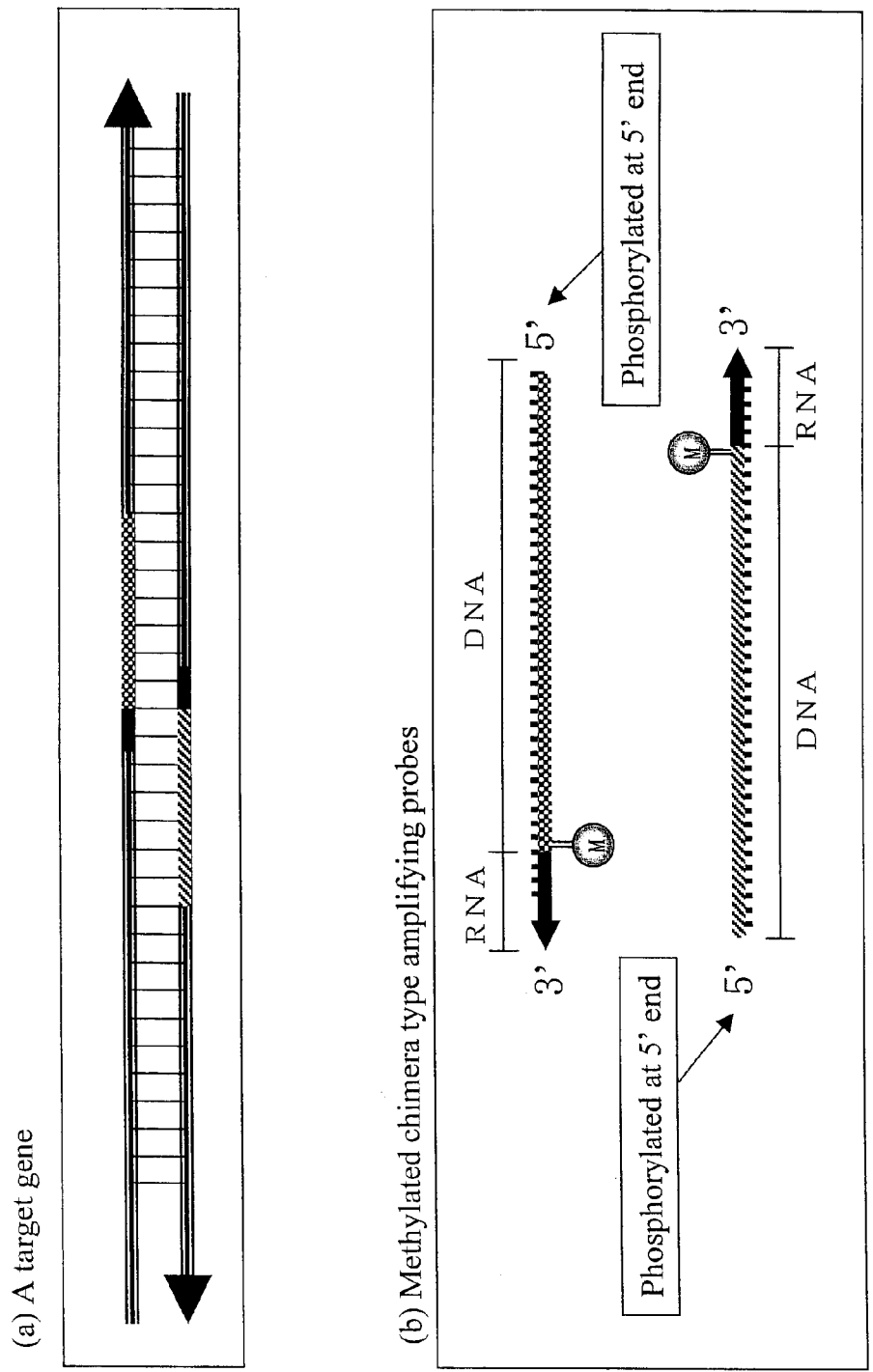
FIG. 34 is a schematic diagram showing in principle an embodiment of a 4th example of the method for forming a self-assembly substance using oligonucleotides according to the present invention, where (a) shows a target gene and (b) shows chimera type amplifying probes methylated, respectively.
Figure 35:
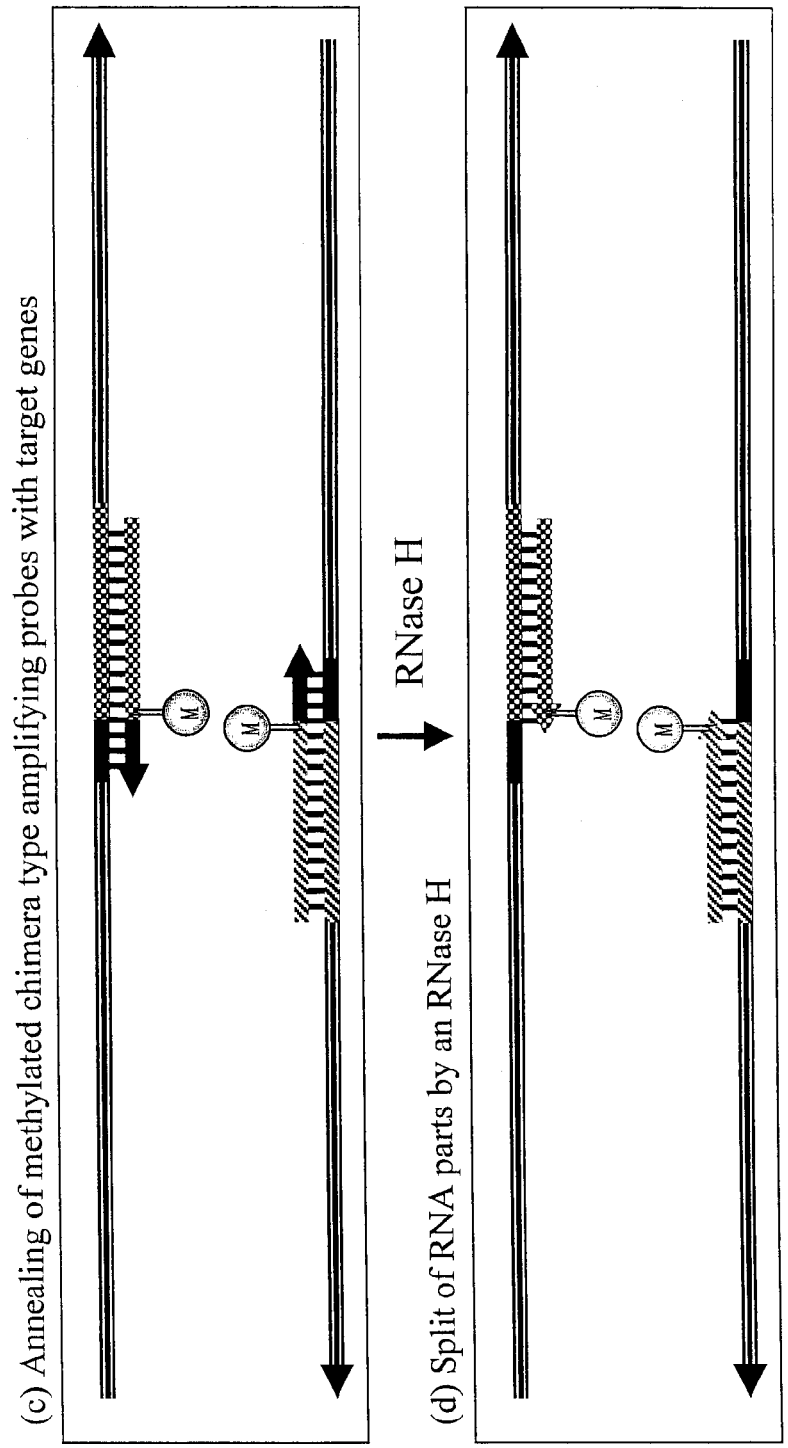
FIG. 35 is a schematic diagram showing in principle the embodiment of the 4th example of the method for forming a self-assembly substance using oligonucleotides according to the present invention, where (c) shows hybridization of the chimera type amplifying probes methylated with the target genes and (d) shows treatment with an RNase H, respectively.
Figure 36:
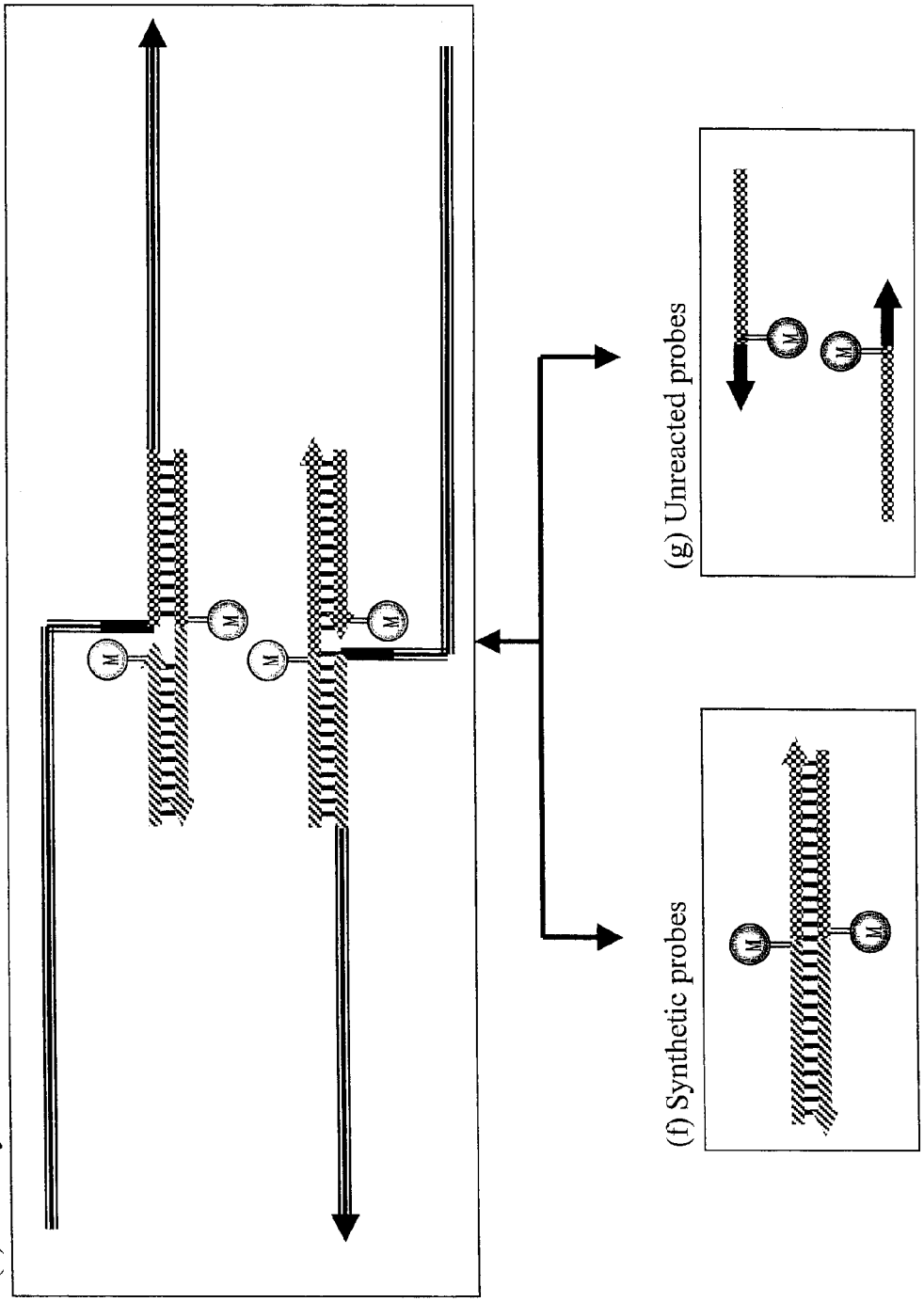
FIG. 36 is a schematic diagram showing in principle the embodiment of the 4th example of the method for forming a self-assembly substance using oligonucleotides according to the present invention, where (e) shows DNA synthesis with an enzyme having strand displacement activity, (f) shows synthetic probes, and (g) shows the unreacted probes, respectively.
Figure 39:
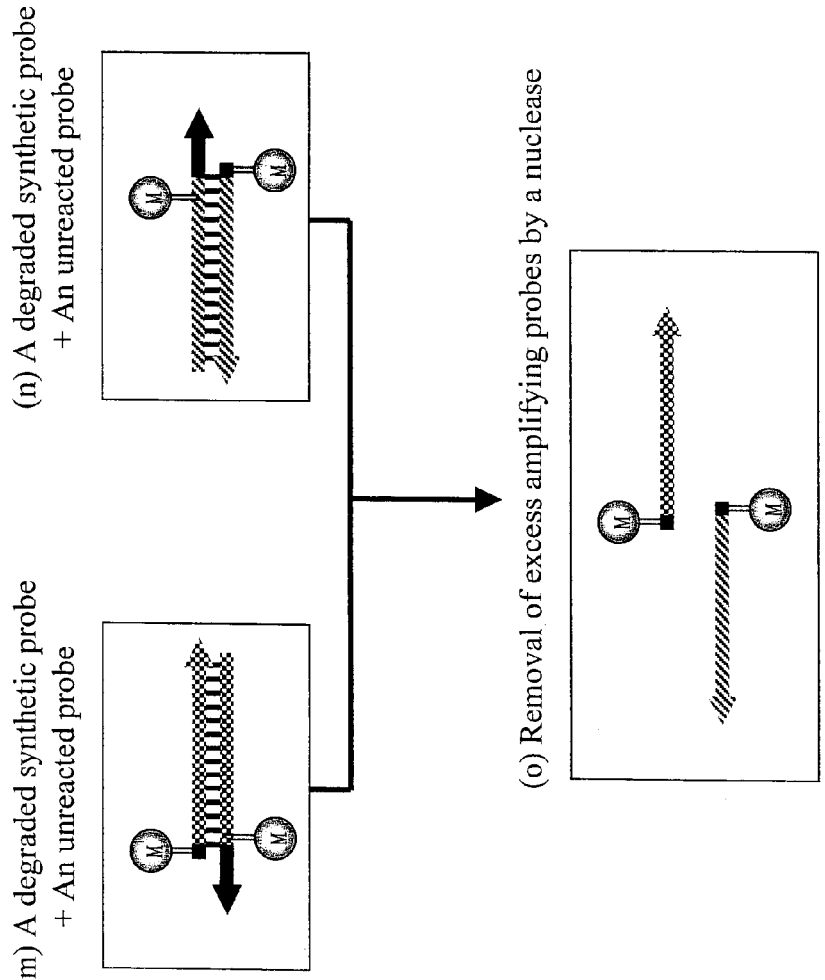
FIG. 39 is a schematic diagram showing in principle the embodiment of the 4th example of the method for forming a self-assembly substance using oligonucleotides according to the present invention, where (m) and (n) show hybridization of the unreacted probe with the split synthetic probe and (o) shows treatment with a nuclease, respectively.
Figure 40:
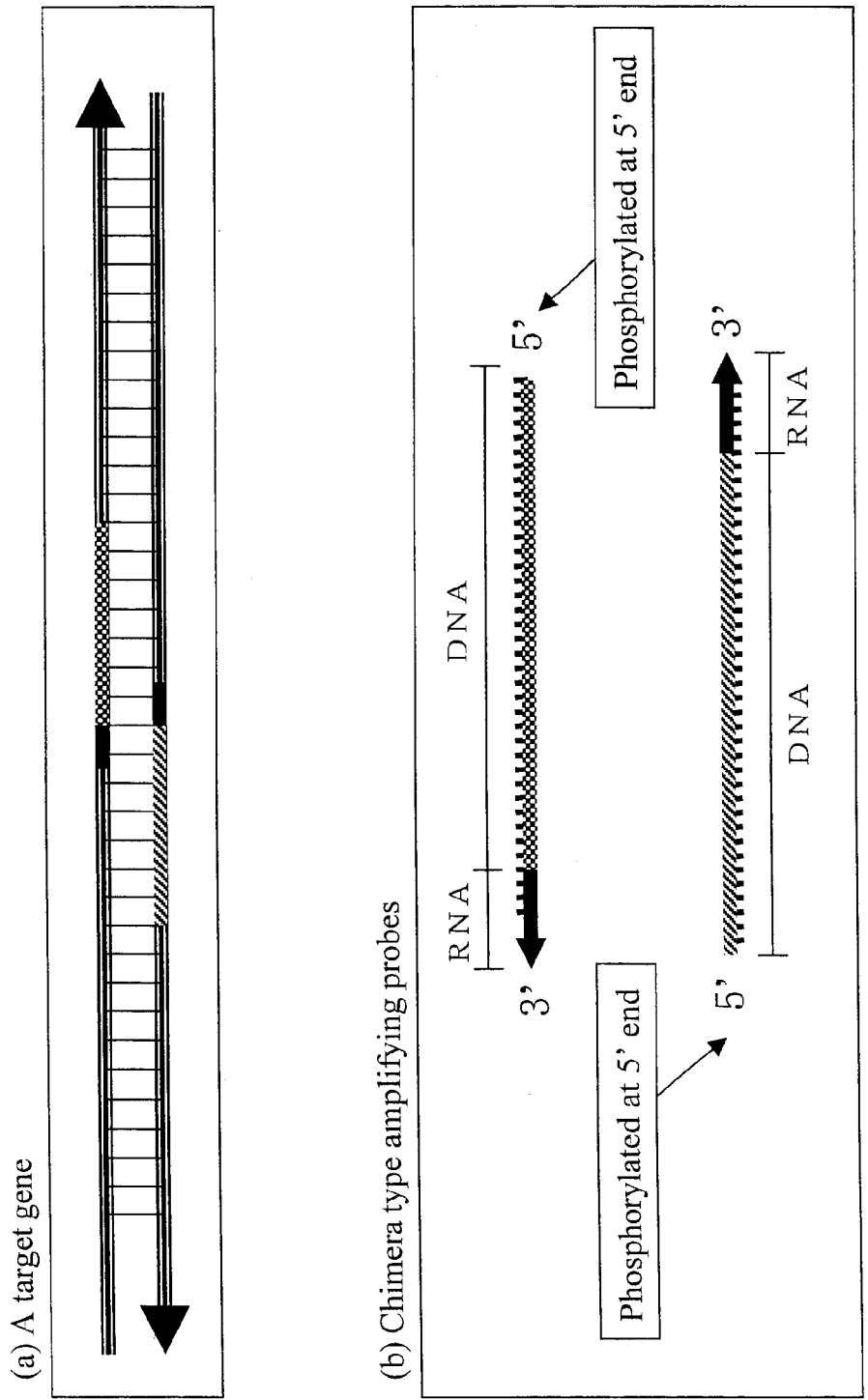
FIG. 40 is a schematic diagram showing in principle an embodiment of a 5th example of the method for forming a self-assembly substance using oligonucleotides according to the present invention, where (a) shows a target gene and (b) shows chimera type amplifying probes, respectively.
Figure 41:
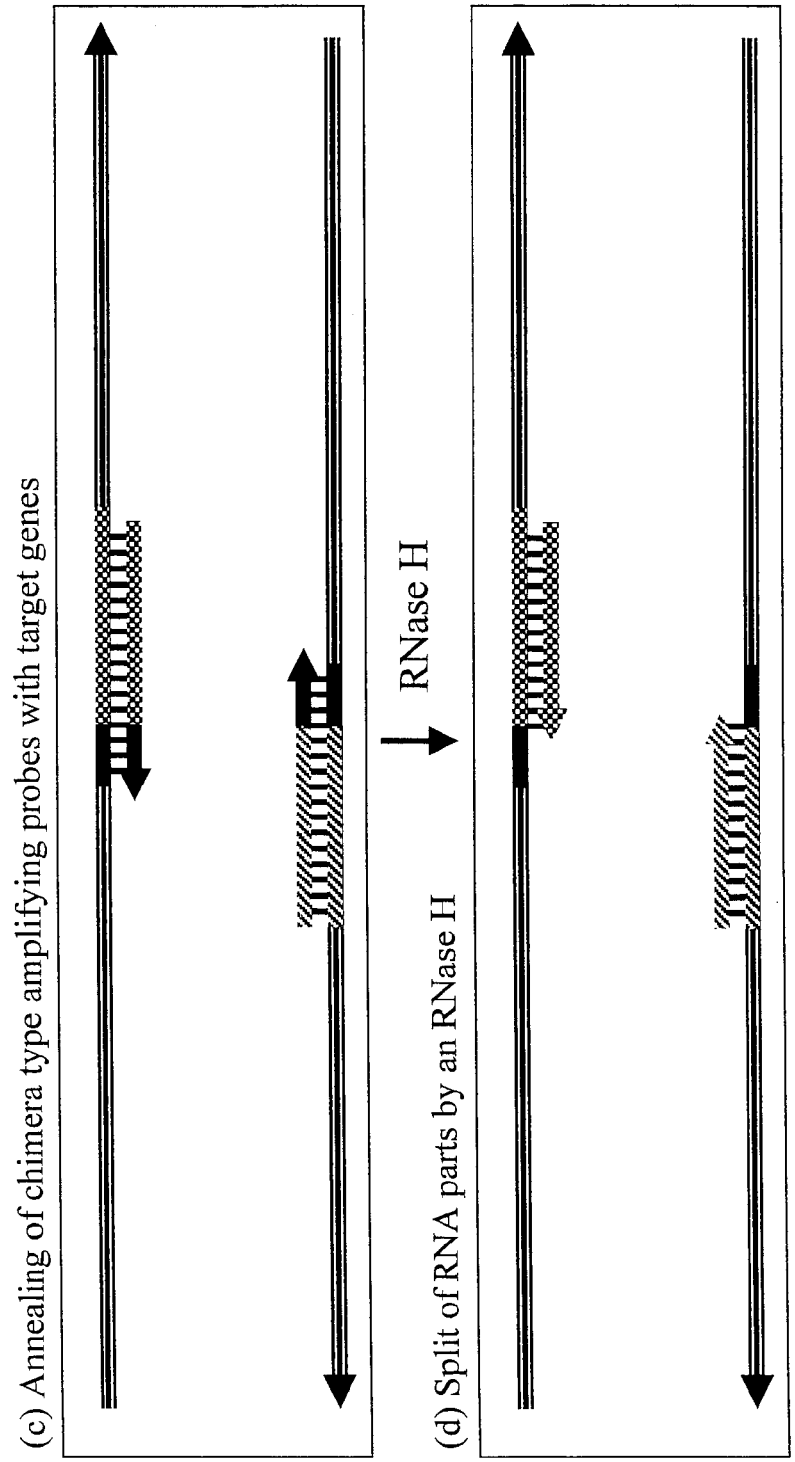
FIG. 41 is a schematic diagram showing in principle the embodiment of the 5th example of the method for forming a self-assembly substance using oligonucleotides according to the present invention, where (c) shows hybridization of the chimera type amplifying probes with the target genes and (d) shows treatment with an RNase H, respectively.
Figure 42:
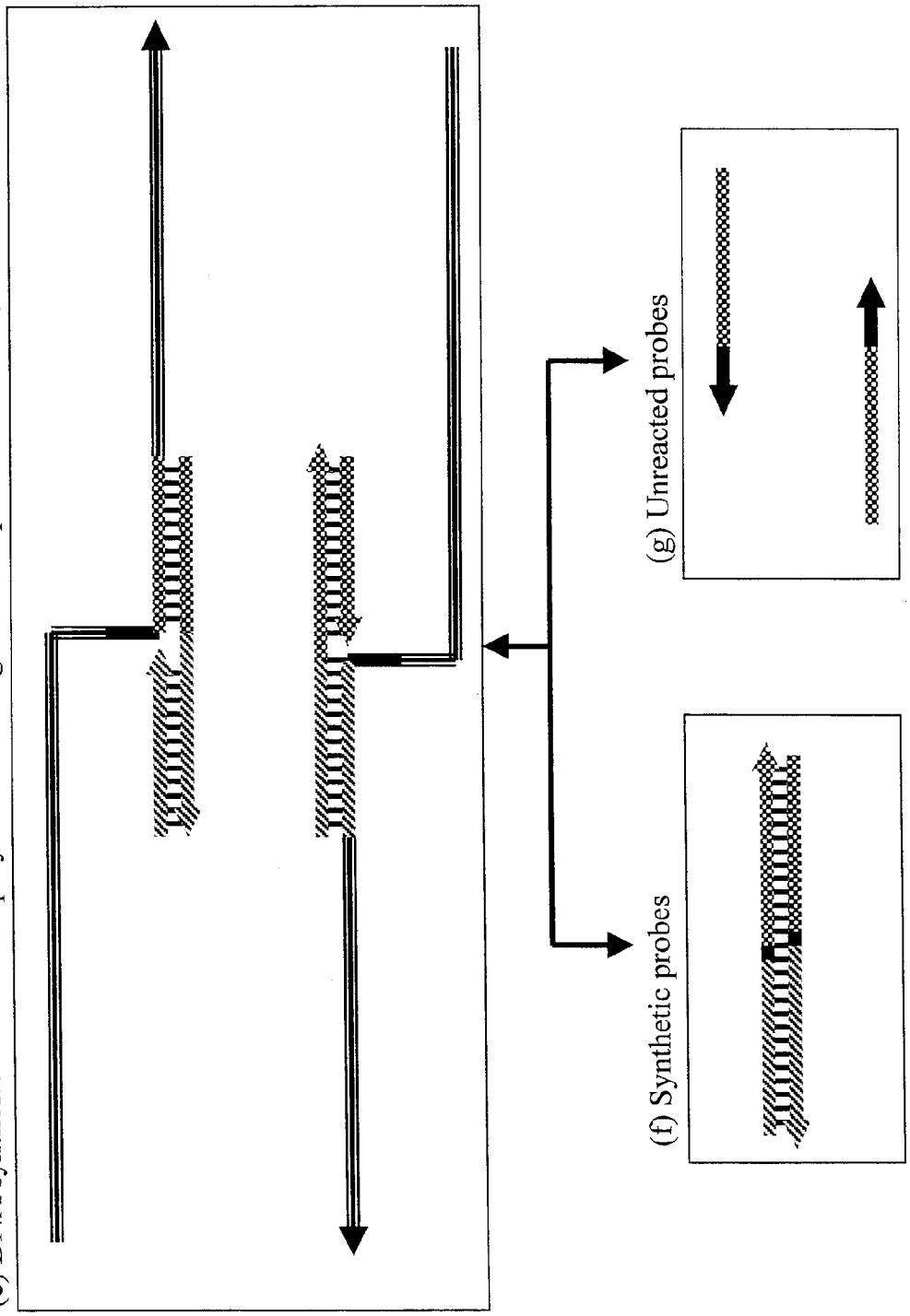
FIG. 42 is a schematic diagram showing in principle the embodiment of the 5th example of the method for forming a self-assembly substance using oligonucleotides according to the present invention, where (e) shows DNA synthesis with an enzyme having strand displacement activity, (f) shows synthetic probes, and (g) shows the unreacted probes, respectively.

FIGS. 28 to 33 are schematic diagrams showing in principle a second embodiment of the third example of the method for forming a self-assembly substance using oligonucleotides described above. FIG. 28 shows gene amplification with a methylated amplifying probe by a thermostable DNA polymerase and formation of a self-assembly substance. Amplifying probes complementary to the solid line parts of the target gene shown in FIG. 28(a) are prepared, wherein only one of the amplifying probes has a methylated base at the 3' end region [FIG. 28(b)]. Next, the amplifying probes are annealed to the target genes [FIG. 29(c)], followed by DNA synthesis with a thermostable DNA polymerase [FIG. 29(d)]. This sequence of the reactions is repeated using a thermal cycler [FIG. 30(e)-(f)], thereby multiplying the amplified synthetic probes [FIG. 31(g)]. Upon addition of a nuclease, for example, an exonuclease such as a T7 Gene 6 Exonuclease, the amplified probes are degraded from the 5' end to the front of the methylated base as shown in FIG. 31(h). The degraded synthetic probes [FIG. 32(i)] can be used as one of a pair of cross-linking probes [FIG. 32(j)] or one of a pair of HCPs [FIG. 32(k)], and a self-assembly substance can be formed by adding the other cross-linking probe and a pair of dimer-forming probes or by adding the other HCP, all of which are prepared separately.

In addition, as shown in FIG. 33(l), the degraded synthetic probe is further hybridized to the unreacted probe, and then subjected to enzyme treatment, thereby allowing the unreacted probe to be degraded more completely [FIG. 33(m)].

A 4th example of the method for forming a self-assembly substance using oligonucleotides synthesized by a gene amplification reaction according to the present invention makes use of genes (synthetic probes) amplified by DNA polymerase having strand displacement activity as probes in the above PALSAR method, wherein chimera probes composed of DNA and RNA are used as amplifying probes, each chimera probe having a methylated base at the 3' end region of DNA adjacent to RNA. This method is characterized in that at least one of the amplifying probes is provided with RNA bases on the 3' side and DNA bases on the 5' side, is methylated at the 3' end region of the DNA region, and serves as a probe for use in gene amplification by a DNA polymerase having strand displacement activity, and that after the gene amplification, the amplifying probes present in excess which behave as competing substances in the self-assembly reaction are degraded by the use of an exonuclease. A case in which amplified genes are used as cross-linking probes or HCPs is explained below.

FIGS. 34 to 39 are schematic diagrams showing in principle an embodiment of the 4th example of the method for forming a self-assembly substance using oligonucleotides described above. Amplifying probes complementary to the solid line parts of the target gene [FIG. 34(a)] are prepared, each amplifying probe composed of DNA and RNA and having only a methylated base at the 3' end region of DNA adjacent to RNA [FIG. 34(b)]. Next, the above amplifying probes are annealed to the target genes [FIG. 35(c)], and the RNA parts are split by an RNase H [FIG. 35(d)], followed by DNA synthesis with a DNA polymerase having strand displacement activity [FIG. 36(e)]. This sequence of the reactions is repeated isothermally, thereby multiplying the amplified synthetic probes [FIGS. 36(f) and 37(h)]. Upon addition of a nuclease, for example, an exonuclease such as a T7 Gene 6 Exonuclease, the amplified synthetic probes are degraded from the 5' end to the front of the methylated base as shown in FIG. 37(i). The degraded synthetic probes [FIG. 38(j)] can be used as a pair of cross-linking probes [FIG. 38(k)] or one of each pair of two kinds of pairs of HCPs [FIG. 38(l)], and a self-assembly substance can be formed by adding a pair of dimer-forming probes or the other HCPs prepared separately.

In addition, the degraded synthetic probes are further hybridized to the unreacted probes as shown in FIG. 39(m)-(n), and then subjected to enzyme treatment, thereby allowing the unreacted probes to be degraded more completely [FIG. 39(o)].

A 5th example of the method for forming a self-assembly substance using oligonucleotides synthesized by a gene amplification reaction according to the present invention makes use of genes amplified by a DNA polymerase having strand displacement activity as probes in the above PALSAR method, wherein chimera probes composed of DNA and RNA are used as amplifying probes. This method is characterized in that amplifying probes are provided as probes for gene amplification by a DNA polymerase having strand displacement activity, wherein at least one of the amplifying probes comprises RNA bases on the 3' side and DNA bases on the 5' side, and that after the gene amplification, the amplifying probes present in excess which behave as competing substances in the self-assembly reaction are degraded by the use of an exonuclease. A case in which amplified genes are used as cross-linking probes or HCPs is explained below.

FIGS. 40 to 45 are schematic diagrams showing in principle an embodiment of the 5th example of the method for forming a self-assembly substance using oligonucleotides described above. Amplifying probes complementary to the solid line parts of the target gene shown in FIG. 40(*a*) and composed of DNA and RNA are prepared [FIG. 40(*b*)]. Next, the above amplifying probes are annealed to the target genes [FIG. 41(*c*)], and the RNA parts are split by an RNase H [FIG. 41(*d*)], followed by DNA synthesis with a DNA polymerase having strand displacement activity [FIG. 42(*e*)]. This sequence of the reactions is repeated isothermally, thereby multiplying the amplified synthetic probes [FIGS. 42(*f*) and 43(*h*)]. Upon addition of a nuclease, for example, an exonuclease such as a T7 Gene 6 Exonuclease, the amplified synthetic probes are degraded from the 5' end up to the RNA part as shown in FIG. 43(*i*). The degraded synthetic probes [FIG. 44(*j*)] can be used as a pair of cross-linking probes [FIG. 44(*k*)] or one of each pair of two kinds of pairs of HCPs [FIG. 44(*l*)], and a self-assembly substance can be formed by adding a pair of dimer-forming probes or the other HCPs prepared separately.

Figure 45:
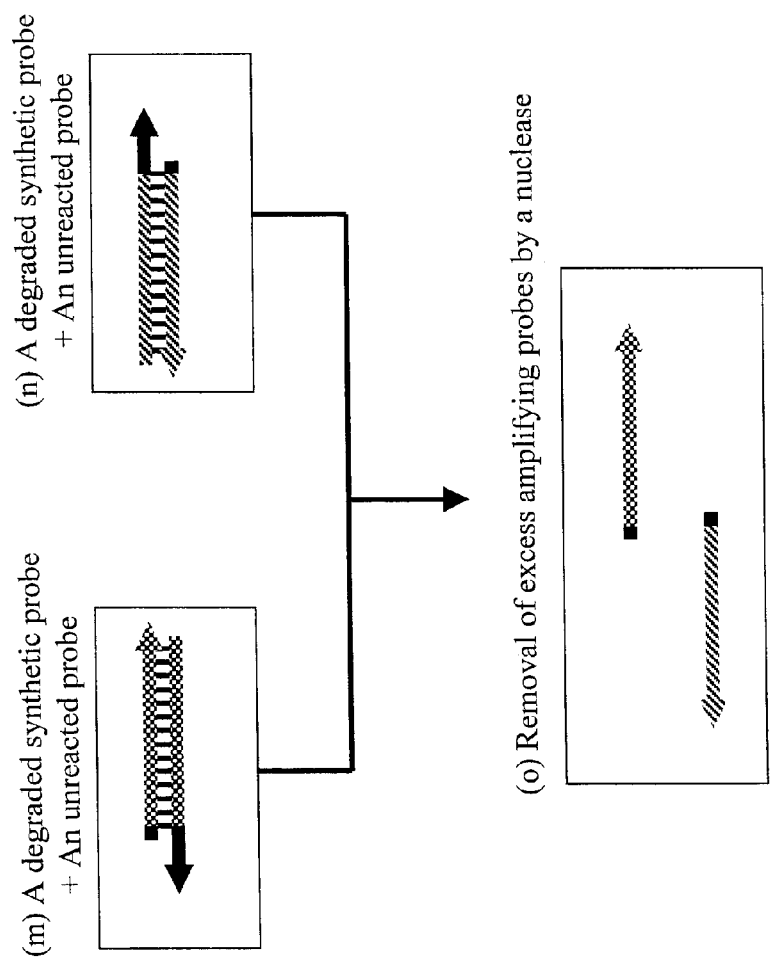
FIG. 45 is a schematic diagram showing in principle the embodiment of the 5th example of the method for forming a self-assembly substance using oligonucleotides according to the present invention, where (m) and (n) show hybridization of the unreacted probe with the split synthetic probe and (o) shows treatment with a nuclease, respectively.

In addition, the degraded synthetic probes are further hybridized to the unreacted probes as shown in FIG. 45(*m*)-(*n*), and then subjected to enzyme treatment, thereby allowing the unreacted probes to be degraded more completely [FIG. 45(*o*)].

The self-assembly substance formed by the above method can easily be also detected by the general agarose gel electrophoresis and the like.

Since the stacking of bases in the self-assembly substance formed according to the present invention has a regular higher-order structure, it is also possible to confirm the state of the self-assembly substance by observing a hypochromic effect called "hypochromism" reducing the intensity of an absorption band at 260 nm in the ultraviolet region.

Furthermore, by adding a fluorescent substance having the property of bonding to a nucleic acid and checking a change in fluorescence intensity, the state of the self-assembly substance can be confirmed. For example, the self-assembly substance can be detected by adding a coloring matter that is inserted into two strands of oligonucleotides to emit fluorescence and monitoring emission of fluorescence with the I-CORE™ (Smart Cycler™) made by Cepheid Inc., and so forth.

As described above, the method for forming a self-assembly substance using oligonucleotides according to the present invention allow the self-assembly substance to be formed only in the presence of a target gene, and therefore it is possible to detect the target gene by detecting formed the self-assembly substance.

EXAMPLES

In the following, the present invention will be specifically explained in conjunction with several Examples. These Examples are, however, illustrative of the present invention and should not be interpreted to limit the scope of the present invention.

Examples 1 to 16

The following are oligonucleotide-probes used in Examples 1 to 16.

[1] Cross-Linking Probe-1 [Underlined Part; Redundant Sequence (tag)]
5'-TTGGATCAACCCGCTCAATG CCTG-GAGATTTGGGCGTGC-CCCGCA AGACTGCTAGC-CGA GTAGTGTTGGGTCGCGAAAG-3'

[2] Cross-Linking Probe-2 [Underlined Part; Redundant Sequence (tag)]
3'-AACCTAGTTGGGCGAGTTAC GGACCTCTAAAC-CCGCACGG-GGGCGT TCTGACGATCGGCT CAT-CACAACCCAGCGCTTTC-5'

[3] Cross-Linking Probe-3
5'-TTGGATCAACCCGCTCAATG CCTG-GAGATTTGGGCGTGC-3'

[4] Cross-Linking Probe-4
3'-GGGCGTTCTGACGATCGGCT CATCACAAC-CCAGCGCTTTC-5'

[5] Dimer-Forming Probe-1
5'-GTAGTGTTGGGTCGCGAAAG-GCTCACAGT-TAAGCCGTGAG-CCCGCA AGACTGCTAGCCGA-3'

[6] Dimer-Forming Probe-2
5'-CATTGAGCGGGTTGATCCAA-CTCACGGCT-TAACTGTGAGC-GGCACG CCCAAATCTCCAGG-3'

Examples 1 to 14

(1) Object

There was examined whether cross-linking probes could form a self-assembly substance with dimer-probes, in cases where gene fragments supposed to be amplified by a known gene amplification method were used as the cross-linking probes, each gene fragment having a redundant sequence (tag) which did not hybridize to the dimer-probes.

(2) Materials
(a) As cross-linking probes, two synthetic oligonucleotide-probes of 80 bases supposed to be amplified by a known gene amplification method and having complementary sequences (a cross-linking probe-1 and a cross-linking probe-2), and dimer-forming probes corresponding to them (a dimer-forming probe-1 and a dimer-forming probe-2) were prepared. These probes were prepared at a concentration of 100 pmoles/µL, respectively.
(b) In Examples 1 to 7, 2 M-CaCl$_2$ solution was used as a buffer. In Examples 8 to 14, 20×SSC solution (3 M-NaCl, 0.3 M-C$_6$H$_5$O$_7$Na$_3$.2H$_2$O; 20×SSC solution was indicated as 3 M-NaCl solution in Examples 8 to 14) was used as a buffer.

(3) Method
(a) Preparation of Reaction Solutions
To combined solutions of 0.5 µL each of the cross-linking probe-1, the cross-linking probe-2, the dimer-forming probe-1 and the dimer-forming probe-2 were added the buffer solution (2 M-CaCl$_2$ solution or 3 M-NaCl solution) and sterile redistilled water to prepare 20 µL of reaction solutions. The buffer solution and sterile redistilled water were added so that the final concentrations of the buffer in the reaction solutions might be adjusted to 1.2 M (Examples 1 and 8), 1.0 M (Examples 2 and 9), 0.8 M (Examples 3 and 10), 0.6 M (Examples 4 and 11), 0.4 M (Examples 5 and 12), 0.2 M (Examples 6 and 13) and 0.05 M (Examples 7 and 14), respectively.

(b) Formation Reaction of a Self-Assembly Substance

Each of the above reaction solutions was allowed to react first at 94° C. for 30 seconds and then at 70° C. for 1 hour with a thermal cycler (manufactured by PerkinElmer Inc.), thereby carrying out formation reaction of a self-assembly substance.

(c) Confirmation of a Self-Assembly Substance by Agarose Gel Electrophoresis

To 8 μL of the reaction solution after the formation reaction of a self-assembly substance was added 2 μL of a loading buffer, and then the gel electrophoresis was carried out for 30 minutes at 100 volts using 2% of Nusieve 3:1 agarose gel (product of Bio Whittaker Molecular Applications). DNA Molecule Weight Marker XV (product of Boehringer Mannheim Corp.) was used as a molecular size marker.

Examples 15 and 16

(1) Object

There was examined whether a self-assembly substance was formed according to the PALSAR method, in cases where gene fragments were used as cross-linking probes, wherein the gene fragment had been amplified by a known gene amplification method and then redundant sequences (tag) incapable of hybridizing to dimer-probes had been deleted from the gene fragments by an enzyme or the like.

(2) Materials (a) As cross-linking probes, a pair of oligonucleotides-probes not complementary to each other (a cross-linking probe-3 and a cross-linking probe-4) was synthesized, in which the tags present in the synthetic oligonucleotides-probes used in Examples 1 to 14 were deleted for use as the cross-linking probes in these examples. As dimer-forming probes, the dimer-forming probe-1 and the dimer-forming probe-2, both used in Examples 1 to 14, were utilized. These probes were prepared at a concentration of 100 pmoles/μL, respectively.

(b) In Example 15, 2 M-CaCl$_2$ solution was used as a buffer. In Example 16, 3 M-NaCl solution was used as a buffer.

(3) Method (a) Preparation of Reaction Solutions

To combined solutions of 0.5 μL each of the cross-linking probe-3, the cross-linking probe-4, the dimer-forming probe-1 and the dimer-forming probe-2 were added the buffer solution and sterile redistilled water to prepare 20 μL of reaction solutions. The buffer solution and sterile redistilled water were added so that the final concentration of the buffer in the reaction solution might be adjusted to 1.2 M.

(b) Formation Reaction of a Self-Assembly Substance

Formation reaction of a self-assembly substance was carried out by the same procedures and under the same conditions as those in Examples 1 to 14.

(c) Confirmation of a Self-Assembly Substance By Agarose Gel Electrophoresis

A self-assembly substance was confirmed by the same procedures and under the same conditions as those in Examples 1 to 14.

(4) Results

The results of Examples 1 to 16 are shown in FIG. 46. In the case of the cross-linking probes having redundant sequences (tag), formation of a self-assembly substance were observed only in CaCl$_2$ solutions, which is evident by comparing the results of the reaction in CaCl$_2$ solutions of Examples 1 to 7 (Lanes 1 to 7) with those in 20×SSC solutions of Examples 8 to 14 (Lanes 9 to 15). The concentration of CaCl$_2$ solution appropriate for significant formation of a self-assembly substance was particularly in the vicinity of 0.8 M (Lane 3). In Example 15 (Lane 8) and Example 16 (Lane 16) in which extra sequences (tag) had been removed, formation of a self-assembly substance was observed independently of the buffer solution used. These results confirmed that the efficiency in forming the self-assembly substance was higher in the case of the cross-linking probes removed extra sequences (tag), but that it is also possible to form the self-assembly substance with the dimer-forming probes in the case of the cross-linking probes complementary to each other and having extra sequences (tag). Accordingly, it is shown that these are applicable to a system in which a conventional gene amplification method is combined with a formation reaction of a self-assembly substance.

Example 17 And Comparative Example 1

Oligonucleotide-probes used in Example 17 and Comparative Example 1 are shown below, where ☐ indicates methylated bases.

[7] Target Gene-A (Underlined Part; Complementary Region)
5'-AACATGAAAA AT GATTATGGCT CAGGTACTGC TATCCACCCT CAAA CAGGTG AATTATTA GCACT-TGTAA GCACACCTTC-3'

[8] Target Gene-B (Underlined Part; Complementary Region)
5'-GAAGGTGTGC TTACAAGTGC TAATAATT CACCT-GTTTG AGGGTGGA TA GCAGTACCTG AGCCAT-AATC AT TTTTCATGTT-3'

[9] Methylated probe-1 (Underlined Part; Mid-Region)
5'-☐TGCTGACTT AACCGGATAC-GATTATGGCT CAG-GTACTGC T-3'

[10] Methylated Probe-2 (Underlined Part; Mid-Region)
5'(phosphorylated)-ATCCACCCT CAAACAGGTG-GAT-TGGTACT GCGAG ATAG☐3'

[11] Methylated Probe-3 (Underlined Part; Mid-Region)
5'-☐ACGCTFTCT GCGTGTATAG-CACCTGTTTG AGGGTGGATA-3'

[12] Methylated Probe-4 (Underlined Part; Mid-Region)
5'(phosphorylated)-GCAGTACCTG AGCCATAATC-CTA-GAACGGA TCGT ACTTC☐3'

[13] Cross-Linking Probe-5
5'-CTATACACGC AGAAAGCGTC-CGAAGTACGA TCCGTTCTAG-3'

[14] Cross-Linking Probe-6
5'-GTATCCGGTT AAGTCAGCAC-CCTATCTCGC AGTACCATTC-3'

(1) Object

The object was confirmation of dimer-forming probes produced by ligation dependent on hybridization with the target gene and confirmation of the target gene by the formation of a self-assembly substance using the ligated dimer-forming probes and the cross-linking probes.

(2) Materials
(a) As target genes, the synthetic oligonucleotide-probes, a target gene-A and a target gene-B, originating in a PBP gene of MRSA were used. The target genes were prepared at a concentration of 1 pmol/μL.
(b) A pair of dimer-forming probes having the mid-regions complementary to the target gene-A and the target gene-B, respectively, and a corresponding pair of cross-linking probes (a cross-linking probe-5 and a cross-linking probe-6) were prepared. The above pair of dimer-forming probes were methylated at the 5' end and the 3' end, cleaved at the mid-regions, and phosphorylated at the 5' end of the cleaved sites, thereby providing probes (methylated probes-1 to 4). These probes were prepared at a concentration of 50 pmoles/μL, respectively.
(c) As a buffer solution, 20×SSC (3 M-NaCl, 0.3 M-$C_6H_5O_7Na_3.2H_2O$, pH 7.0) was used.

(3) Method (a) Preparation of Reaction Solutions

Into a 0.2 mL tube were added 1 μL each of the target genes-A and B, 1 μL each of the methylated probes-1 to 4, 1 μL of a thermostable ligase (Tsc-Ligase, product of Nippon Roche, K.K.) and 2 μL of the 10× incubation buffer included in the ligase product, and the final volume of the reaction solution was adjusted to 20 μL with sterile distilled water (Example 17). For the above reaction solution, a reaction solution without adding the target genes was also prepared as a control (Comparative Example 1).

(b) Gene Amplification Method by Methylated Probes Using Thermostable Ligase

Each of the above reaction solutions was allowed to react for 3 minutes at 95° C., followed by 40 cycles of [for 15 seconds at 94° C. → for 4 minutes at 63° C.] using a thermal cycler (manufactured by PerkinElmer Inc.) to amplify the dimer-forming probes by ligation reaction. Next, the ligase was inactivated by heating for 10 minutes at 99° C., and the produced dimer-forming probes were converted into a single strand form by cooling on ice.

(c) Treatment with Exonuclease

After the above reaction, 1 μL of exonuclease (Exonuclease VII, product of USB Corp.) was added to the reaction solution, and the reaction was carried out for 60 minutes at 37° C. A control to which sterile distilled water was added in place of the exonuclease was also processed in a similar way. The reaction solution after the reaction was run on electrophoresis by PAGE using 6% denatured polyacrylamide (7 M urea).

(d) Method for Forming a Self-Assembly Substance.

To each of the reaction solutions after the above reaction was added 20×SSC (final concentration: 10×SSC) and the formation reaction of a self-assembly substance was carried out for 30 seconds at 94° C. and then 1 hour at 70° C. using a thermal cycler (manufactured by PerkinElmer Inc.).

(e) Confirmation of a Self-Assembly Substance by Agarose Gel Electrophoresis

To 8 μL of the reaction solution after the formation reaction of a self-assembly substance was added 2 μL of a loading buffer, and then gel electrophoresis was carried out for 30 minutes at 100 volts using 2% of NuSieve 3:1 agarose gel (product of Bio Whittaker Molecular Applications). DNA marker (λ Hind III digest) was used as a molecular size marker.

(4) Results

The results of electrophoresis of Example 17 and Comparative Example 1 by denaturing PAGE are shown in FIG. 47. As shown in Lane 1 in FIG. 47 (Example 17, untreated with the enzyme), the cleaved dimer-forming probes were ligated in the presence of the target genes and a band indicated by the arrow (a) was detected. As shown in Lane 3 in FIG. 47 (Example 17, treated with the enzyme), a band was detected at the same location as that indicated by arrow (a) in Lane 1, since the ligated dimer-forming probes had not been degraded by the treatment with the exonuclease. On the other hand, when the target genes were not present, the cleaved dimer-forming probes were not ligated, and no band was detected at the location of (a), as shown in Lane 2 in FIG. 47 (Comparative Example 1, untreated with the enzyme) and Lane 4 in FIG. 47 (Comparative Example 1, treated with the enzyme). Further, the non-ligated methylated probes detected at the location indicated by arrow (b) in Lane 1 and 2 were degraded by the treatment with the exonuclease. Therefore, the band of the non-ligated methylated probes was not detected in Lane 3 and Lane 4.

Figure 48:
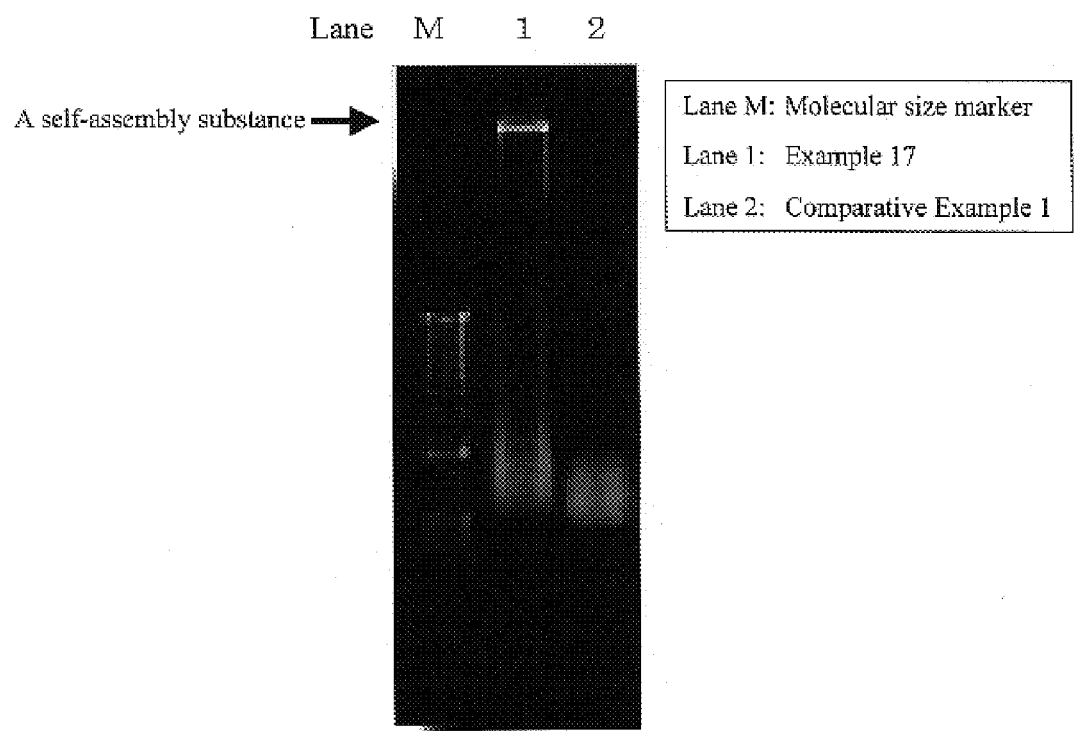
FIG. 48 is a photograph showing the results of agarose gel electrophoresis of Example 17 and Comparative Example 1.

The results of the agarose gel electrophoresis of Example 17 and Comparative Example 1 are shown in FIG. 48. The ligated dimer-probes formed a self-assembly substance by reacting with the cross-linking probes (Lane 1 in FIG. 48, Example 17). On the other hand, the non-ligated dimer-probes which are the unreacted probes did not form a self-assembly substance even after reacting with the cross-linking probes (Lane 2 in FIG. 48, Comparative Example 1).

Example 18 and Comparative Example 2

The oligonucleotide-probes used in Example 18 and Comparative Example 2 are shown below, where □ indicates methylated bases.

[15] Amplifying Probe-1 (Methylated Probe)
5'(phosphorylated)-CGGAAGCTCC TATGACAAT G̅-3'

[16] Amplifying Probe-2 (Methylated Probe)
5'(phosphorylated)-GTTGATCGTC TCGGCTAGT G̅-3'

[17] Amplifying Probe-3 (Non-Methylated Probe)
5'(phosphorylated)-CGGAAGCTCC TATGACAATG-3'

[18] Amplifying Probe-4 (Non-Methylated Probe)
5'(phosphorylated)-GTTGATCGTC TCGGCTAGTG-3'

[19] Dimer-Forming Probe-3'
5'-TATGACAATG-GATCCTAGAC-CGGAAGCTCC-3'

[20] Dimer-Forming Probe-4
5'-TCGGCTAGTG-GTCTAGGATC-GTTGATCGTC-3'

(1) Object

The object was confirmation of gene amplification with the methylated amplifying probes by a thermostable DNA polymerase and confirmation of amplified gene by the formation of a self-assembly substance.

(2) Materials
(a) The target gene used was a part of the base sequences in IS6110 region of *Mycobacterium tuberculosis* which was used as a template DNA.
(b) A pair of amplifying probes-1 and 2 methylated at the 3' end, respectively (Example 18), and a pair of un-methylated amplifying probes-3 and 4 (Comparative Example 2) were prepared as amplifying probes to amplify the target gene. As dimer forming probes, a pair of dimer-forming probes-3 and 4 which were designed to use the amplified synthetic probes as cross-linking probes were prepared. These probes were prepared at a concentration of 50 pmoles/μL, respectively.

(c) As a buffer solution, 20×SSC (3 M-NaCl, 0.3 M-C$_6$H$_5$O$_7$Na$_3$.2H$_2$O, pH 7.0) was used.

(3) Method (a) Preparation of Reaction Solutions

Into a 0.2 mL tube were added 1 μL of the template DNA, 0.5 μL each of amplifying probes-1 and 2, 5 μL of 10×PCR buffer (10×Ex Taq Buffer: product of Takara Shuzo Co., Ltd.), 4 μL of dNTP Mixture [(2.5 mM each): product of Takara Shuzo Co., Ltd.] and 0.1 μL of Taq polymerase [TaKaRa Ex Taq (5 units/μL): product of Takara Shuzo Co., Ltd.], and the final volume of the mixture was adjusted to 50 μL with sterile distilled water to make a PCR solution (Example 18). As a control, for the above reaction solution, a PCR solution in which amplifying probes-3 and 4 were added in place of amplifying probes-1 and 2, was also prepared (Comparative Example 2).

(b) PCR

Using a thermal cycler (manufactured by PerkinElmer Inc.), each of the above PCR solutions was treated for 1 minute at 94° C., followed by 35 cycles of [for 30 seconds at 94° C. → for 2 minutes at 60° C.].

(c-1) Exonuclease Treatment (1)

10 μL of the above reaction solution after the PCR was transferred into another 0.2 mL tube, and 0.1 μL of the exonuclease (T7 Gene 6 Exonuclease, Product of Amersham Pharmacia Biotech) and 2 μL of 5×T7 Gene 6 Exonuclease Buffer (Product of Amersham Pharmacia Biotech) were added. The final volume of the reaction solution was adjusted to 13 μL with sterile distilled water. This solution was subjected to reaction for 30 minutes at 37° C., and then heated for 15 minutes at 85° C. to inactivate the exonuclease. A control to which sterile distilled water was added in place of the exonuclease was also processed in a similar way. After treatment with the exonuclease, 10 μL of the reaction solution was run on electrophoresis using 16% polyacrylamide gel (29:1, product of Bio-Rad Laboratories). After electrophoresis, the gel was stained with ethidium bromide.

(c-2) Exonuclease Treatment (2)

The above reaction solution of Example 18 after the PCR was treated with the exonuclease under the same conditions and by the same procedures as the reaction condition of the above exonuclease treatment (1) except that reactions [for 30 minutes at 37° C.→for 15 minutes at 85° C.] were replaced by reaction [for 30 minutes at 37° C.→for 30 minutes at 57° C.→for 30 minutes at 37° C.→for 15 minutes at 85° C.].

(d) Formation Reaction of a Self-Assembly Substance

To each of the above reaction solutions of Example 18 after the above exonuclease treatment (1) and (2) was added 1 μL of dimer-forming probes-3 and 4, respectively, and then 20×SSC was added up to a final concentration of 10×SSC, followed by treatment for 30 seconds at 94° C. Thereafter, formation reaction of a self-assembly substance was allowed to proceed for 1 hour at 60° C.

(e) Confirmation of a Self-Assembly Substance by Agarose Gel Electrophoresis

Confirmation of a self-assembly substance was performed by the same procedures and under the same conditions as those in Example 17.

(4) Results

The results of electrophoresis of Example 18 and Comparative Example 2 by PAGE are shown in FIG. 49. In FIG. 49, Lanes represent the followings respectively: Lane 1, a DNA Ladder marker of 10 bp; Lane 2, a single-stranded oligonucleotide of 40 mers used as a control; Lane 3, a single-stranded oligonucleotide of 60 mers used as a control; Lane 4, Comparative Example 2 (untreated with the enzyme); Lane 5, Example 18 (untreated with the enzyme); Lane 6, Comparative Example 2 (treated with the enzyme); and Lane 7, Example 18 (treated with the enzyme).

As shown in Lane 5 and Lane 7 in FIG. 49, in Example 18 using methylated amplifying probes, a band corresponding to a synthetic probe that is an objective amplified product by the PCR was detected at the location of 40 bp, and the exonuclease treatment caused degradation of the band of 40 bp, giving rise to a band newly at the location of 20 bp. This band of 20 bp corresponds to hybrids of the synthetic probe of 20 mers degraded by exonuclease treatment and the unreacted amplifying probes of 20 mers. Thus, it is apparent that treatment of the amplified products using the methylated amplifying probes with the exonuclease allowed the complementary chain to be degraded, resulting in a pair of objective cross-linking probes of 20 mers.

On the other hand, as shown in Lane 4 and Lane 6 in FIG. 49, in Comparative Example 2 (control) using the un-methylated probes as the amplifying probes, the band corresponding to the objective amplified product by the PCR was detected at the location of 40 bp, but the exonuclease treatment caused only degradation of the band of 40 bp without giving any new detectable band of different sizes.

Figure 50:
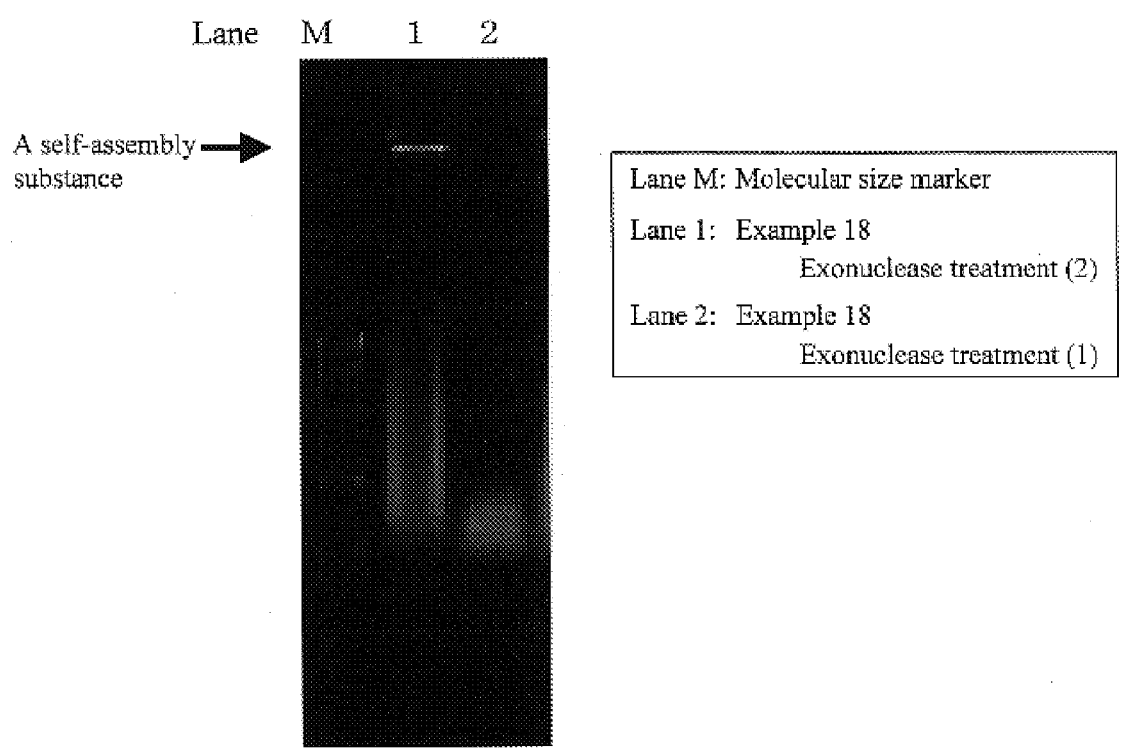
FIG. 50 is a photograph showing the result of agarose gel electrophoresis of Example 18.

The result of agarose gel electrophoresis of Example 18 is shown in FIG. 50. In Lane 1 [exonuclease treatment (2)], formation of a self-assembly substance from the synthetic probes and the dimer-forming probes were confirmed, since the unreacted amplifying probes serving as complementary chains to the synthetic probes had been removed.

On the other hand, in Lane 2 [exonuclease treatment (1)] where the dimer-forming probes were added under the condition that the synthetic probes were forming hybrids with the unreacted amplifying probes, formation of a self-assembly substance was not confirmed.

Example 19 and Comparative Examples 3 to 5

The oligonucleotide-probes composed of DNA and RNA used in Example 19 are shown below, where ☐ indicates RNA.

[21] Chimera Type Amplifying Probe-1 (3 Bases at the 3' end Composed of

5' (phosphorylated)-CGGAAGCTCC TATGACA AUG -3'

[22] Chimera Type Amplifying Probe-2 (3 Bases at the 3' end Composed of RNA)

5'(phosphorylated)-GTTGATCGTC TCGGCTA GUG -3'

(1) Object

The object was confirmation of gene amplification with chimera type amplifying probes (probes composed of DNA and RNA) by a nucleic acid polymerase having strand displacement activity and confirmation of amplified gene by the formation of a self-assembly substance.

(2) Materials (a) The target gene used was a part of the base sequences in IS6110 region of *Mycobacterium tuberculosis* which was used as a template DNA.

(b) A pair of chimera type amplifying probes-1 and 2 with 3 bases at the 3' ends composed of RNA (Example 19) was prepared as amplifying probes to amplify the target gene. As dimer-forming probes, the pair of dimer-forming probes-3 and 4 as those in Example 18 was used. These probes were prepared at a concentration of 50 pmoles/μL, respectively.

(c) As a buffer solution, 20×SSC (3 M-NaCl, 0.3 M-$C_6H_5O_7Na_3.2H_2O$, pH 7.0) was used.

(3) Method (a) Preparation of Reaction Solutions

Into a 0.2 mL tube were added 1 μL of the template DNA, 0.25 μL each of chimera type amplifying probes-1 and 2, 7.5 μL of Tris buffer (0.1 M Tris-hydrochloride buffer, pH 7.5), 1 μL of dNTP Mixture [(2.5 mM each): product of Takara Shuzo Co., Ltd.], 0.15 μL of Bca polymerase (22 U/μL: product of Takara Shuzo Co., Ltd.), 0.2 μL of BSA (20 mg/mL: product of Takara Shuzo Co., Ltd.), 6.5 μL of 10% glycerol, 1 μL of DMSO, 5 μL of $MgCl_2$ (50 mM) and 0.5 μL of RNase H (60 U/μL: product of Takara Shuzo Co., Ltd.), and the final volume of the reaction solution was adjusted to 25 μL with sterile distilled water.

As a control, the reaction solution containing 1 μL of sterile distilled water in place of the template DNA was also prepared (Comparative Example 3).

(b) Amplification Reaction

Using a thermal cycler (manufactured by PerkinElmer Inc.), the above reaction solution was allowed to react for 60 minutes at 60° C., followed by heating for 5 minutes at 95° C. to inactivate the enzyme. This reaction solution was called a "synthetic probe" solution.

(c) Detection of Amplified Product by Acrylamide Gel Electrophoresis

8 μL of the above synthetic probe solution were run on electrophoresis using 16% polyacrylamide gel (29:1, product of Bio-Rad Laboratories). After the electrophoresis, the gel was stained with ethidium bromide.

(d) Formation Reaction of a Self-Assembly Substance

Into 0.2 mL tube were added 1 μL each of dimer-forming probes-3 and 4 and 12 μL of 20×SSC, and then sterile distilled water was added up to a final volume of 20 μL.

This reaction solution was treated for 30 seconds at 94° C., and then allowed to react for 18 hours at 60° C. The resulting solution was called a "dimer-probe" solution.

Next, for formation reaction of a self-assembly substance, 5 μL of the synthetic probe solution, 10 μL of the dimer-probe solution and 5 μL of 20×SSC solution were added into another 0.2 mL tube, and the mixture was allowed to react for 18 hours at 60° C.

The reaction was carried out using the synthetic probe solution alone (Comparative Example 4) or the dimer-probe solution alone (Comparative Example 5) as controls.

(e) Confirmation by Fluorescent Microscope

To 5 μL of the solution after (d) formation reaction of a self-assembly substance described above was added 5 μL of 1000-fold diluted solution of ethidium bromide (originally 10 mg/mL), and then the mixture was left standing for 30 minutes. 3 μL of this solution was dropped onto a slide glass and observed by a fluorescent microscope.

(4) Results

1: Detection of Amplified Products by Acrylamide Gel Electrophoresis

Figure 51:
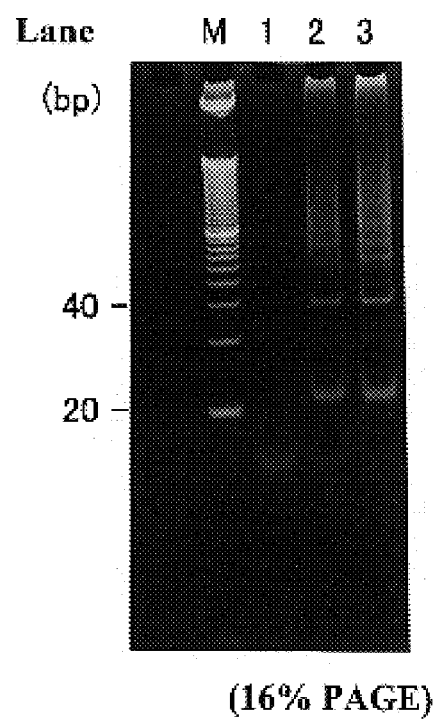
FIG. 51 is a photograph showing the results of PAGE of Example 19 and Comparative Example 3.

The results of acrylamide gel electrophoresis of Example 19 and Comparative Example 3 are shown in FIG. 51. Lane M represents a DNA Ladder marker of 10 bp, Lane 1 represents Comparative Example 3, and Lanes 2 and 3 represent Example 19. As shown in FIG. 51, bands of amplified products were detected at the locations corresponding to 40 bp and 20 bp, in only Example 19 in which the target DNA was added. This band of 20 bp is a hybrid of the unreacted probe of 20 mers and the split synthetic probe of 20 mers, wherein the split synthetic probe was produced by degrading the RNA part in the amplified synthetic probe of 40 bp by coexisting RNase H.

2: Confirmation by Fluorescent Microscope

Figure 52:
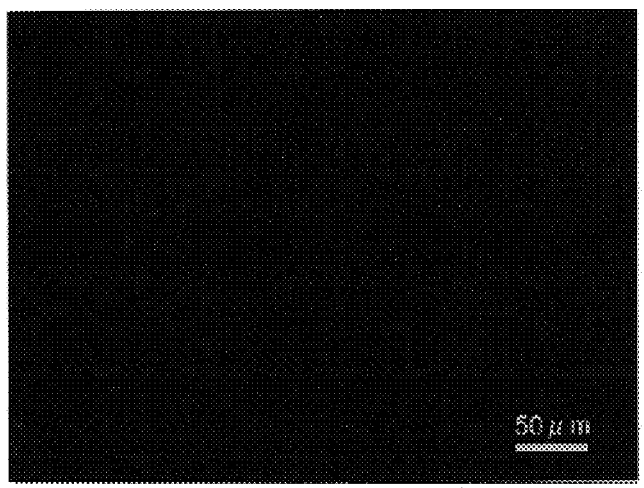
FIG. 52 is a photograph showing the result of Example 19 obtained by a fluorescent microscope.
Figure 53:
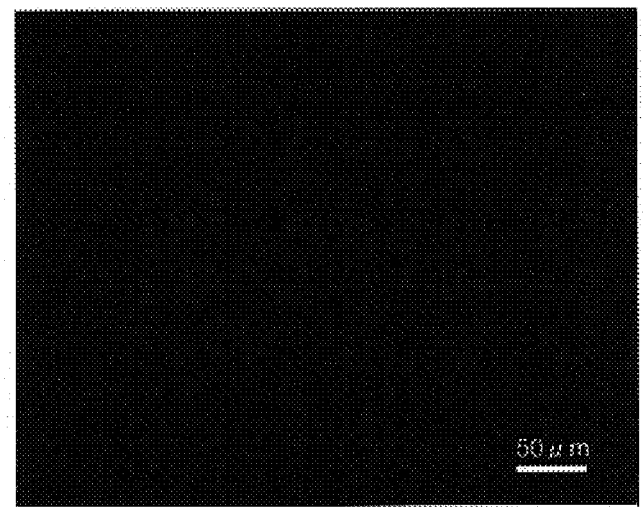
FIG. 53 is a photograph showing the result of Comparative Example 4 obtained by a fluorescent microscope.
Figure 54:
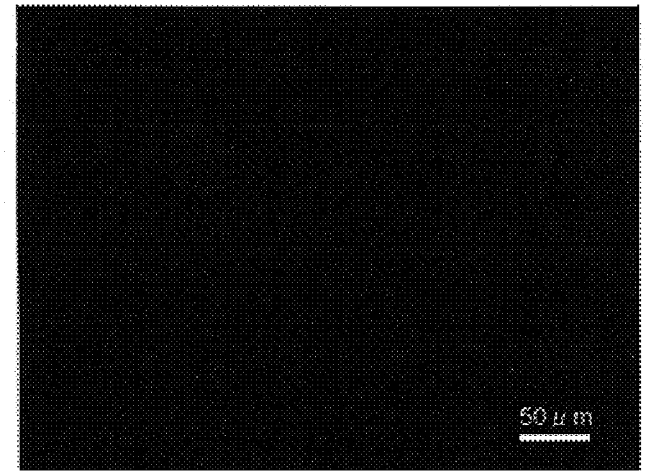
FIG. 54 is a photograph showing the result of Comparative Example 5 obtained by a fluorescent microscope.

The results obtained by a fluorescent microscope of Example 19 and Comparative Examples 4 and 5 are shown in FIGS. 52 to 54. A self-assembly substance was confirmed as particulates on the slide glasses, only when the mixed solution of the dimer-probe and the synthetic probe was allowed to react (Example 19).

CAPABILITY OF EXPLOITATION IN INDUSTRY

As described above, the method for forming a self-assembly substance using synthetic probes obtained by the gene amplification reaction according to the present invention makes it possible to form a self-assembly substance using oligonucleotides without using any special instruments or reagents needed in EIA. The method for detecting a gene according to the present invention makes it possible to detect specific genes at a low cost and in a simple way without using any special instruments or complicated procedures. The self-assembly substance according to the present invention is formed efficiently by the method for forming a self-assembly substance using oligonucleotides according to the present invention.

The invention claimed is:

1. A method for forming a self-assembly substance of oligonucleotides, said method comprising:
   (1) providing n (n≧1) dimer-forming probe-bearing groups formed from a first group to a (2n−1)th group in turn, wherein each group includes a plurality of pairs of dimer-forming probes composed of a pair of an oligonucleotide No. 1 and an oligonucleotide No. 2, each oligonucleotide having 3 regions of a 3' side region, a mid-region and a 5' side region, in which the mid-regions of the oligonucleotides No. 1 and No. 2 have base sequences complementary to each other, and the 3' side regions and 5' side regions thereof have base sequences not complementary to each other;
   (2) providing n (n≧1) cross-linking probe-bearing groups formed from a second group to a 2 nth group in turn, wherein each group includes a plurality of pairs of cross-linking probes composed of a pair of an oligonucleotide No. 1 and an oligonucleotide No. 2, each oligonucleotide having 2 regions of a 3' side region and a 5' side region, in which the 3' side regions and the 5' side regions of the oligonucleotides No. 1 and No. 2 have base sequences not complementary to each other, and the cross-linking probes having base sequences capable of cross-linking dimers formed from the dimer-forming probes; and
   (3) hybridizing the dimer-forming probes of the dimer-forming probe-bearing groups with the cross-linking probes of the cross-linking probe-bearing groups, wherein the oligonucleotides are self-assembled to form the self-assembly substance of oligonucleotides,
   wherein in the case of n=1, base sequences of the probes are made complementary to each other in the following respective pairs:
   (a) the 3' side region of the oligonucleotide No. 1 of the first group of the dimer-forming probe-bearing groups and the 3' side region of the oligonucleotide No. 1 of the second group of the cross-linking probe-bearing groups;
   (b) the 5' side region of the oligonucleotide No. 2 of the first group of the dimer-forming probe-bearing groups and the 5' side region of the oligonucleotide No. 2 of the second group of the cross-linking probe-bearing groups;
   (c) the 3' side region of the oligonucleotide No. 2 of the second group of the cross-linking probe-bearing groups and the 3' side region of the oligonucleotide No. 2 of the first group of the dimer-forming probe-bearing groups; and
   (d) the 5' side region of the oligonucleotide No. 1 of the second group of the cross-linking probe-bearing groups and the 5' side region of the oligonucleotide No. 1 of the first group of the dimer-forming probe-bearing groups.

2. A method for forming a self-assembly substance of oligonucleotides, said method comprising:
   (1) providing n (n≧1) dimer-forming probe-bearing groups formed from a first group to a (2n−1)th group in turn, wherein each group includes a plurality of pairs of dimer-forming probes composed of a pair of an oligonucleotide No. 1 and an oligonucleotide No. 2, each oligonucleotide having 3 regions of a 3' side region, a mid-region and a 5' side region, in which the mid-regions of the oligonucleotides No. 1 and No. 2 have base sequences complementary to each other, and the 3' side regions and 5' side regions thereof have base sequences not complementary to each other;
   (2) providing n (n≧1) cross-linking probe-bearing groups formed from a second group to a 2 nth group in turn, wherein each group includes a plurality of pairs of cross-linking probes composed of a pair of an oligonucleotide No. 1 and an oligonucleotide No. 2, each oligonucleotide having 2 regions of a 3' side region and a 5' side region, in which the 3' side regions and the 5' side regions of the oligonucleotides No. 1 and No. 2 have base sequences not complementary to each other, and the cross-linking probes having base sequences capable of cross-linking dimers formed from the dimer-forming probes; and
   (3) hybridizing the dimer-forming probes of the dimer-forming probe-bearing groups with the cross-linking probes of the cross-linking probe-bearing groups, wherein the oligonucleotides are self-assembled to form the self-assembly substance of oligonucleotides,
   wherein in the case of n=1, base sequences of the probes are made complementary to each other in the following respective pairs:
   (a) the 3' side region of the oligonucleotide No. 1 of the first group of the dimer-forming probe-bearing groups and the 3' side region of the oligonucleotide No. 1 of the second group of the cross-linking probe-bearing groups;
   (b) the 5' side region of the oligonucleotide No. 2 of the first group of the dimer-forming probe-bearing groups and the 5' side region of the oligonucleotide No. 1 of the second group of the cross-linking probe-bearing groups;
   (c) the 3' side region of the oligonucleotide No. 2 of the first group of the dimer-forming probe-bearing groups and the 3' side region of the oligonucleotide No. 2 of the second group of the cross-linking probe-bearing groups; and (d) the 5' side region of the oligonucleotide No. 1 of the first group of the dimer-forming probe-bearing groups and the 5' side region of the oligonucleotide No. 2 of the second group of the cross-linking probe-bearing groups.

3. A method for forming a self-assembly substance of oligonucleotides, said method comprising:
   (1) providing n (n≧1) dimer-forming probe-bearing groups formed from a first group to a (2n−1)th group in turn, wherein each group includes a plurality of pairs of dimer-forming probes composed of a pair of an oligonucleotide No. 1 and an oligonucleotide No. 2, each oligonucleotide having 3 regions of a 3' side region, a mid-region and a 5' side region, in which the mid-regions of the oligonucleotides No. 1 and No. 2 have base sequences complementary to each other, and the 3' side regions and 5' side regions thereof have base sequences not complementary to each other;
   (2) providing n (n≧1) cross-linking probe-bearing groups formed from a second group to a 2 nth group in turn, wherein each group includes a plurality of pairs of cross-linking probes composed of a pair of an oligonucleotide No. 1 and an oligonucleotide No. 2, each oligonucleotide having 2 regions of a 3' side region and a 5' side region, in which the 3' side regions and the 5' side regions of the oligonucleotides No. 1 and No. 2 have base sequences not complementary to each other, and the cross-linking probes having base sequences capable of cross-linking dimers formed from the dimer-forming probes; and
   (3) hybridizing the dimer-forming probes of the dimer-forming probe-bearing groups with the cross-linking probes of the cross-linking probe-bearing groups, wherein the oligonucleotides are self-assembled to form the self-assembly substance of oligonucleotides,
   wherein in the case of n≧2 base sequences of the probes are made complementary to each other in the following respective pairs:
   (a) the 3' side region of the oligonucleotide No. 1 of the (2n−3)th group of the dimer-forming probe-bearing groups and the 3' side region of the oligonucleotide No. 1 of the (2n−2)th group of the cross-linking probe-bearing groups;
   (b) the 5' side region of the oligonucleotide No. 2 of the (2n−3)th group of the dimer-forming probe-bearing groups and the 5' side region of the oligonucleotide No. 2 of the (2n−2)th group of the cross-linking probe-bearing groups;
   (c) the 3' side region of the oligonucleotide No. 2 of the (2n−2)th group of the cross-linking probe-bearing groups and the 3' side region of the oligonucleotide No. 2 of the (2n−1)th group of the dimer-forming probe-bearing groups;
   (d) the 5' side region of the oligonucleotide No. 1 of the (2n−2)th group of the cross-linking probe-bearing groups and the 5' side region of the oligonucleotide No. 1 of the (2n−1)th group of the dimer-forming probe-bearing groups;
   (e) the 3' side region of the oligonucleotide No. 1 of the last group of the dimer-forming probe-bearing groups and the 3' side region of the oligonucleotide No. 1 of the last group of the cross-linking probe-bearing groups;
   (f) the 5' side region of the oligonucleotide No. 2 of the last group of the dimer-forming probe-bearing groups and the 5' side region of the oligonucleotide No. 2 of the last group of the cross-linking probe-bearing groups;
   (g) the 3' side region of the oligonucleotide No. 2 of the last group of the cross-linking probe-bearing groups and the 3' side region of the oligonucleotide No. 2 of the first group of the dimer-forming probe-bearing groups; and
   (h) the 5' side region of the oligonucleotide No. 1 of the last group of the cross-linking probe-bearing groups and the 5' side region of the oligonucleotide No. 1 of the first group of the dimer-forming probe-bearing groups.

4. A method for forming a self-assembly substance of oligonucleotides, said method comprising:
   (1) providing n (n≧1) dimer-forming probe-bearing groups formed from a first group to a (2n−1)th group in turn, wherein each group includes a plurality of pairs of dimer-forming probes composed of a pair of an oligonucleotide No. 1 and an oligonucleotide No. 2, each oligonucleotide having 3 regions of a 3' side region, a mid-region and a 5' side region, in which the mid-regions of the oligonucleotides No. 1 and No. 2 have base sequences complementary to each other, and the 3' side regions and 5' side regions thereof have base sequences not complementary to each other;
   (2) providing n (n≧1) cross-linking probe-bearing groups formed from a second group to a 2 nth group in turn, wherein each group includes a plurality of pairs of cross-linking probes composed of a pair of an oligonucleotide No. 1 and an oligonucleotide No. 2, each oligonucleotide having 2 regions of a 3' side region and a 5' side region, in which the 3' side regions and the 5' side regions of the oligonucleotides No. 1 and No. 2 have base sequences not complementary to each other, and the cross-linking probes having base sequences capable of cross-linking dimers formed from the dimer-forming probes; and
   (3) hybridizing the dimer-forming probes of the dimer-forming probe-bearing groups with the cross-linking probes of the cross-linking probe-bearing groups, wherein the oligonucleotides are self-assembled to form the self-assembly substance of oligonucleotides,
   wherein in the case of n≧2 base sequences of the probes are made complementary to each other in the following respective pairs:
   (a) the 3' side region of the oligonucleotide No. 1 of the (2n−3)th group of the dimer-forming probe-bearing groups and the 3' side region of the oligonucleotide No. 1 of the (2n−2)th group of the cross-linking probe-bearing groups;
   (b) the 5' side region of the oligonucleotide No. 2 of the (2n−3)th group of the dimer-forming probe-bearing groups and the 5' side region of the oligonucleotide No. 2 of the (2n−2)th group of the cross-linking probe-bearing groups;
   (c) the 3' side region of the oligonucleotide No. 2 of the (2n−2)th group of the cross-linking probe-bearing groups and the 3' side region of the oligonucleotide No. 2 of the (2n−1)th group of the dimer-forming probe-bearing groups;
   (d) the 5' side region of the oligonucleotide No. 1 of the (2n−2)th group of the cross-linking probe-bearing groups and the 5' side region of the oligonucleotide No. 1 of the (2n−1)th group of the dimer-forming probe-bearing groups;
   (e) the 3' side region of the oligonucleotide No. 1 of the last group of the dimer-forming probe-bearing groups and the 3' side region of the oligonucleotide No. 1 of the last group of the cross-linking probe-bearing groups;
   (f) the 5' side region of the oligonucleotide No. 2 of the last group of the dimer-forming probe-bearing groups and the 5' side region of the oligonucleotide No. 1 of the last group of the cross-linking probe-bearing groups;

(g) the 3' side region of the oligonucleotide No. 2 of the last group of the cross-linking probe-bearing groups and the 3' side region of the oligonucleotide No. 2 of the first group of the dimer-forming probe-bearing groups; and (h) the 5' side region of the oligonucleotide No. 2 of the last group of the cross-linking probe-bearing groups and the 5' side region of the oligonucleotide No. 1 of the first group of the dimer-forming probe-bearing groups.

5. The method for forming a self-assembly substance of oligonucleotides according to any one of claims 1-4, wherein at least one of the dimer-forming probes and the cross-linking probes is an oligonucleotide synthesized by a gene amplification reaction.

6. The method for forming a self-assembly substance of oligonucleotides according to any one of claims 1-4, wherein the hybridizing of the dimer-forming probes of the dimer-forming probe-bearing groups with the cross-linking probes of the cross-linking probe-bearing groups comprises:

forming dimers from the dimer-forming probes of the dimer-forming probe-bearing groups; and hybridizing the dimers with the cross-linking probes of the cross-linking probe-bearing groups.

7. The method for forming a self-assembly substance of oligonucleotides according to any one of claims 1-4, wherein the pairs of the dimer-forming probes comprise plural kinds of pairs of dimer-forming probes differing in the mid-regions.

8. The method for forming a self-assembly substance of oligonucleotides according to any one of claims 1-4, wherein the pairs of the dimer-forming probes are provided with the same base sequences at the 3' side regions and/or the 5' side regions thereof.

9. The method for forming a self-assembly substance of oligonucleotides according to any one of claims 5, wherein at least one of the cross-linking probes is an oligonucleotide which comprises the 2 regions of the cross-linking probes and is synthesized by the gene amplification reaction.

10. The method for forming a self-assembly substance of oligonucleotides according to claim 9, wherein the oligonucleotides synthesized by the gene amplification reaction are gene fragments complementary to each other, and the gene fragments comprise at least 4 regions and include 2 regions complementary to the 5' side region and the 3' side region of the oligonucleotides of the (2n−1)th group, respectively.

11. The method for forming a self-assembly substance of oligonucleotides according to any one of claims 1-4, wherein the dimer-forming probes and the cross-linking probes are comprised of at least one base selected from the group consisting of DNA, RNA, PNA and LNA.

12. The method for forming a self-assembly substance of oligonucleotides according to any one of claims 1-4, wherein at least one G (guanine) or C (cytosine) is arranged at one or more ends of the complementary base sequence regions of the dimer-forming probes and the cross-linking probes, and when hybridizing the probes, at least one G-C bond is formed at the ends of the complementary base sequence regions.

\* \* \* \* \*

UNITED STATES PATENT AND TRADEMARK OFFICE
CERTIFICATE OF CORRECTION

| | | |
|---|---|---|
| PATENT NO. | : 7,393,636 B2 | Page 1 of 1 |
| APPLICATION NO. | : 10/495065 | |
| DATED | : July 1, 2008 | |
| INVENTOR(S) | : Mitsugu Usui et al. | |

It is certified that error appears in the above-identified patent and that said Letters Patent is hereby corrected as shown below:

TITLE PAGE

Item (30), Foreign Application Priority Data, "May 8, 2002 (JP) 2002-132402" should read -- November 8, 2001 (JP) 2001-342709 and May 8, 2002 (JP) 2002-132402 --.

Signed and Sealed this

Fourth Day of August, 2009

JOHN DOLL
*Acting Director of the United States Patent and Trademark Office*